(12) United States Patent
Green et al.

(10) Patent No.: US 6,176,576 B1
(45) Date of Patent: *Jan. 23, 2001

(54) EYEWEAR SUPPORTED BY A WEARER'S CONCHA OF AN EAR

(75) Inventors: Robert W. Green; Aaron L. Bright; Michael S. Tutor, all of Memphis, TN (US)

(73) Assignee: Radians, Inc., Memphis, TN (US)

(*) Notice: Under 35 U.S.C. 154(b), the term of this patent shall be extended for 0 days.

This patent is subject to a terminal disclaimer.

(21) Appl. No.: 09/327,762

(22) Filed: Jun. 7, 1999

Related U.S. Application Data

(63) Continuation-in-part of application No. 29/104,345, filed on May 3, 1999, now Pat. No. Des. 426,845, and application No. 09/114,391, filed on Jul. 13, 1998, now abandoned, which is a continuation-in-part of application No. 08/870,433, filed on Jun. 6, 1997, now Pat. No. 5,781,272.

(60) Provisional application No. 60/132,205, filed on May 3, 1999.

(51) Int. Cl.[7] .................................................... G02C 5/20

(52) U.S. Cl. ........................ 351/123; 351/111; 351/158

(58) Field of Search ................................... 351/158, 119, 351/118, 41, 111; 128/163; 2/13, 12

(56) References Cited

U.S. PATENT DOCUMENTS

| | | | |
|---|---|---|---|
| D. 178,620 | 8/1956 | Tresise | D57/1 |
| D. 207,919 | 6/1967 | Lui Fai | D57/1 |
| D. 260,774 | 9/1981 | Brown | D16/127 |
| D. 262,491 | 12/1981 | Ebert | D24/67 |
| D. 342,080 | 12/1993 | Cargle | D16/103 |
| D. 352,046 | 11/1994 | Kataoka | D16/309 |
| D. 381,414 | 7/1997 | Westerdal | D24/106 |
| D. 384,092 | 9/1997 | Hall et al. | D16/335 |
| 2,207,705 | 7/1940 | Cox | 179/107 |
| 2,792,457 | 5/1957 | Zapelloni | 179/107 |
| 2,946,394 | 7/1960 | Smith | 181/23 |
| 3,000,462 | 9/1961 | Smith | 181/23 |
| 3,247,330 | 4/1966 | Hinman | 179/107 |
| 3,297,832 | 1/1967 | Brown | 179/107 |
| 3,384,903 | 5/1968 | Malcolm, Jr. | 2/14 |
| 3,431,370 | 3/1969 | Crosby | 179/182 |
| 3,620,608 | 11/1971 | Davis | 5/14 |

(List continued on next page.)

FOREIGN PATENT DOCUMENTS 8917208  7/1990 (GB).

*Primary Examiner*—Hung Xuan Dang
(74) *Attorney, Agent, or Firm*—Walker, McKenzie & Walker, P.C.

(57) ABSTRACT

Eyewear with earpieces supported from a wearer's ear with optional audio apparatus for use by the wearer, having a front frame browpiece portion including a front transparent panel that may be tinted and/or may be designed to correct vision impairments, being supported on a wearer's head by a nose bridge and by at least one earpiece or earplug that is received into the concha of the wearer's ear and/or into the ear canal. The earpiece or earplug is attached to a rear end of its respective temple of the eyewear and the respective temple for the earpiece or earplug is not supported over the wearer's ear. Preferably both temples are only supported by their respective rear earpiece or earplug. The earpieces of some embodiments sealingly and protectively plug the ear canal of the wearer. The eyewear may include an optional microphone, whether as a boom-mounted microphone or an ear microphone, and may include audio earpieces for reproducing sound from an audio signal source. Various earpiece attachments are provided for attaching the earpieces and earplugs to the temples of the eyewear. The temples may have length adjustments and may have spread adjustments to adjust for various-sized wearers' heads. The temples preferably exert an inward pressure on the earpieces and earplugs so as to retain the eyewear on the wearer's head during physical activity. An overglasses embodiment is provided that can be worn over standard eyeglasses.

22 Claims, 40 Drawing Sheets

U.S. PATENT DOCUMENTS

| | | | |
|---|---|---|---|
| 3,856,007 | 12/1974 | Leight | 128/152 |
| 3,943,925 | 3/1976 | Leight . | |
| 4,153,348 | 5/1979 | Walters et al. | 5/20 |
| 4,174,155 | 11/1979 | Herman | 351/158 |
| 4,490,857 | 1/1985 | Leight et al. | 2/209 |
| 4,588,867 | 5/1986 | Konomi | 379/430 |
| 4,632,104 | 12/1986 | Conrow | 13/12 |
| 4,671,265 | 6/1987 | Andersson | 11/2 |
| 4,683,587 | 7/1987 | Silverman | 381/25 |
| 4,751,746 | 6/1988 | Rustin | 2/13 |
| 4,848,861 | 7/1989 | McCulley | 351/123 |
| 4,848,892 | 7/1989 | Sonthonnax | 5/20 |
| 4,856,089 | 8/1989 | Horton . | |
| 4,867,550 | 9/1989 | Jannard | 351/47 |
| 4,896,380 | 1/1990 | Kamitani | 2/428 |
| 4,955,708 | 9/1990 | Kahaney | 7/10 |
| 5,074,375 | 12/1991 | Grozil | 7/2 |
| 5,086,789 | 2/1992 | Tichy | 128/866 |
| 5,208,614 | 5/1993 | Jannard | 351/41 |
| 5,298,691 | 3/1994 | Leight | 181/135 |
| 5,327,178 | 7/1994 | McManigal | 351/158 |
| 5,335,285 | 8/1994 | Gluz | 381/187 |
| 5,345,616 | 9/1994 | Wiedner | 2/446 |
| 5,367,345 | 11/1994 | da Silva | 351/123 |
| 5,404,385 | 4/1995 | Ben-Haim | 377/24.2 |
| 5,410,746 | 4/1995 | Gelber | 455/344 |
| 5,438,698 | 8/1995 | Burton et al. | 455/351 |
| 5,475,449 | 12/1995 | Pyle . | |
| 5,483,975 | 1/1996 | Hirschenbain | 128/864 |
| 5,541,677 | 7/1996 | Huhtala . | |
| 5,581,821 | 12/1996 | Nakano | 2/422 |
| 5,608,808 | 3/1997 | da Silva | 381/183 |
| 5,619,750 | 4/1997 | Allewalt | 2/13 |
| 5,625,903 | 5/1997 | Schultz et al. | 2/209 |
| 5,703,670 | 12/1997 | Callard | 351/123 |
| 5,715,323 | 2/1998 | Walker | 381/187 |
| 5,717,479 | 2/1998 | Rickards | 351/158 |
| 5,718,002 | 2/1998 | Pavlak | 2/423 |
| 5,724,119 | 3/1998 | Leight | 351/158 |
| 5,781,272 | 7/1998 | Bright et al. | 351/123 |
| 5,792,998 | 8/1998 | Gardner, Jr. et al. | 181/130 |
| 5,806,526 | 9/1998 | Rhoad | 128/864 |
| 5,809,574 | 9/1998 | Falco et al. | 2/209 |
| 5,812,659 | 9/1998 | Mauney et al. | 379/430 |

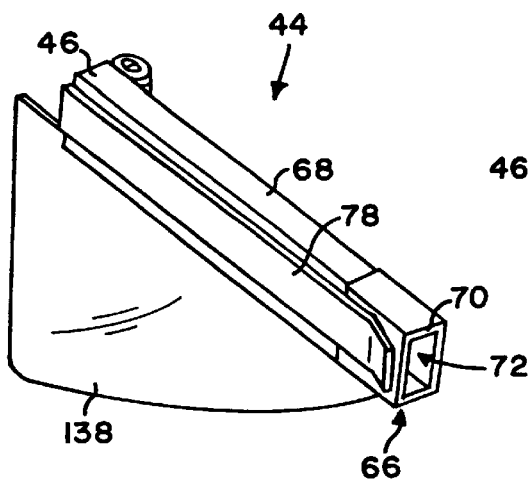
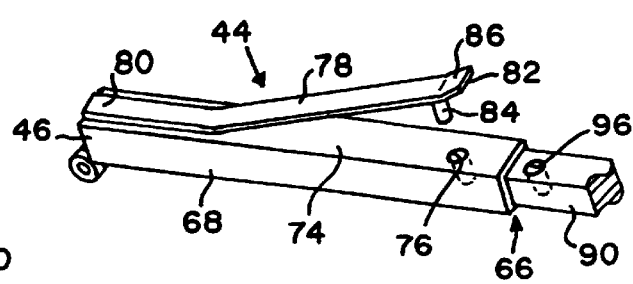
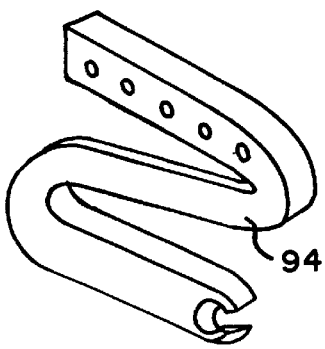
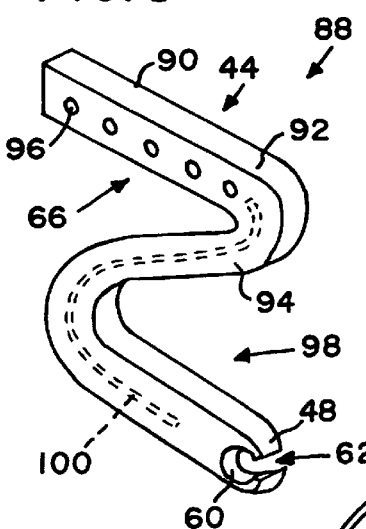
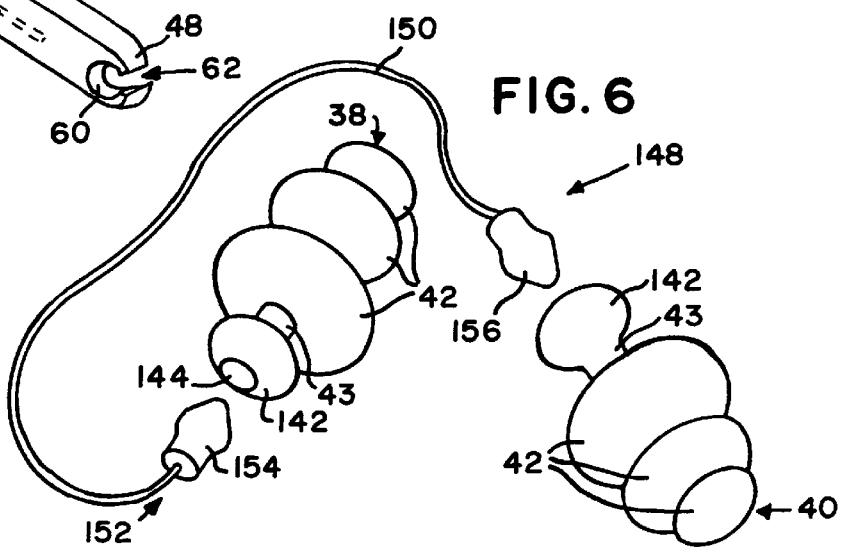

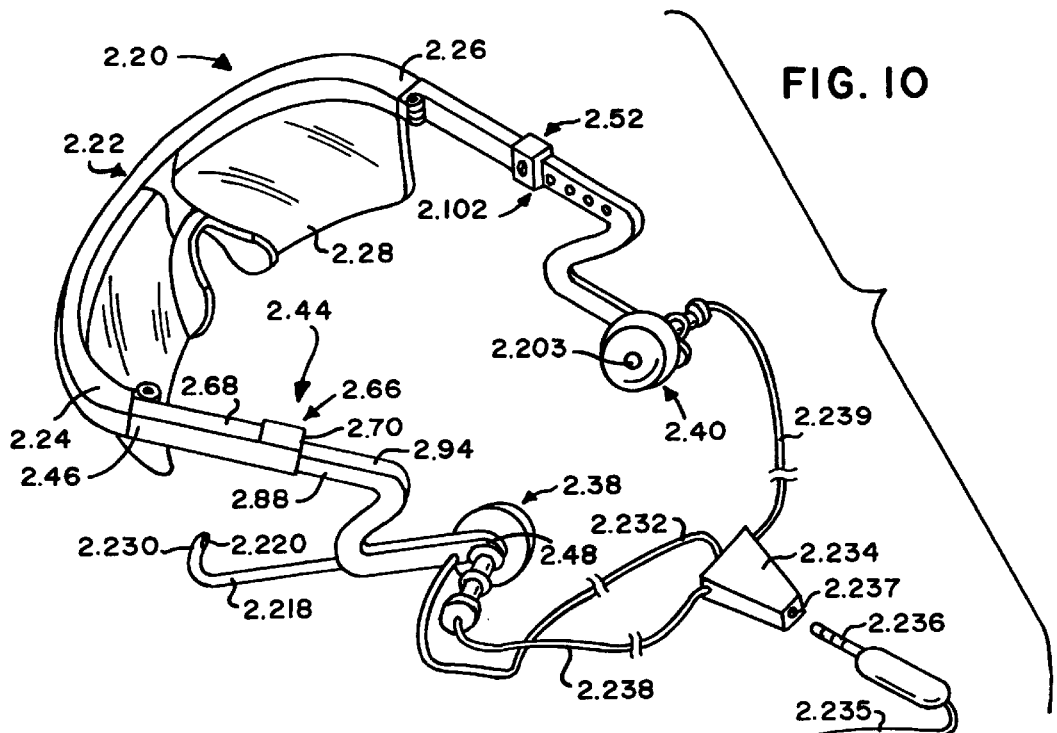
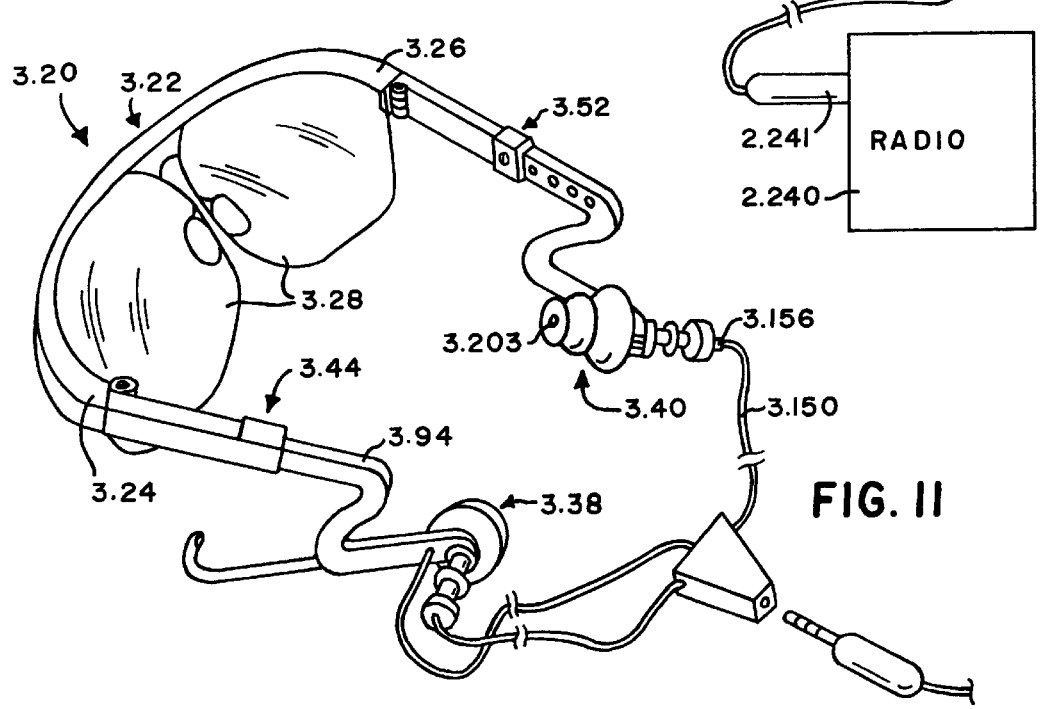

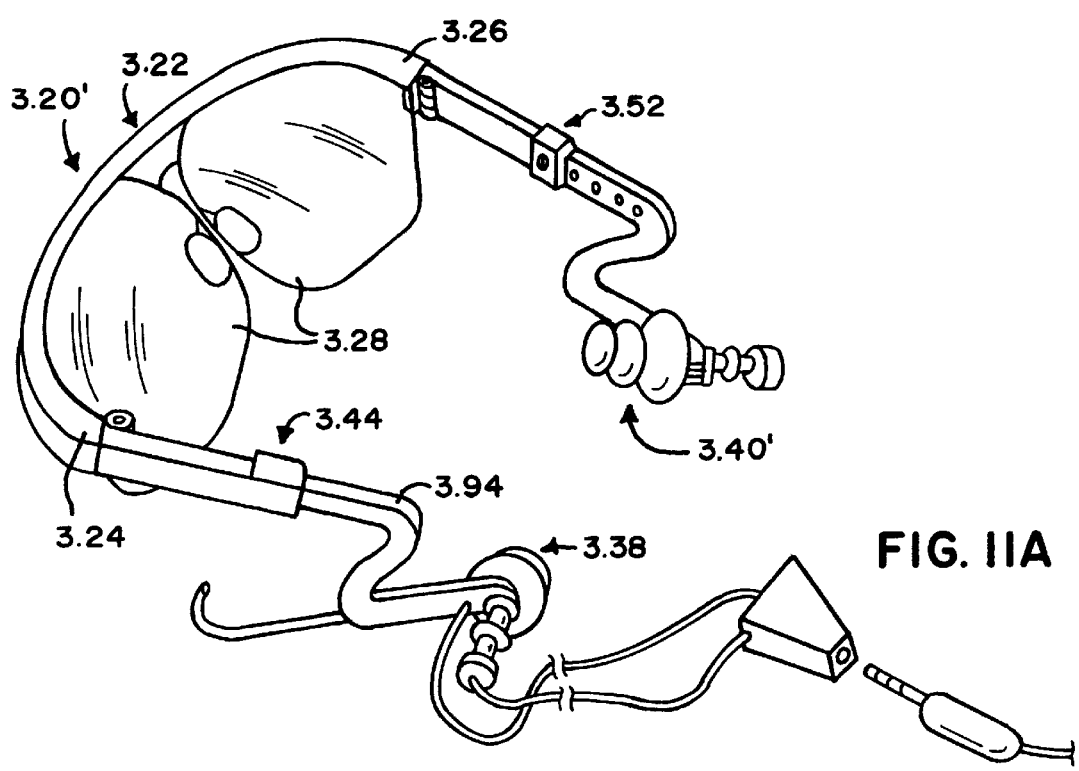
FIG. IIA

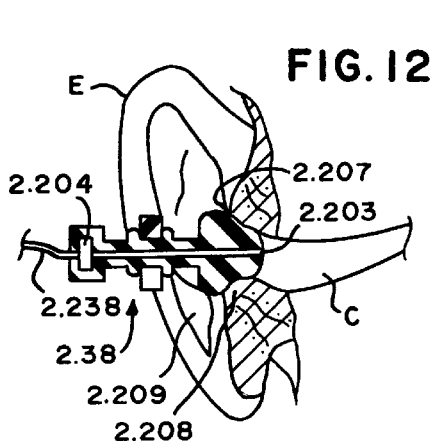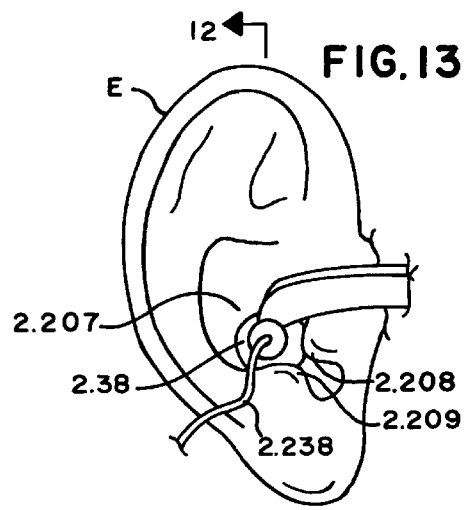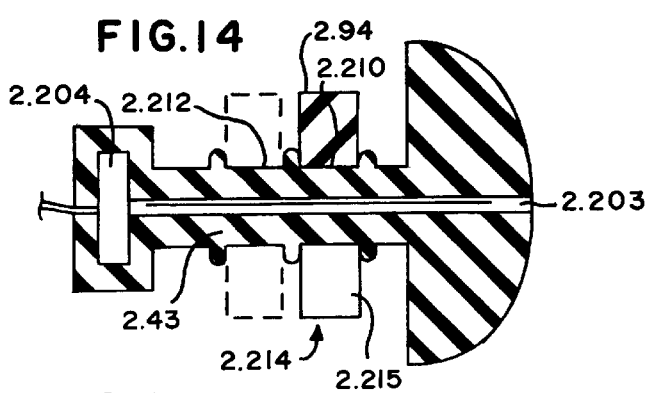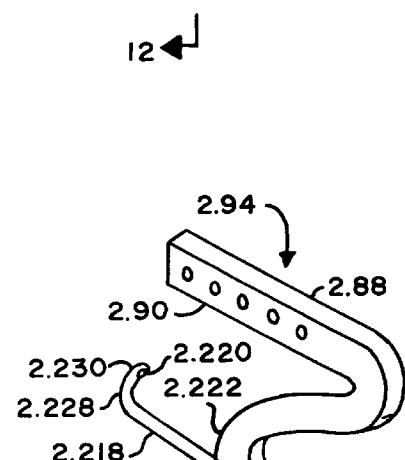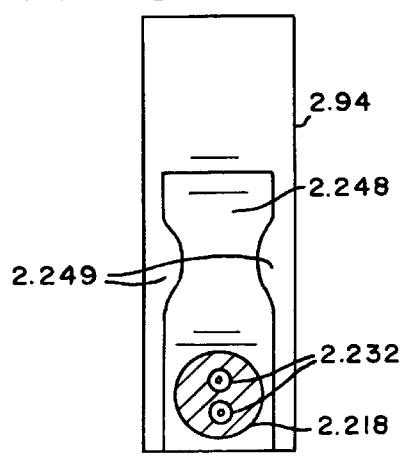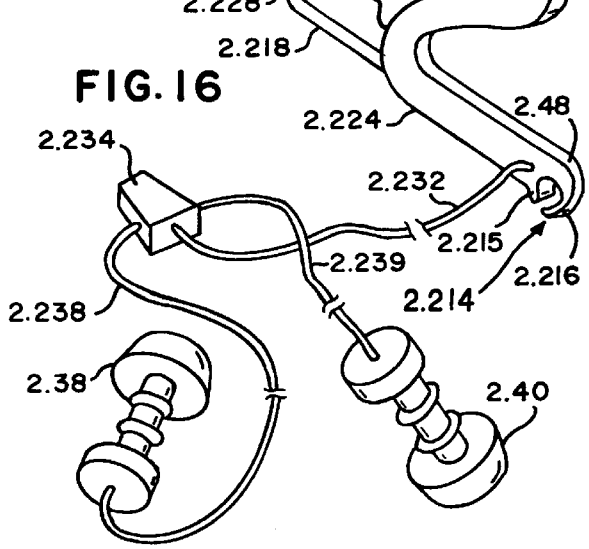

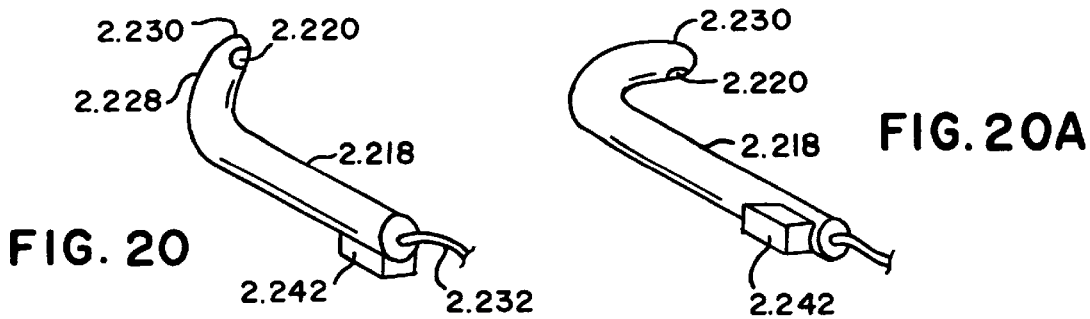
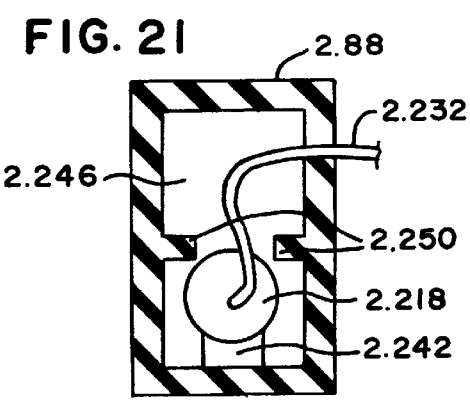
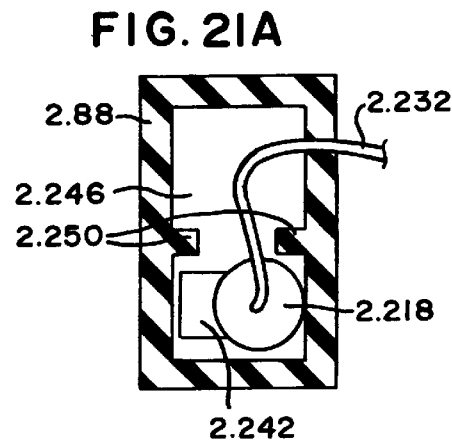
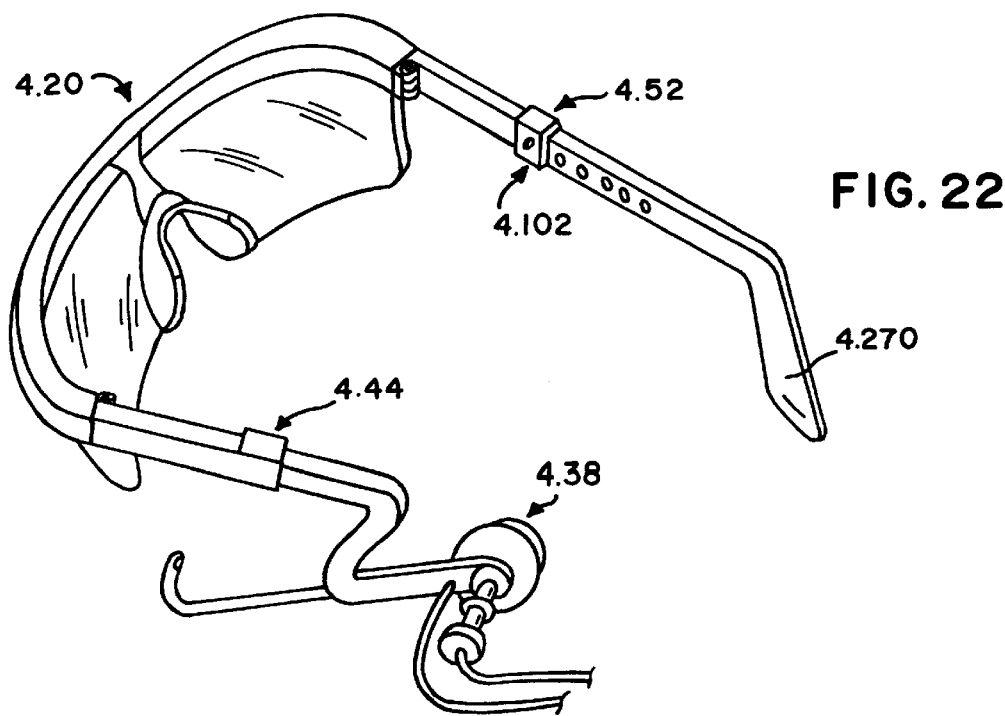

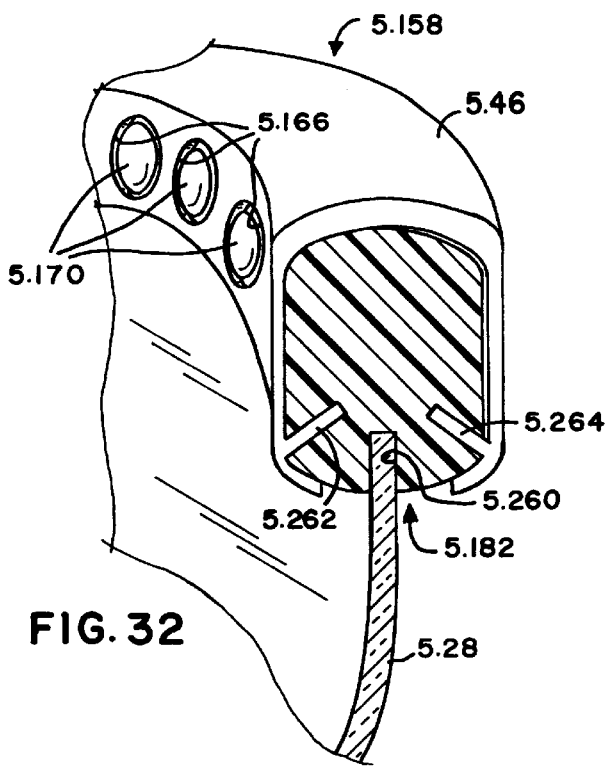
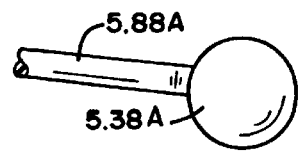
FIG. 35
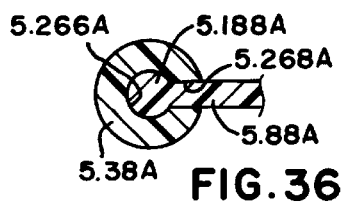
FIG. 36
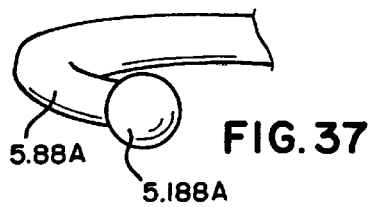
FIG. 37
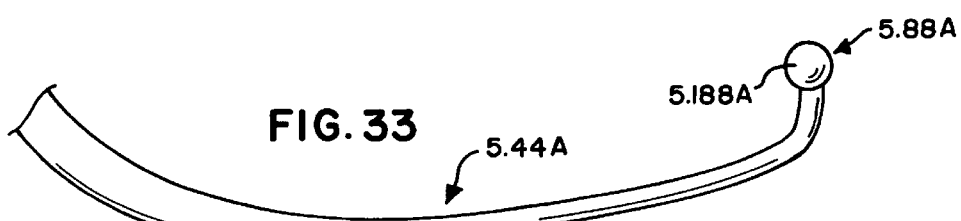
FIG. 33
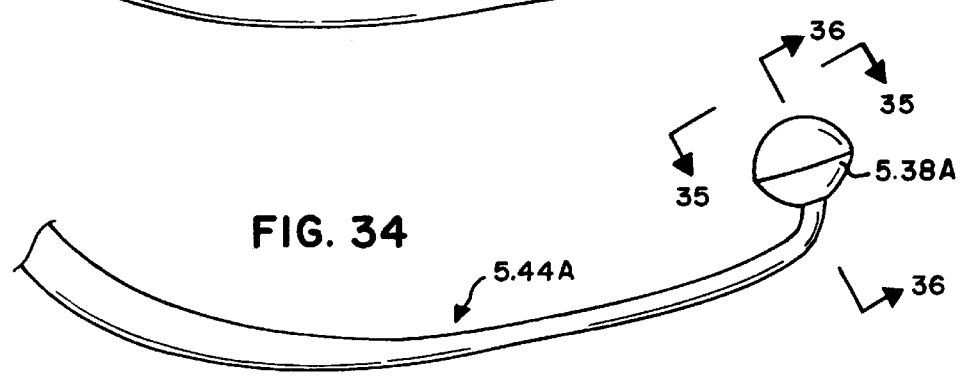
FIG. 34
FIG. 32

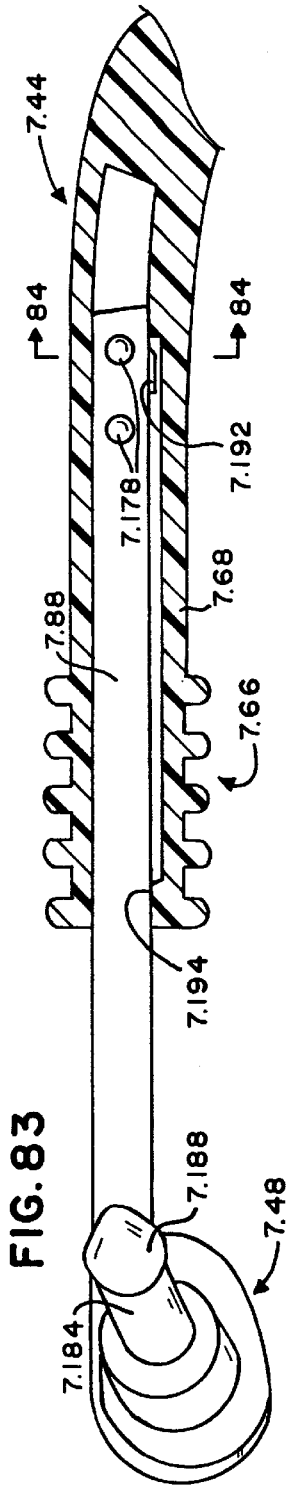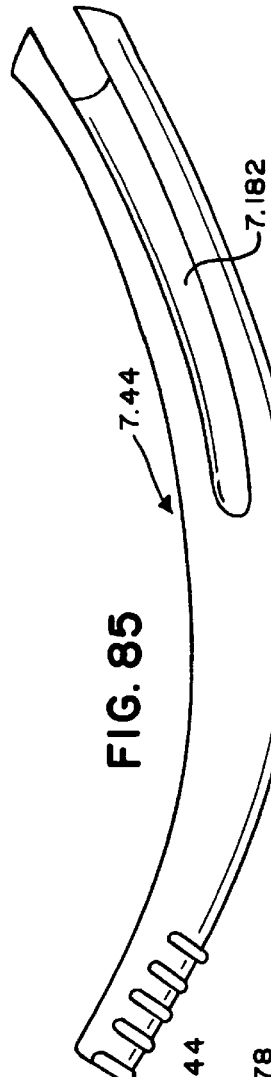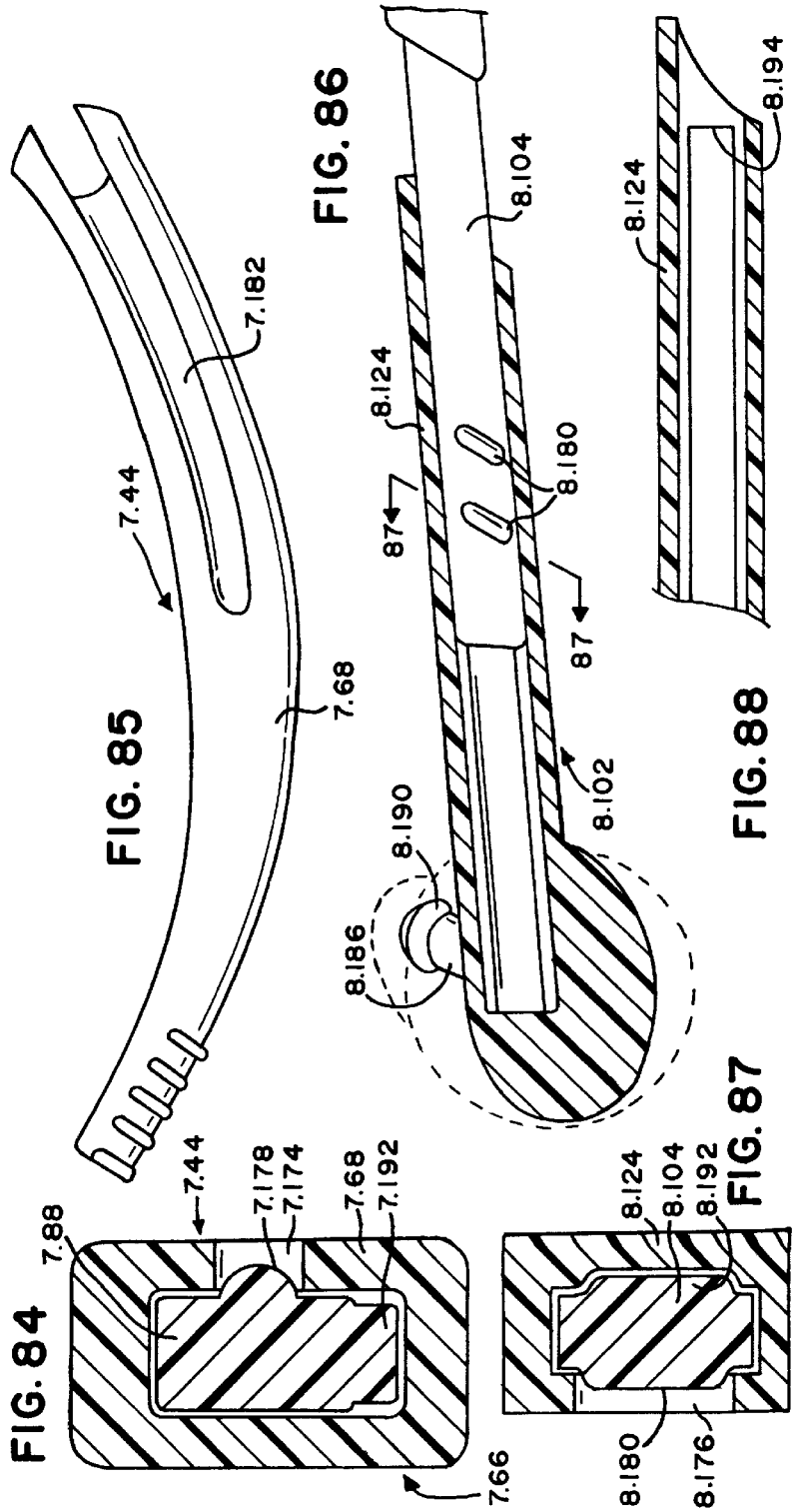

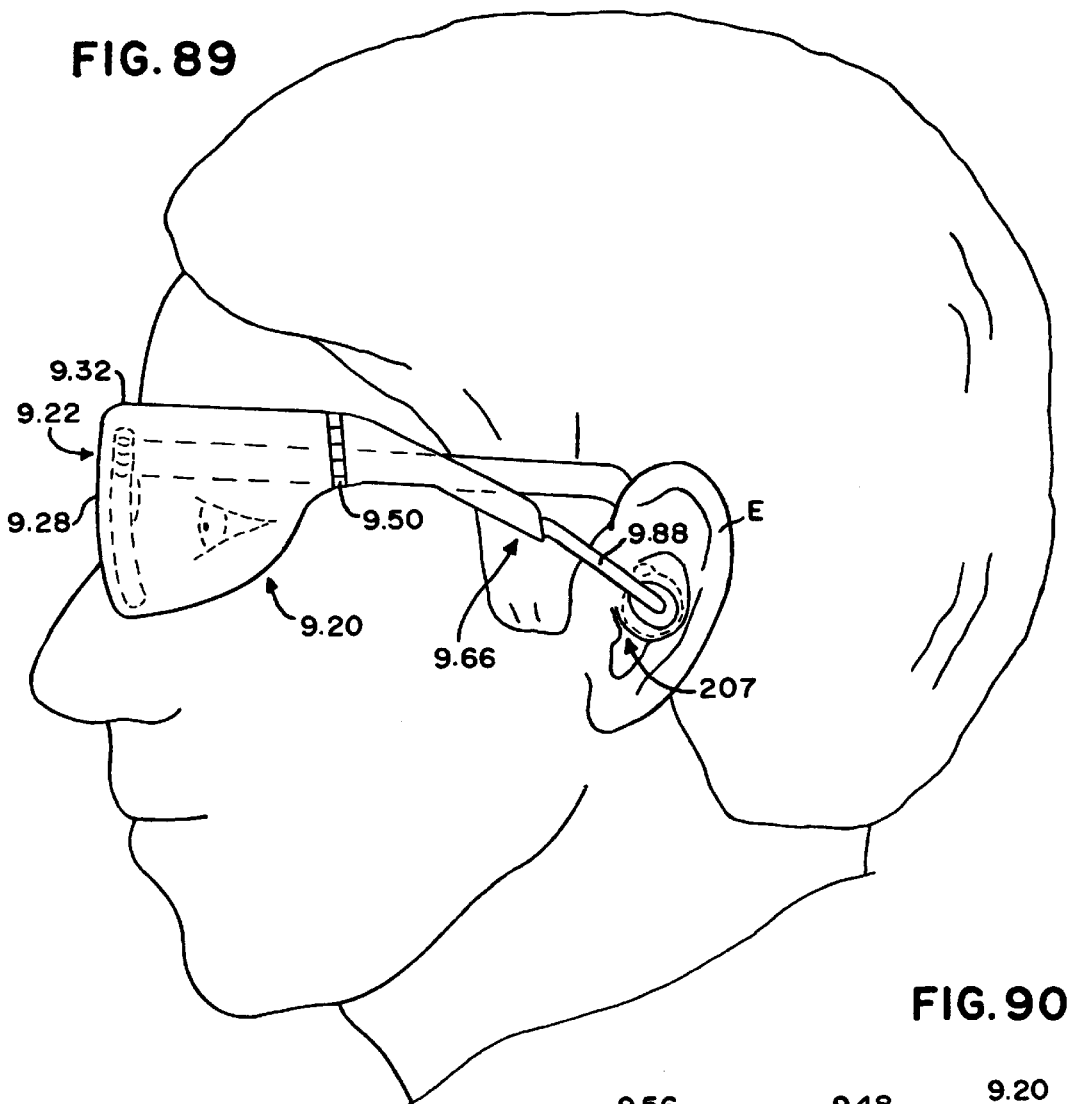
FIG. 89
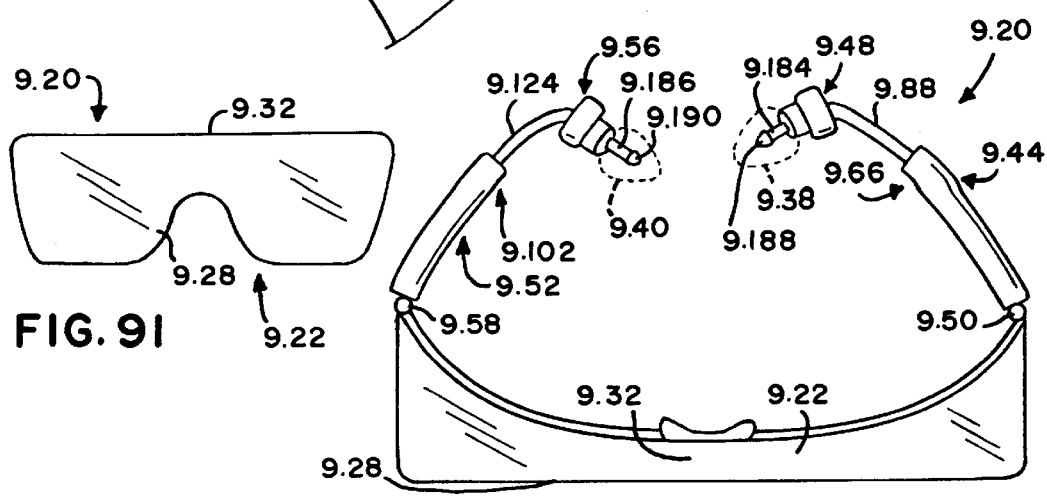
FIG. 90
FIG. 91

EYEWEAR SUPPORTED BY A WEARER'S CONCHA OF AN EAR

CROSS REFERENCE TO RELATED APPLICATIONS

This application is a continuation-in-part of U.S. patent application Ser. No. 09/114,391 now abandoned, entitled "EYEWEAR AND AUDIO APPARATUS", filed Jul. 13, 1998, now hereby fully incorporated by reference herein, which itself was a continuation-in-part of U.S. patent application Ser. No. 08/870,433, entitled "EYESIGHT PROTECTION APPARATUS WITH ATTACHED EARPLUGS" (as amended), filed Jun. 6, 1997, now issued as U.S. Pat. No. 5,781,272 on Jul. 14, 1998, now hereby fully incorporated by reference herein. This application is also a continuation-in-part of U.S. Design patent application No. 29/104,345, entitled "EYEWEAR", filed May 3, 1999 now Design 426,845, now hereby fully incorporated by reference herein, and is further a continuation-in-part of co-pending U.S. Provisional Patent application Ser. No. 60/132,205, entitled "EYEWEAR WITH HEARING PROTECTION", filed May 3, 1999, now hereby fully incorporated by reference herein.

STATEMENT REGARDING FEDERALLY SPONSORED RESEARCH OR DEVELOPMENT

Not applicable.

REFERENCE TO A "MICROFICHE APPENDIX"

Not applicable.

BACKGROUND OF THE INVENTION

1. Field of the Invention

The present invention relates, in general, to protective eyewear and protective earwear devices, and in particular, to protective eyewear with combined protective earpieces, as well as to protective eyewear devices having attached audio capability.

2. Description of the Prior Art

It is often desired to protect a person's eyes from being injured by flying debris at the workplace and to protect a person's hearing from being injured due to excessive noise at the workplace. Well-known solutions for this problem include providing separate safety glasses and earplugs. A problem occurs because a person, such as an employee, may use only one protective device when, in fact, both protective eyewear and protective earpieces are needed for proper protection in the work environment. Other well-known solutions for this problem include providing safety glasses with earplugs attached to the safety glasses in some manner, such as by cords. The problem with these solutions is that a user may wear the safety glasses without using the earplugs, thereby causing damage to his or her hearing. As an example, Leight, U.S. Pat. No. 3,943,925, provides a hearing protector assembly that attaches to the temples of safety glasses, in which the temples of the glasses are supported over the ear. The protector assembly can be completely removed from the safety glasses, and, in addition, the assembly includes a brake that can hold the earplug away from the ear, thereby allowing the safety glasses to be worn without utilizing the hearing protector.

It is therefore desirable to have an eyesight and hearing safety device that, by design, requires the wearer to use both the safety glasses and earplugs simultaneously, thereby ensuring that the eyes and the hearing of the wearer are protected from harm.

It is also sometimes desired to listen to an audio device such as a radio, cassette tape player, or compact disc player while wearing protective or corrective eyewear, and there are occasions, such as, for example, on the floor of a large factory, where it is desirable to have the added convenience of a microphone along with audio reception capability so as to permit two-way communication. Well-known solutions to this problem include the use of an audio headset with the headset possibly having a microphone, and often such headsets are worn by those who wear glasses. The problem with prior art solutions is the inconvenience of having to put on or take off the glasses and headset with microphone separately and then having to reposition both devices when either is disturbed.

Rickards, U.S. Pat. No. 5,717,479, discloses a pair of safety glasses having a boom microphone and having disposable speaker earplugs attached by a sound tube or wire to a radio receiver mounted to the safety glasses. However, safety glasses of the Rickards device are supported over the ears of the wearer by earloops on the rear of the temples, thereby allowing the speaker earplugs to be removed while the safety glasses are worn and thereby removing any protection to the wearer's hearing. Such prior art is undesirable because the wearer's ears can become completely exposed and unblocked while wearing the glasses, and wearing of the earpieces thus cannot be compelled.

It is also known to have eyeglasses that incorporate a hearing aid into the frame of the eyeglasses. However, such solutions are not capable of attachment to a two-way communications device, such as a radio, and such hearing aid glasses do not incorporate a microphone. Additionally, such hearing aid glasses do not provide protection from further hearing loss.

It is further desirable that the eye protection lenses or shield of the eyewear may be tinted or have a polarizing coating for serving as sunglasses, thereby protecting the eyes from harmful glare or rays from the sun when outdoors, and that such eyewear be provided with audio earpieces and/or microphones.

BRIEF SUMMARY OF THE INVENTION

The present invention has many embodiments and improvements that accompany each of the succession of embodiments, but all embodiments are eyewear having a front transparent panel or single or dual lens (which may be clear or tinted for sunlight and glare protection and/or for eye protection during welding) that is supported on a wearer's head by a nose bridge and by at least one earpiece or earplug that is received into the concha of the wearer's ear and/or into the ear canal. The earpiece or earplug is attached to a rear end of its respective temple of the eyewear, and, unlike prior art, the temple for the earpiece or earplug is not supported over the wearer's ear, being only supported by the earpiece or earplug received into the wearer's ear without having any corresponding temple portion extending over the wearer's ear. Preferably both temples are only supported by their respective rear earpiece or earplug received into the wearer's respective ear, but some embodiments of the invention have a first temple on one side of the eyewear with a rear earplug or earpiece supported only by the receipt of the earpiece or earplug into the wearer's ear and, on the other side of the eyewear, have a well-known conventional second temple supported over the wearer's ear, without an earpiece or earplug.

The earpieces of some embodiments sealingly and protectively plug the ear canal of the wearer and thus protect the wearer's hearing.

Some embodiments of the present invention have a microphone, whether as a boom-mounted microphone or an ear microphone; some embodiments of the present invention have audio earpieces for reproducing sound from an audio signal source; and some embodiments of the present invention have both a microphone and audio earpieces for providing two-way communication for the wearer. The audio earpieces may either sealingly and protectively plug the wearer's ear canal or may rest in the wearer's concha and on the outer ear. Various earpiece attachment means are provided for attaching the earpieces and earplugs to the temples of the eyewear.

The temples may have sliding length adjustment means and may have sliding spread adjustment means to selectively adjust for various-sized wearers' heads. The temples of the various embodiments of the invention are substantially shape-retaining, as contrasted to string, cord, or length-elastic bands. The eyewear is constructed so that the temples preferably exert an inward pressure on the earpieces and earplugs so as to retain the eyewear on the wearer's head during physical activity.

It is an object of the present invention to provide eyewear and audio apparatus that requires a wearer to use both eyesight and hearing protection while wearing the apparatus.

It is a further object of the present invention to provide an eyesight and hearing safety apparatus which can be firmly secured in place so that the human being can be very physically active while wearing the apparatus.

It is an object of the present invention to provide eyewear (sunglasses or corrective lenses) and audio (from a separate cellular telephone, radio, tape cassette, compact disc player, or two-way radio), with a microphone when appropriate, for both recreational and business use.

It is an object of the present invention to provide eyewear in which at least one temple is, and preferably both temples are, supported from the wearer's respective ear only by the earpiece or earplug attached to the rear of the temple, without having a temple portion extending over that respective ear of the wearer.

BRIEF DESCRIPTION OF THE SEVERAL VIEWS OF THE DRAWING

FIG. 3 is a perspective view of a portion of a first temple and of a first side transparent panel of the first embodiment of the present invention.

FIG. 4 is a different perspective view of the portion of the first temple shown in FIG. 3.

FIG. 5 is a perspective view of another portion of the first temple shown adjusted to a first vertical position.

FIG. 5A is a perspective view of the other portion of the first temple shown adjusted to a second vertical position.

FIG. 6 is an enlarged perspective view of a first and a second earplug and suspending means.

FIG. 10 is a perspective view of a second preferred embodiment of the present invention with tinted lenses, two earphones, and an extended microphone boom.

FIG. 11 is a perspective view of a third preferred embodiment of the present invention with corrective lenses, one earphone, one earplug-type earphone, and an extended microphone boom.

FIG. 11A is a perspective view of a variation of the third preferred embodiment of the present invention having corrective lenses, one earphone, one earplug, and an extended microphone boom.

FIG. 12 is a sectional view showing the earphone of the second and third embodiments in a user's ear.

FIG. 13 is a side view showing the earphone of the second and third embodiments in a user's ear.

FIG. 14 is a sectional view of the earphone of the second and third embodiments, taken along a diameter of the earphone, and showing the various adjustable positions of the temple gripping portion.

FIG. 15 is an end view showing the recess for receiving the retracted microphone boom, taken substantially along the line 15—15 shown in FIG. 17.

FIG. 16 is a perspective view of a portion of the adjustable temple of the second and third embodiments, showing the microphone boom and the earphones.

FIG. 20 is a perspective view of the microphone boom showing its securing mechanism in an unsecured first position.

FIG. 20A is a perspective view of the microphone boom showing its securing mechanism rotated into a secured second position.

FIG. 21 is a transverse sectional view of the rear portion of the first temple showing the microphone boom's securing mechanism in the unsecured first position, taken substantially along the line 21—21 shown in FIG. 17.

FIG. 21A is a transverse sectional view of the rear portion of the first temple, similar to FIG. 21, but showing the microphone boom's securing mechanism rotated into the secured second position.

FIG. 22 shows a fourth embodiment in which one temple hooks or loops over one of the wearer's ears.

FIG. 32 is a sectional view showing attachment of the front temple portion to the front browpiece of the fifth embodiment of the present invention so as to form the first temple spread-and-length adjustment means.

FIG. 33 is a top view of a first alternate temple for the fifth embodiment of the present invention with the earpiece removed.

FIG. 34 is a top view of the first alternate temple for the fifth embodiment of the present invention with the earpiece attached.

FIG. 35 is an end view showing attachment of an earpiece to the first alternate temple of the fifth embodiment of the present invention, taken substantially along the line 35—35 shown in FIG. 34.

FIG. 36 is a partial sectional view showing attachment of an earpiece to the first alternate temple of the fifth embodiment of the present invention, taken substantially along the line 36—36 shown in FIG. 34.

FIG. 37 is a perspective end view of the first alternate temple of FIG. 33, with the earpiece removed.

FIG. 42 is a sectional view showing a first embodiment of the earpiece mounting means with the earplug barb at a first angle.

FIG. 43 is a sectional view showing the first embodiment of the earpiece mounting means with the earplug barb at a second angle.

FIG. 44 is a perspective view showing the first embodiment of the earpiece mounting means separated from the temple of the fifth embodiment of the present invention.

FIG. 45 is a perspective view of a second embodiment of the earpiece mounting means.

FIG. 46 is a sectional view showing the inner groove for rotation of the earpiece mounting means within the rear of the temple of the fifth embodiment of the present invention.

FIG. 47 shows a comfort plug after removal from the rear of the temple of the fifth embodiment of the present invention.

FIG. 48 is a sectional view showing the comfort plug of FIG. 47 as inserted into the rear of the temple of the fifth embodiment of the present invention.

FIG. 83 is a partial sectional view of the rear of the temple of the seventh embodiment of the present invention, showing the temple length adjustment means.

FIG. 84 is a transverse sectional view of the temple of the seventh embodiment of the present invention, taken substantially along the line 84—84 shown in FIG. 83.

FIG. 85 is a bottom view of the temple as removed from the seventh embodiment of the present invention.

FIG. 86 is a partial sectional view of the rear of the temple of the eighth embodiment of the present invention, showing the temple length adjustment means.

FIG. 87 is a transverse sectional view of the temple of the eighth embodiment of the present invention, taken substantially along the line 87—87 shown in FIG. 86.

FIG. 88 is a portion of the transverse sectional view shown in FIG. 87 of the temple of the eighth embodiment of the present invention, with the front temple portion removed to show features hidden in FIG. 87.

FIG. 89 is a side view showing a wearer wearing a ninth "overglasses" embodiment of the present invention. The view from the other side is substantially a mirror image.

FIG. 90 is a top view of the ninth embodiment of the present invention.

FIG. 91 is a front view of the ninth embodiment of the present invention.

DETAILED DESCRIPTION OF THE INVENTION

The present invention is a related improvement of the invention described in co-pending U.S. patent application Ser. No. 09/114,391, entitled "EYEWEAR AND AUDIO APPARATUS", filed Jul. 13, 1998, now hereby fully incorporated by reference herein, which itself was a continuation-in-part of U.S. patent appplication Ser. No. 08/870,433, entitled "EYESIGHT PROTECTION APPARATUS WITH ATTACHED EARPLUGS" (as amended), filed Jun. 6, 1997, now issued as U.S. Pat. No. 5,781,272 on Jul. 14, 1998, now hereby fully incorporated by reference herein. All embodiments have many common structural similarities, as will be explained and disclosed herein. All embodiments are eyewear having a front transparent panel or single or dual lens (clear or tinted for sunlight and glare protection and/or for eye protection during welding) that is supported on a wearer's head by a nose bridge and by at least one earpiece or earplug that is received into the concha of the wearer's ear and/or into the ear canal. The earpiece or earplug is attached to a rear end of its respective temple of the eyewear, and, unlike prior art, the temple for the earpiece or earplug is not supported over the wearer's ear, being only supported by the earpiece or earplug received into the wearer's ear without having any corresponding temple portion extending over the wearer's ear.

Figure 68:
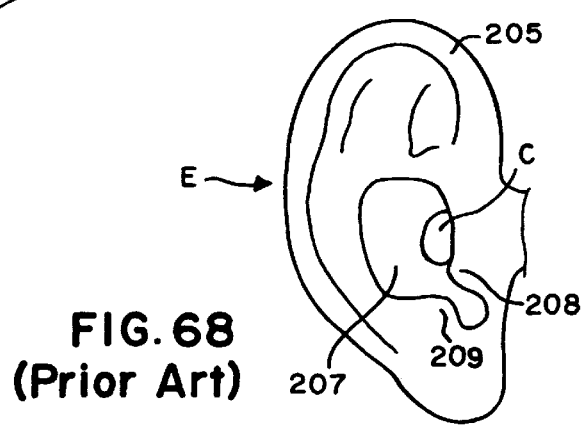
FIG. 68 is a side view of a well-known human ear showing the parts thereof.
Figure 69:
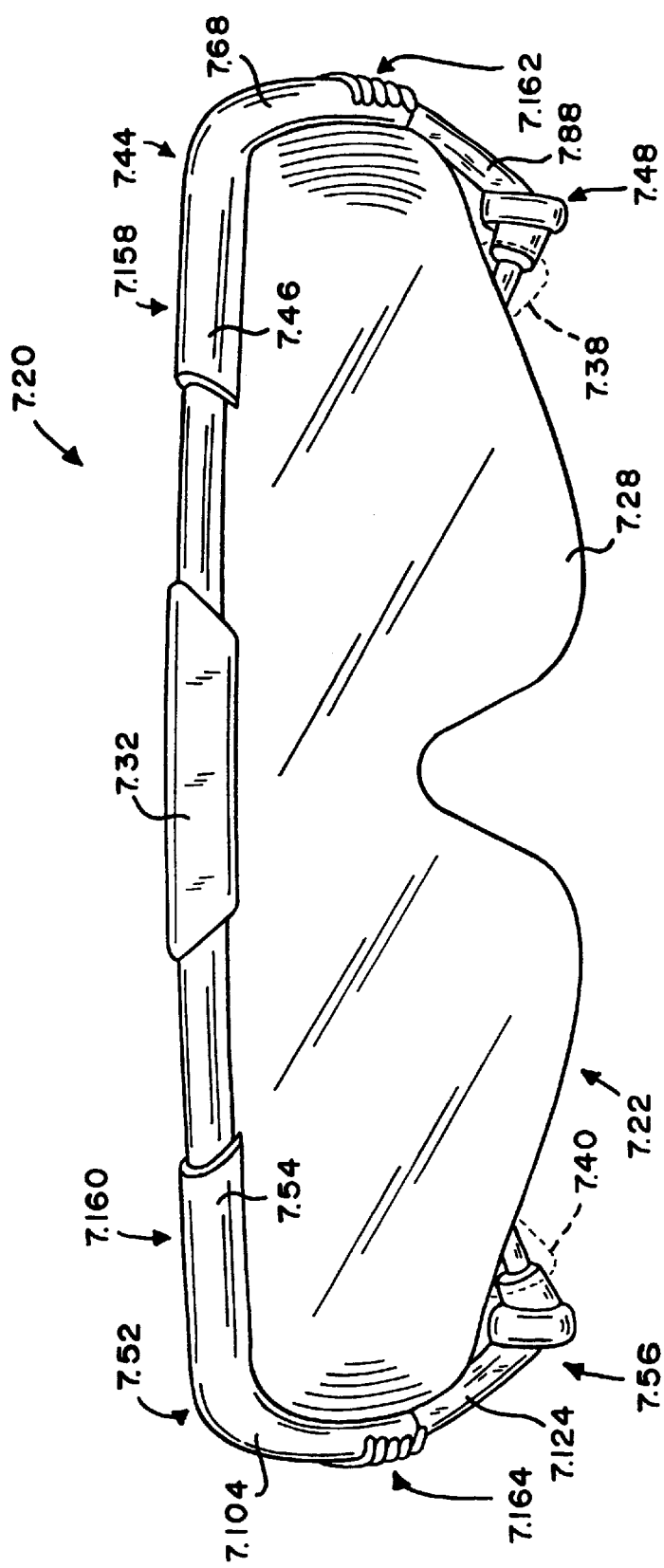
FIG. 69 is a front view of a seventh embodiment of the present invention with attached earplugs shown in dotted outline.
Figure 70:
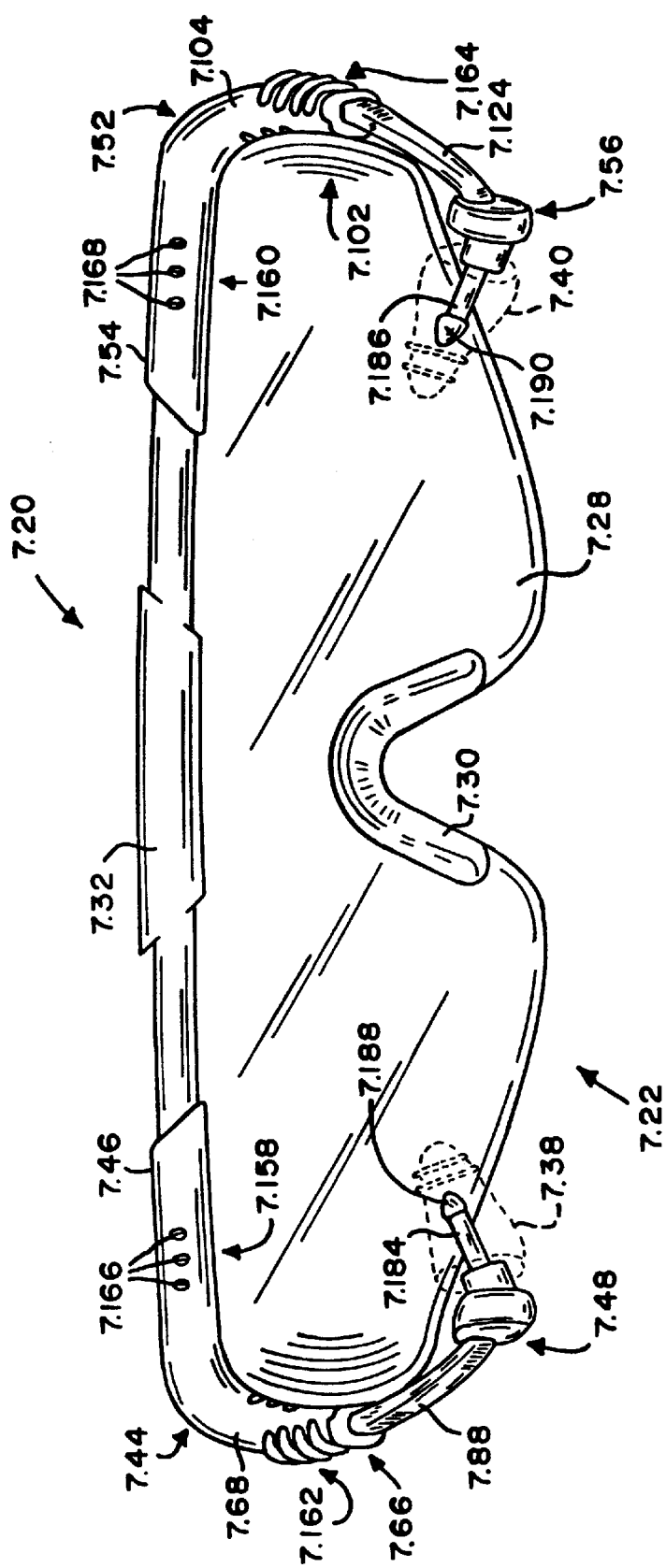
FIG. 70 is a rear view of the seventh embodiment of the present invention with attached earplugs shown in dotted outline.
Figure 71:
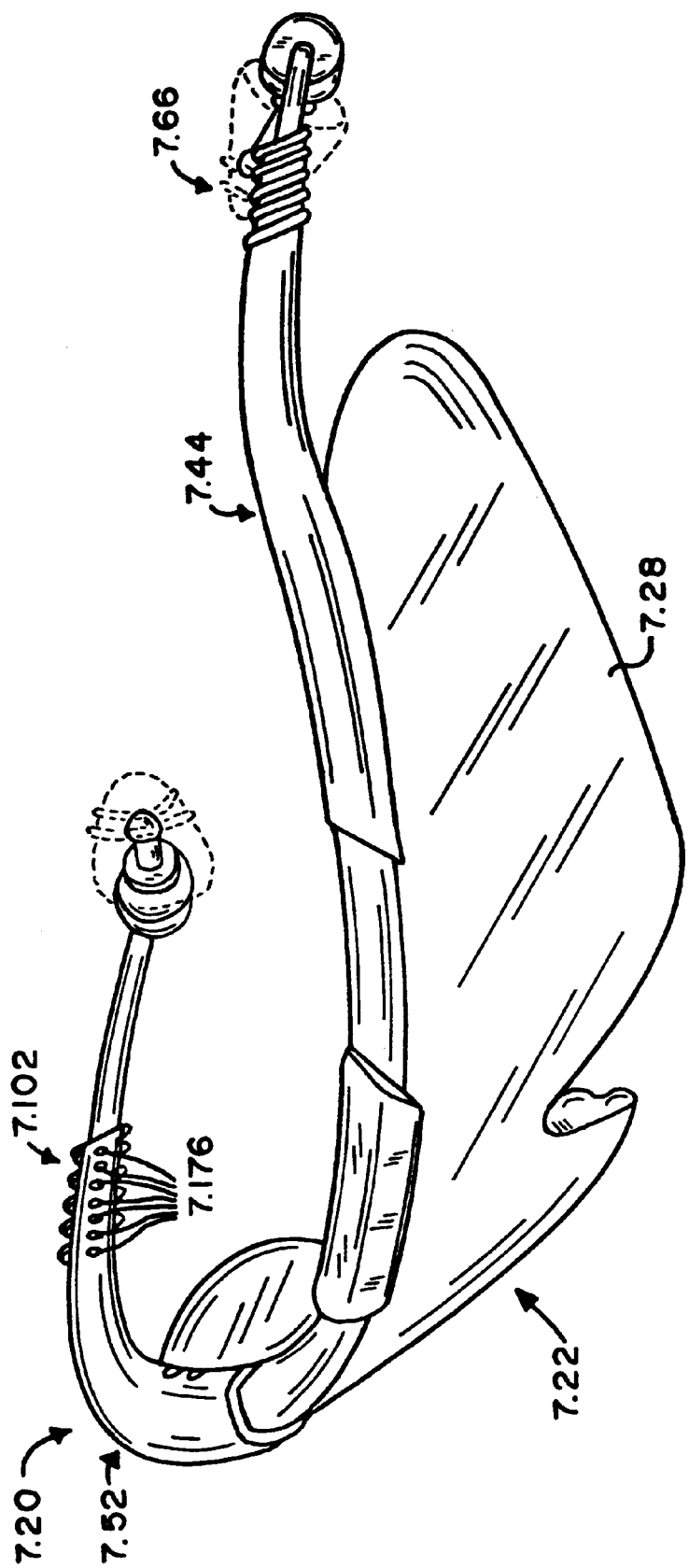
FIG. 71 is a perspective view of the seventh embodiment of the present invention from one side with attached earplugs shown in dotted outline.
Figure 72:
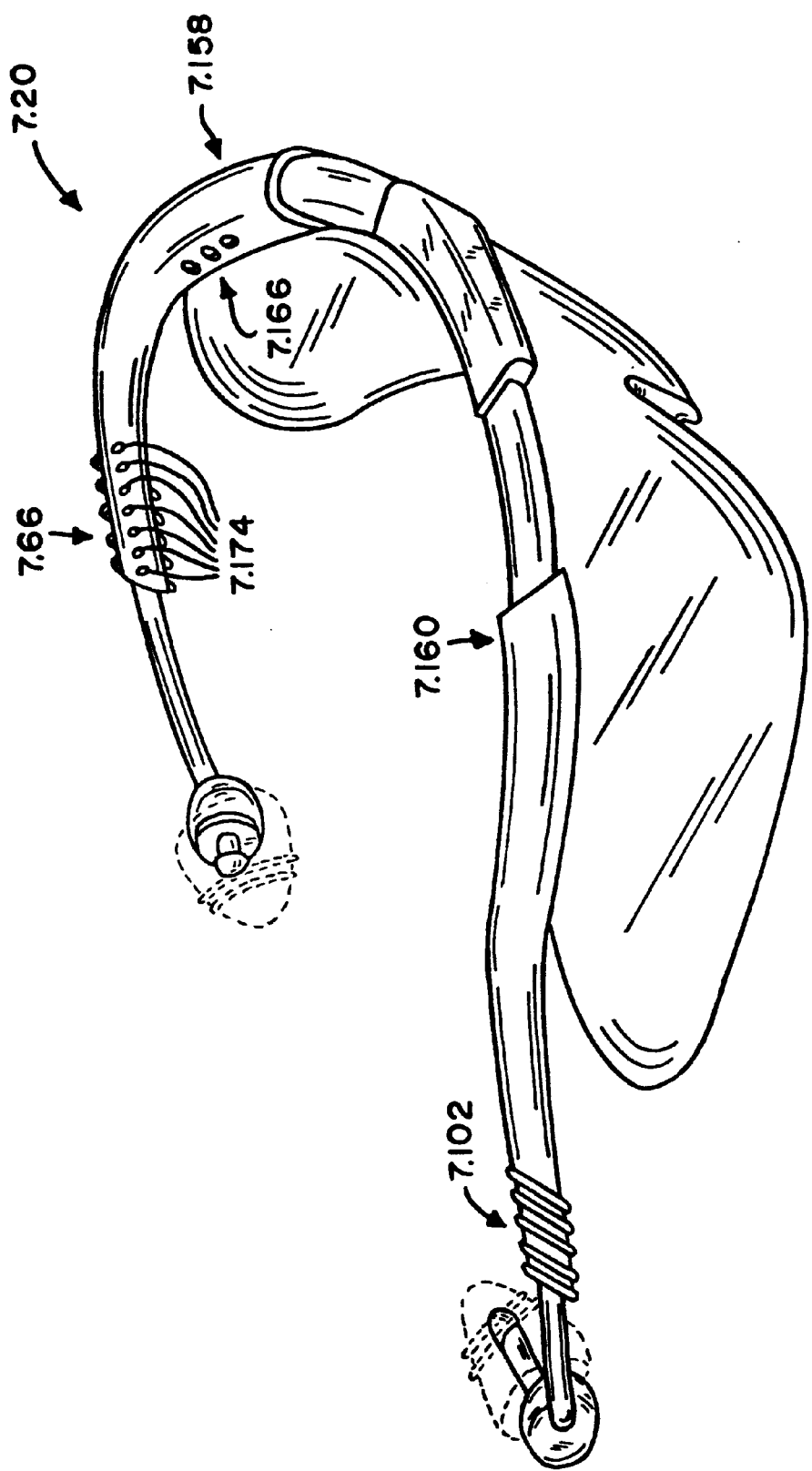
FIG. 72 is a perspective view of the seventh embodiment of the present invention from another side with attached earplugs shown in dotted outline.
Figure 73:
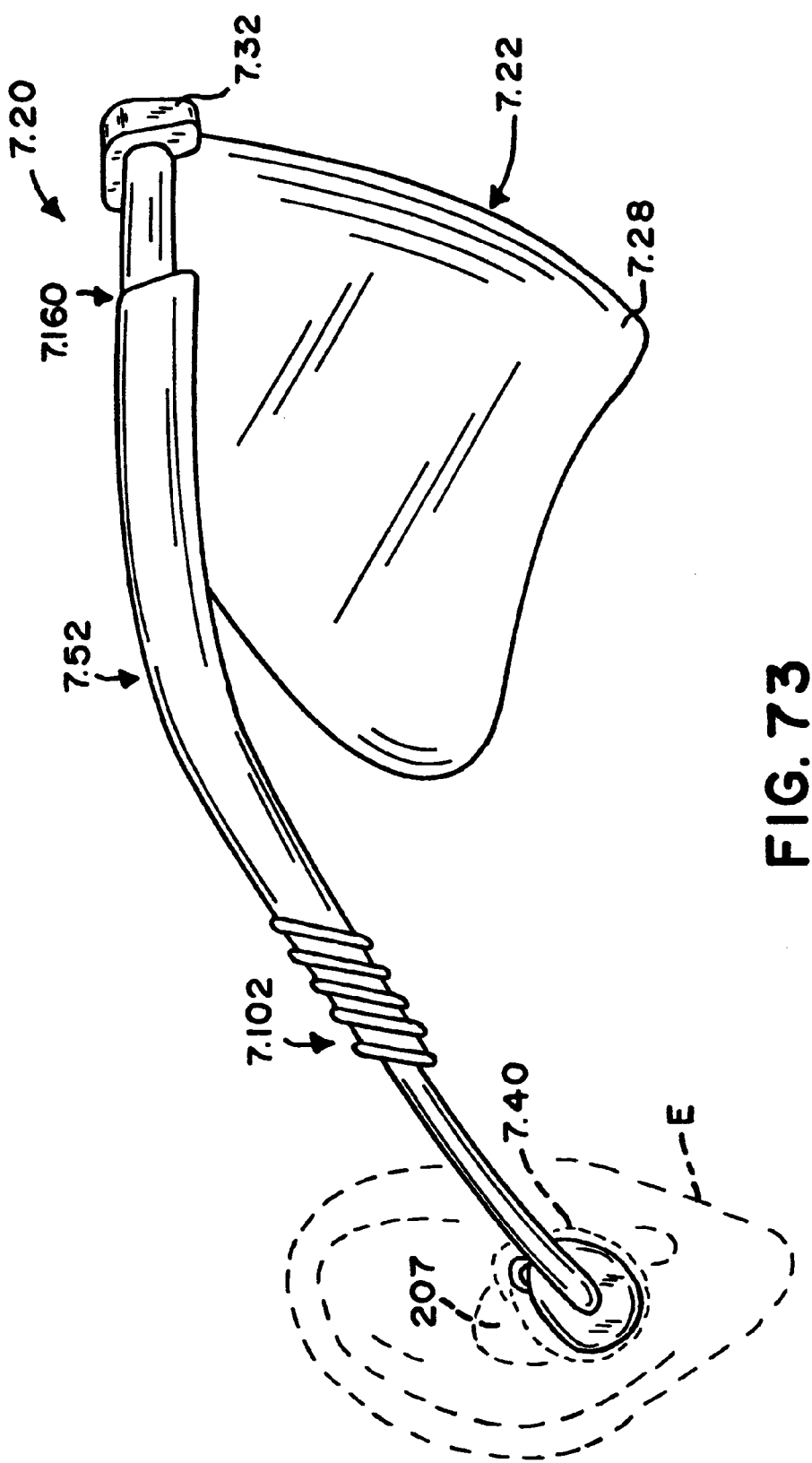
FIG. 73 is a side view of the seventh embodiment of the present invention, the view from the other side being a substantially similar mirror image, with attached earplugs shown in dotted outline.
Figure 74:
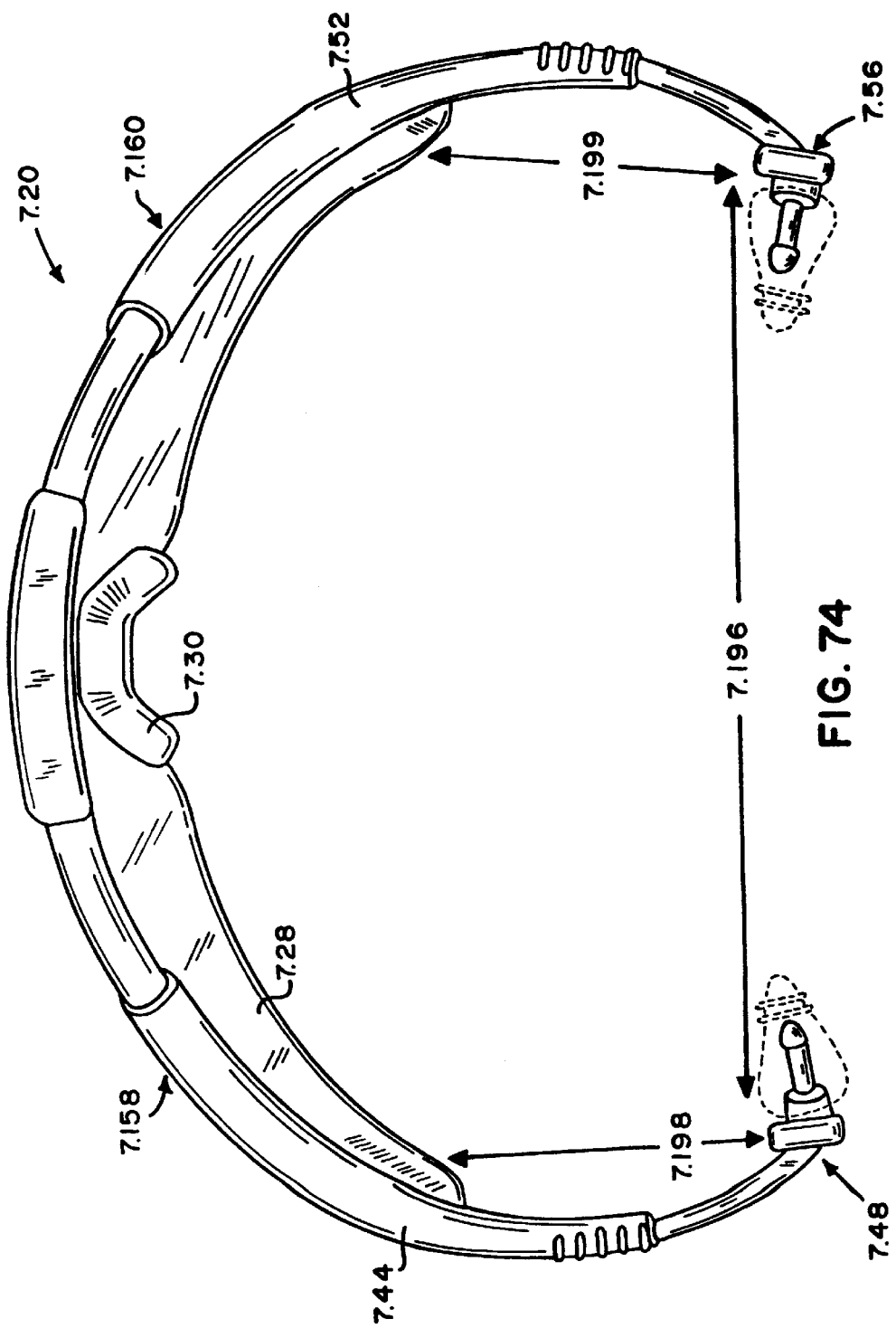
FIG. 74 is a top view of the seventh embodiment of the present invention with attached earplugs shown in dotted outline.
Figure 75:
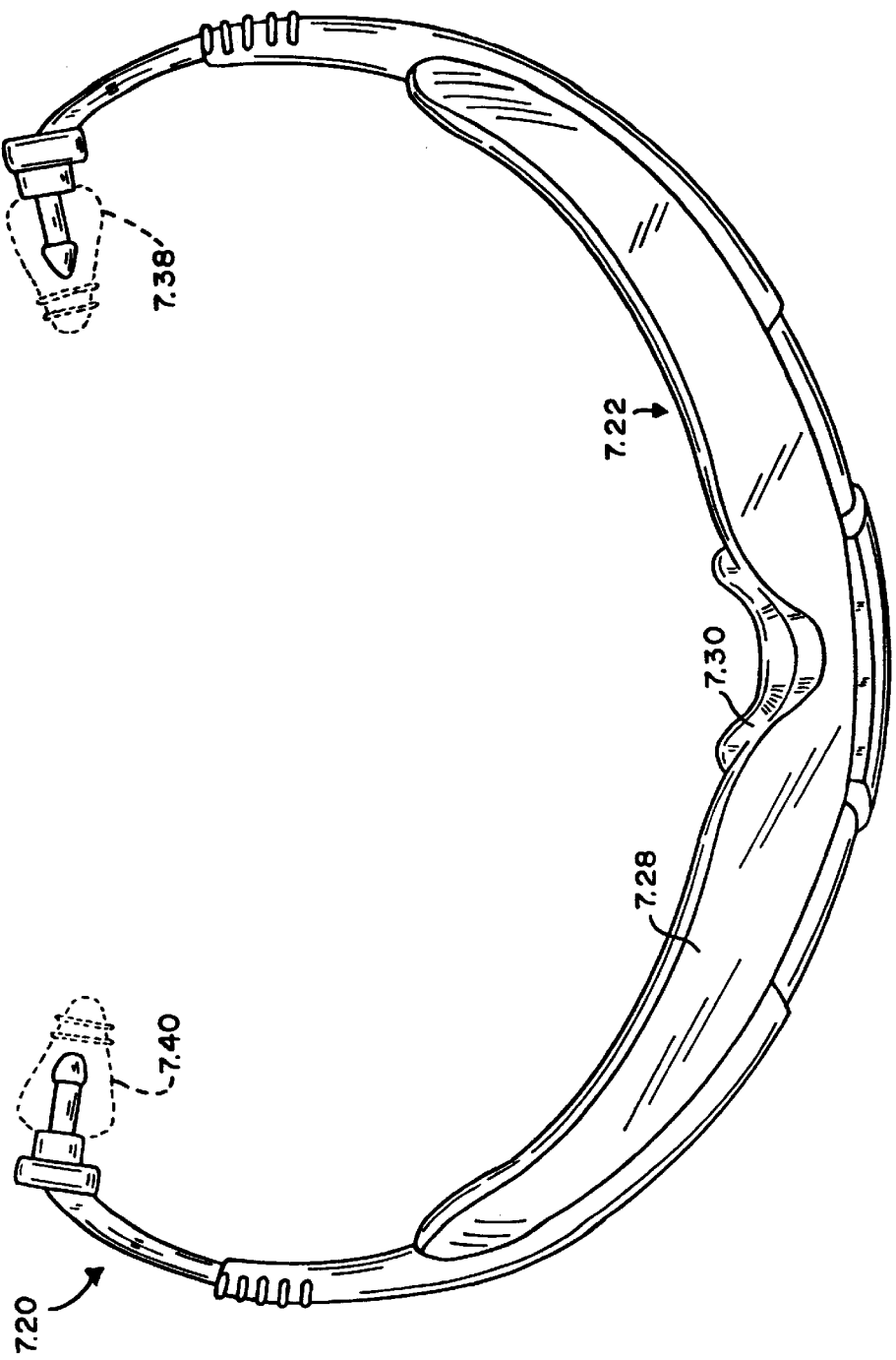
FIG. 75 is a bottom view of the seventh embodiment of the present invention with attached earplugs shown in dotted outline.
Figure 76:
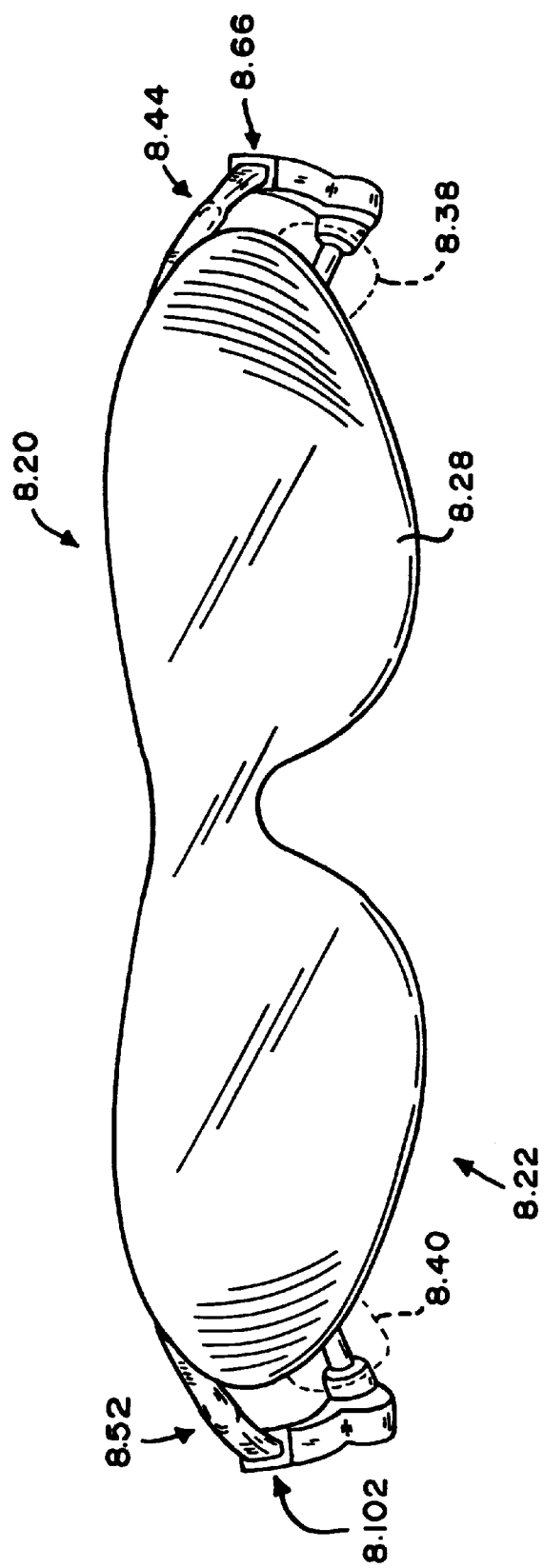
FIG. 76 is a front view of a eighth embodiment of the present invention with attached earplugs shown in dotted outline.
Figure 77:
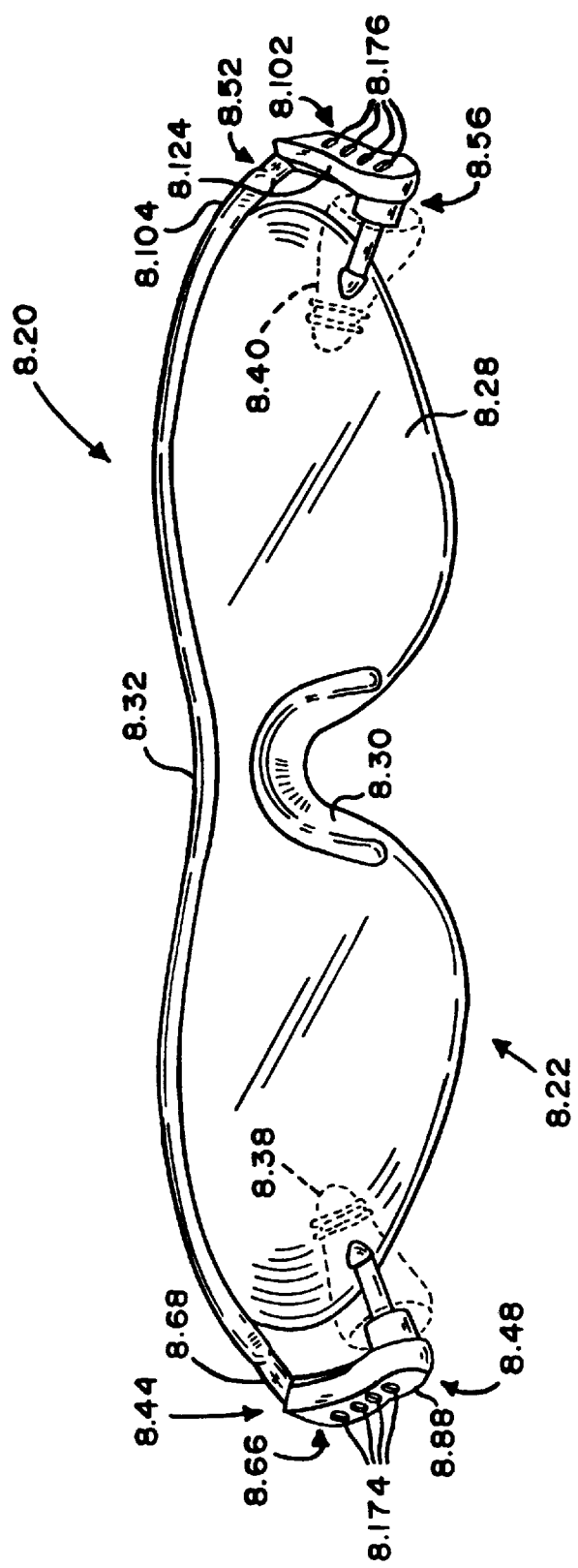
FIG. 77 is a rear view of the eighth embodiment of the present invention with attached earplugs shown in dotted outline.
Figure 78:
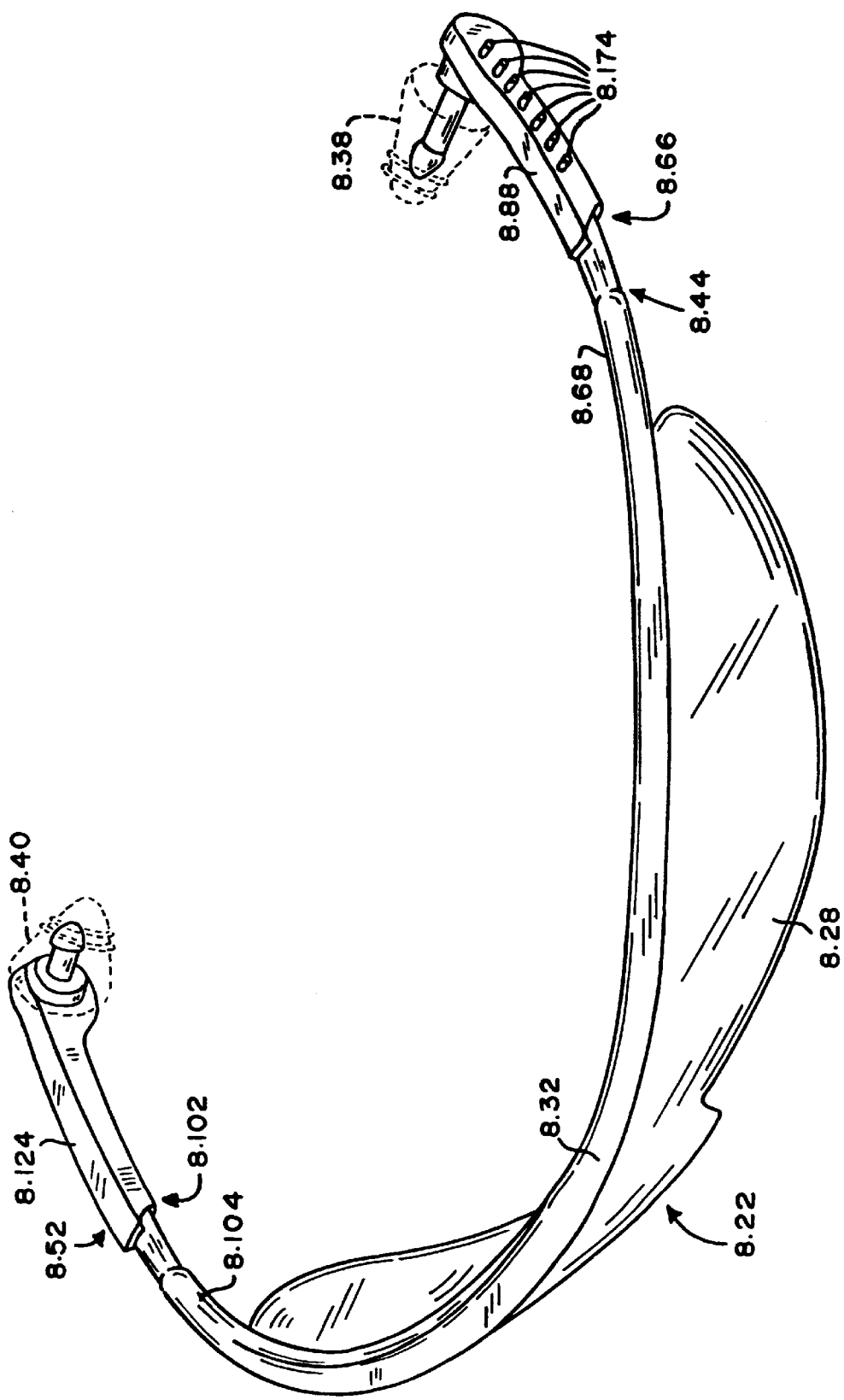
FIG. 78 is a perspective view of the eighth embodiment of the present invention from one side with attached earplugs shown in dotted outline. The similar perspective view from the other side is a mirror image.
Figure 79:
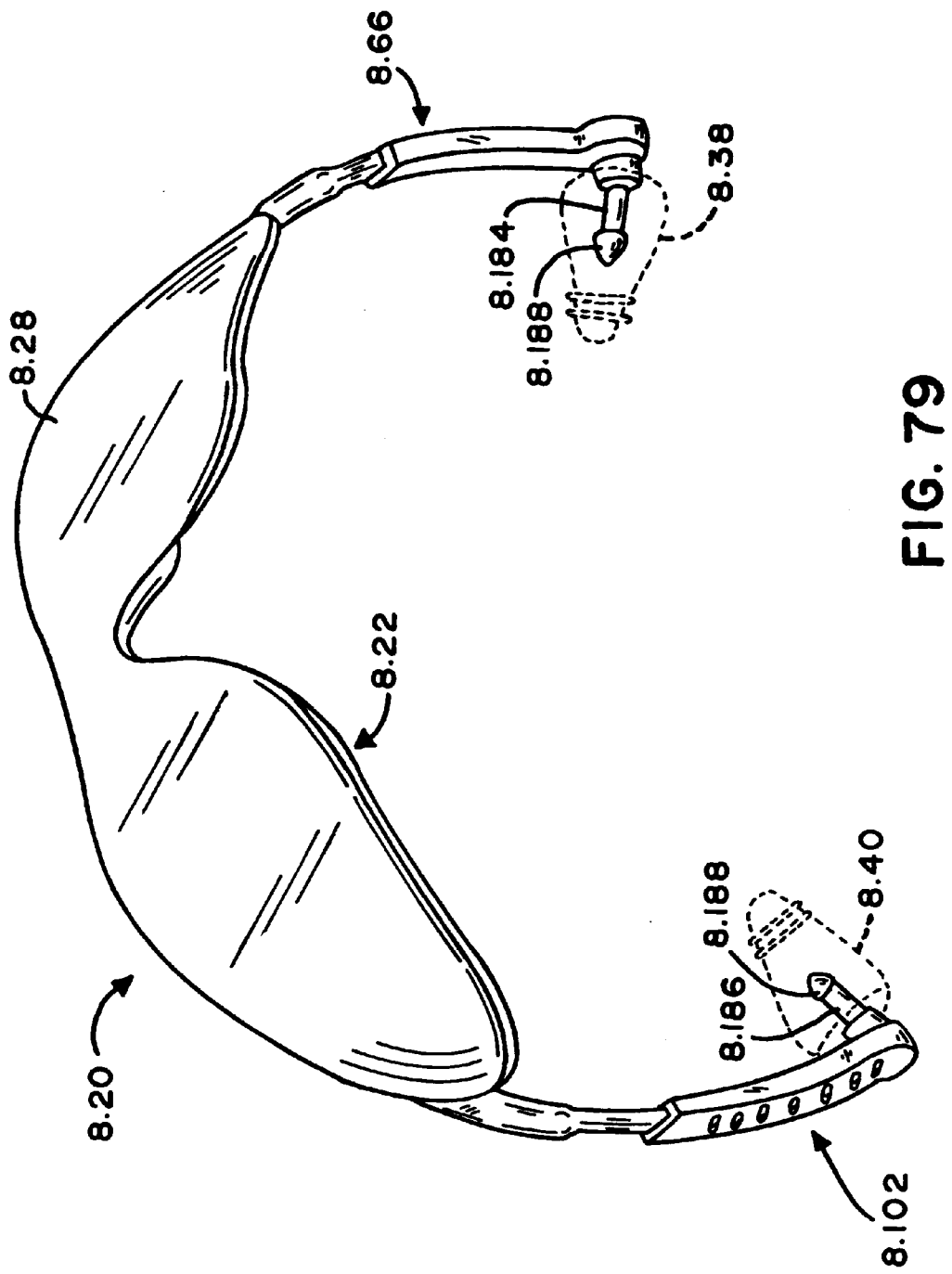
FIG. 79 is an underside perspective view of the eighth embodiment of the present invention with attached earplugs shown in dotted outline.
Figure 80:
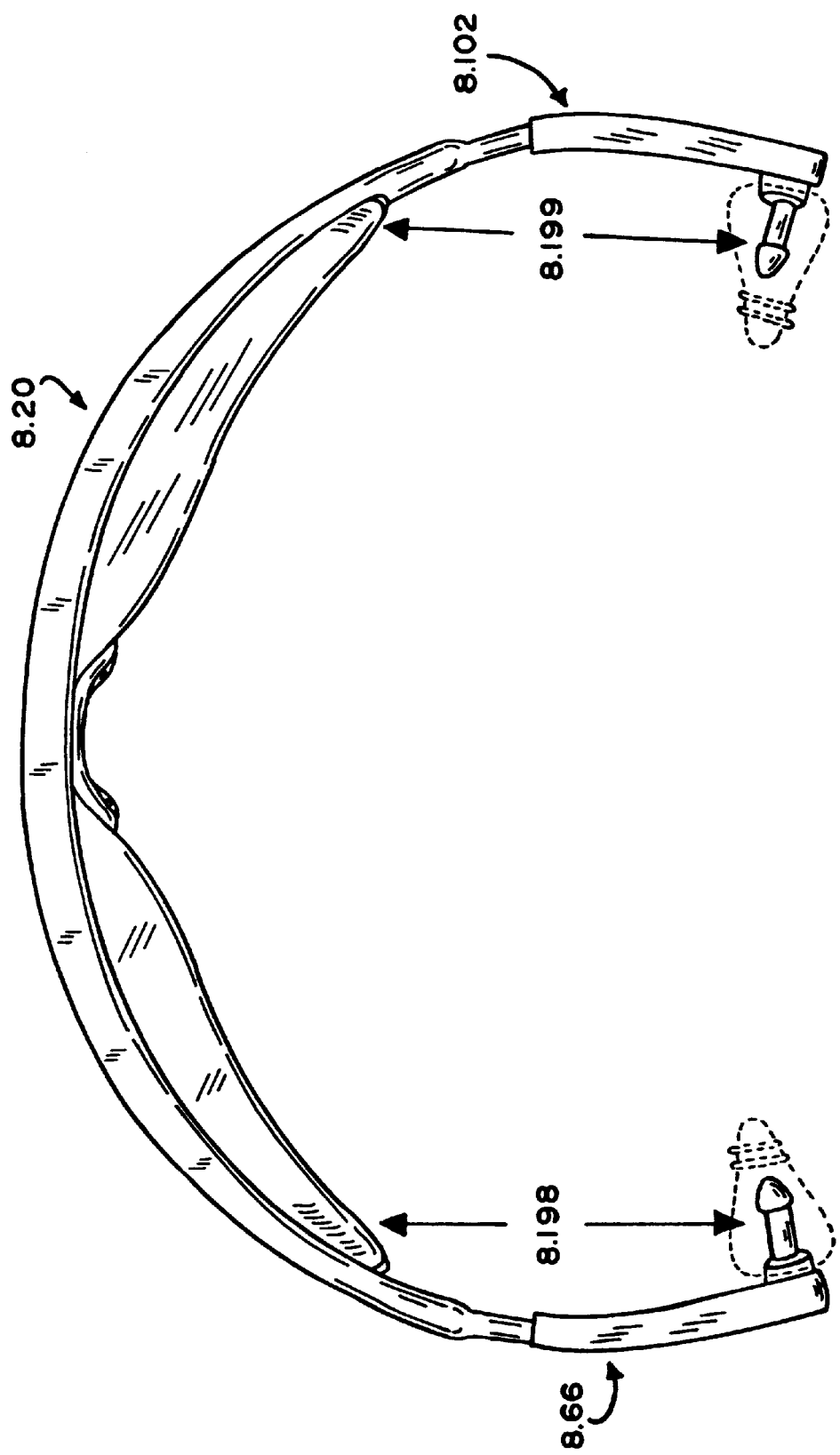
FIG. 80 is a top view of the eighth embodiment of the present invention with attached earplugs shown in dotted outline.
Figure 81:
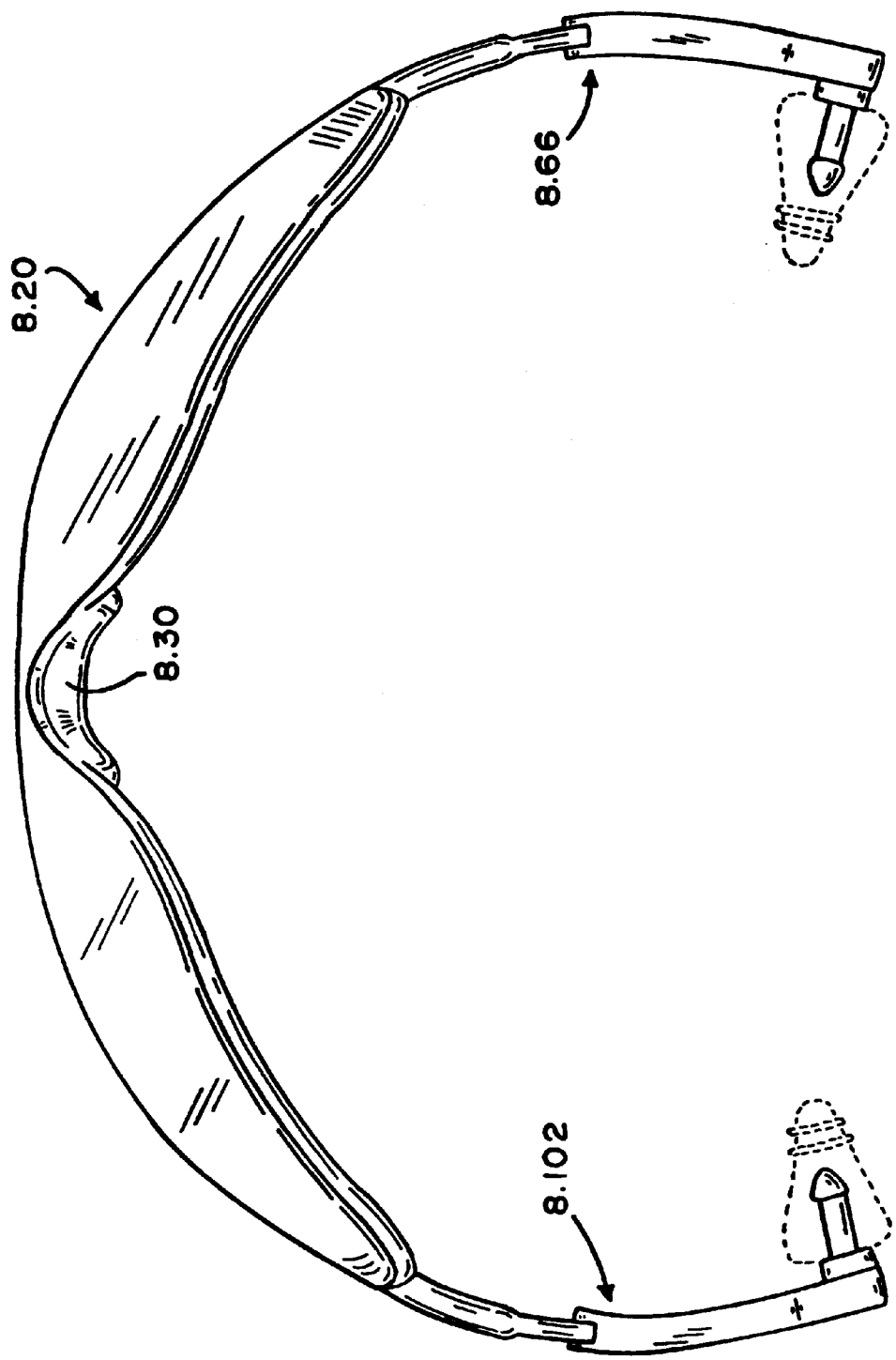
FIG. 81 is a bottom view of the eighth embodiment of the present invention with attached earplugs shown in dotted outline.
Figure 82:
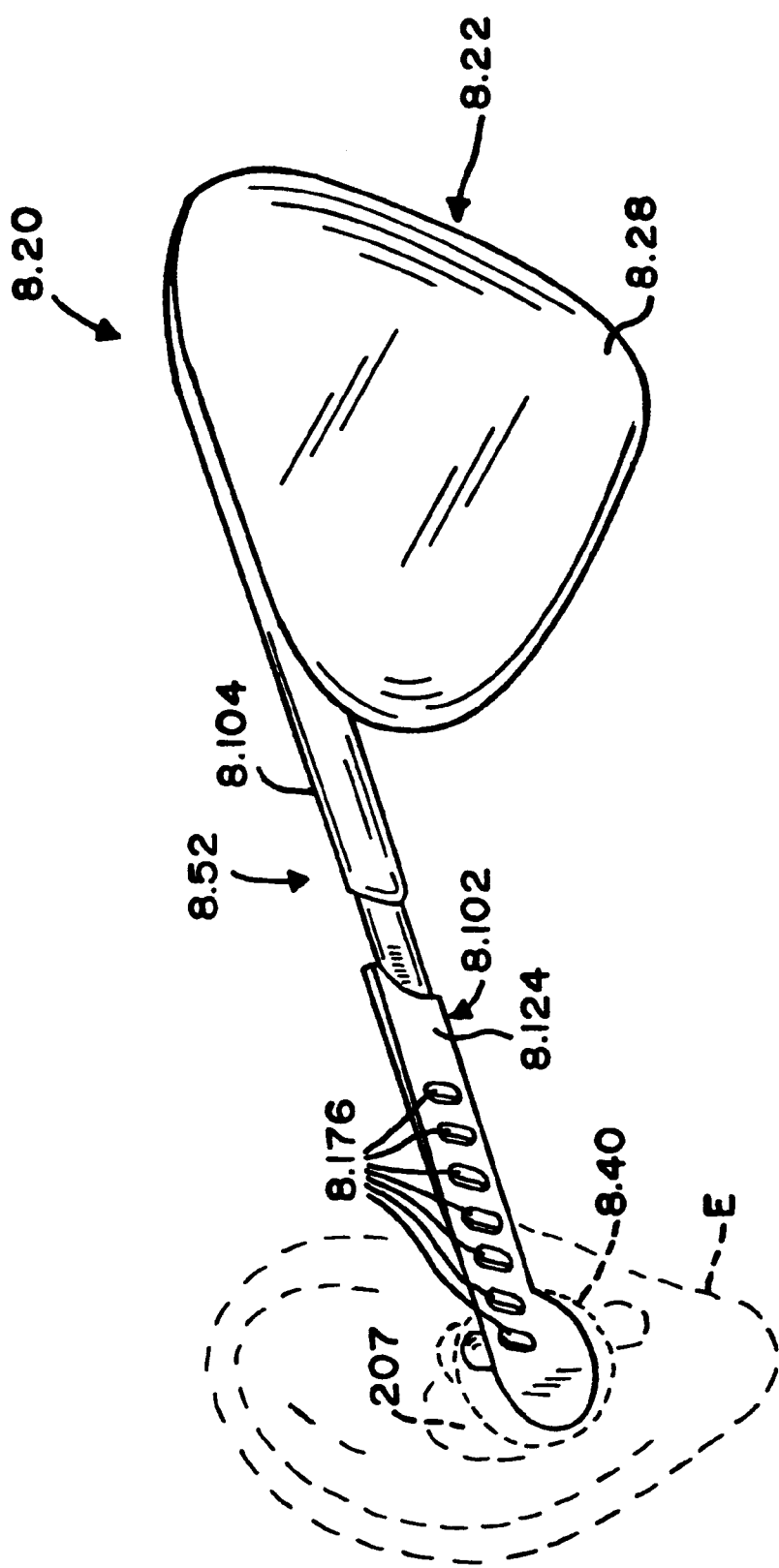
FIG. 82 is a side view of the eighth embodiment of the present invention, the view from the other side being a substantially similar mirror image, with attached earplugs shown in dotted outline.

A basic understanding of the well-known external anatomy of the human ear is helpful for understanding the present invention. Referring to FIG. 68, a well-known human ear E is shown. The external ear consists of an expanded portion of cartilage called the pinna or auricle 205, which is of a generally ovoid form. The ear canal C opens within the bowl or concha 207, which is a capacious cavity formed within the pinna. The concha is partially spanned by opposing protrusions, the tragus 208 and the antitragus 209, separated by a wide notch.

Earplugs and earpieces are of several general forms. So-called "aural" earplugs and earpieces insert into the ear canal of the wearer and substantially block the ear canal. So-called "semi-aural" earplugs and earpieces are partially inserted into the ear canal and also block the entrance of the ear canal in the concha. So-called "supra-aural" earplugs and earpieces block the entrance to the ear canal in the concha without entering the ear canal itself. Still another form of earpiece, a "support-only" comfort pad earpiece that does not block the ear canal but instead only rests in the concha of the wearer's ear, can also be used with the various embodiments of the present invention as shown, for example, in FIGS. 46–48 and 59–60, to support the eyewear of the present invention from the wearer's ear without blocking the ear canal, as hereinafter described. It shall be understood that the terms "earplugs" and "earpieces", as used herein, have a scope that encompasses all of these forms of earplugs and earpieces, including the aural, semi-aural, supra-aural, and support-only comfort pad earpiece forms, and the term "earpiece", as used herein, shall be understood to be defined to be the generic term for all of these earpieces and earplugs.

A key difference between the first embodiment (shown in FIGS. 1–9A) and the second and third embodiments (i.e., the improvements shown in FIGS. 10–21A) is that the second and third embodiments provide for audio capability through earpieces (earphones and earplugs with audio capability), while the first embodiment lacks such audio capability. In all of the first three embodiments, however, the eyewear is supported from the earpieces that are received into the ear, and no support is provided by any over-the-ear supports as are customary in prior art eyeglasses. A fourth embodiment, also described, has one temple that includes an earloop for hooking or looping over one of the wearer's ears.

Figure 1:
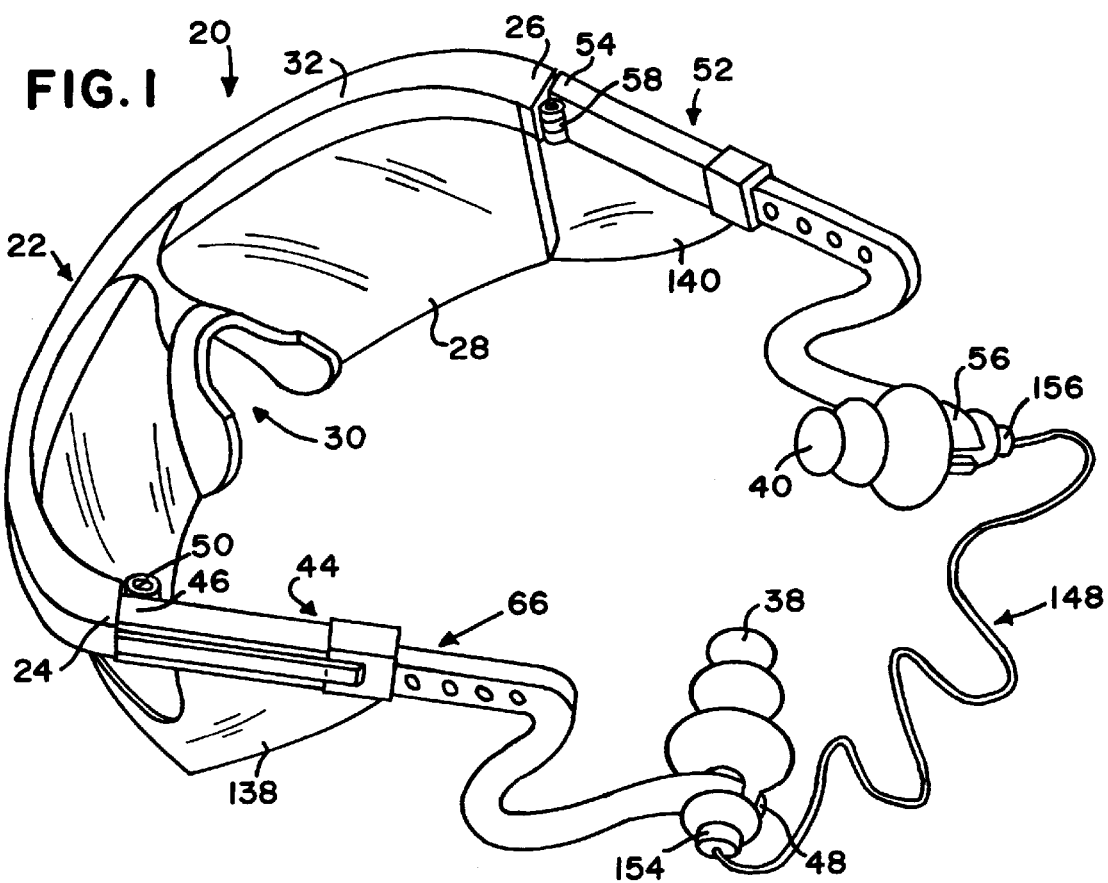
FIG. 1 is a perspective view of a first embodiment of the present invention.
Figure 2:
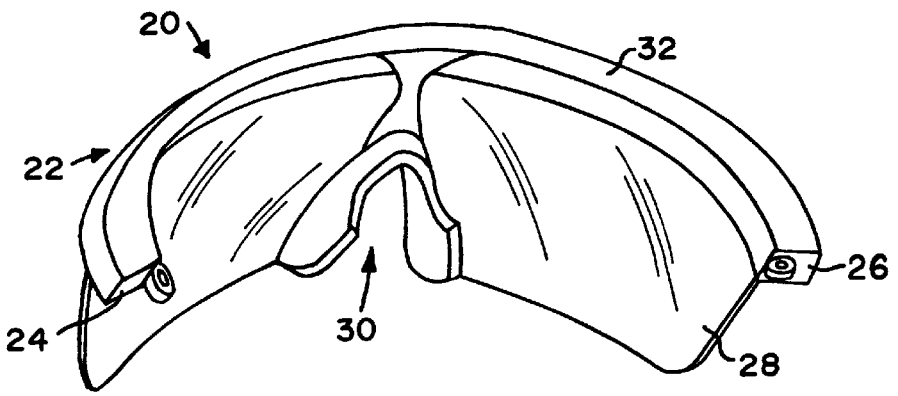
FIG. 2 is a perspective view of the front guard portion.

Accordingly, the first embodiment will now be explained by referring to FIGS. 1–9A, and the first embodiment is seen to comprise an eyesight and hearing safety apparatus 20. Referring to FIGS. 1 and 2, eyesight and hearing safety apparatus 20 is seen to comprise a front guard portion 22 having a left front guard portion end 24 and a right front guard portion end 26. The front guard portion 22 includes a front transparent panel 28 for protecting the eyesight of a human being. The front transparent panel 28 is preferably constructed from a well known clear plastic material suitable for viewing therethrough. The front guard portion 22 includes a well known bridge portion 30 for supporting the front guard portion 22 on the nose of a human being. The front guard portion 22 preferably includes an elongated front member or browpiece 32. The front transparent panel 28 is disposed adjacent to the elongated member 32 and is preferably attached thereto. The elongated member 32 is preferably constructed in the shape of a curve and includes the well known bridge portion 30 depending therefrom. The bottom surface of the elongated member 32 has a first groove (hidden) and the top surface of the bridge portion 30 has a second groove (hidden). The first and second grooves are for securing the front transparent panel 28 as is well known in the art. The elongated member 32 preferably includes the left front guard portion end 24 and the right front guard portion end 26. Further details concerning the construction and operation of the elongated member 32 will be described hereinafter.

Referring to FIGS. 1 and 6, the eyesight and hearing safety apparatus 20 is seen to further comprise a first earpiece or earplug 38 and a second earpiece or earplug 40 for supporting the front guard portion 22 from a respective auditory canal when the human being is wearing the apparatus 20 to protect the eyesight and hearing of the human being. The first and second earplugs 38, 40 are preferably constructed to each have multiple curved elements 42 for snugly engaging the auditory canal. The diameter of each curved element 42 decreases as the particular curved element 42 is located closer to the end which first engages the auditory canal. Each earplug 38, 40 preferably further includes an attachment stem 43 for attaching the earplugs 38, 40 to the eyesight and hearing safety apparatus 20. Each earplug 38, 40 is preferably constructed from a well known rubber material.

Referring to FIG. 1, the eyesight and hearing safety apparatus 20 is seen to further comprise a first temple 44 having a first attachment end 46 and a first support end 48. The first attachment end 46 is attached to the left front guard portion end 24, preferably by well known hinge means, such as first hinge 50. The first earplug 38 is attached to the first temple 44, preferably adjacent the first support end 48. The first temple 44 is constructed to have a shape so that the first earplug 38 can be inserted into the left auditory canal of the human being and so that the first earplug 38 will support the front guard portion 22 when inserted into the left auditory canal of the human being.

Referring to FIG. 1, the eyesight and hearing safety apparatus 20 is seen to further comprise a second temple 52 having a second attachment end 54 and a second support end 56. The second attachment end 54 is attached to the right front guard portion end 26, preferably by well known hinge means, such as second hinge 58. The second earplug 40 is attached to the second temple 52, preferably adjacent the second support end 56. The second temple 52 is constructed to have a shape so that the second earplug 40 can be inserted into the right auditory canal of the human being and so that the second earplug 40 will support the front guard portion 22 when inserted into the right auditory canal of the human being.

The first and second earplugs 38, 40 and the bridge portion 30 cooperate to support the front guard portion 22 on the head of the human being. The bridge portion 30 supports the front guard portion 22 on the nose of the human being. When inserted into the left auditory canal, the first earplug 38 supports the first temple 44, preferably adjacent the first support end 48. The first temple 44 is attached to the left front guard portion end 24 so that the first earplug 38 supports the left side of the front guard portion 22. Similarly, the second earplug 40 supports the second temple 52, preferably adjacent the second support end 56. The second temple 52 is attached to the right front guard portion end 26 so that the second earplug 40 supports the right side of the front guard portion 22.

Preferably, the first and second temples 44, 52 are formed so that the first and second support ends 48, 56 are laterally displaced towards each other, so that the first and second support ends 48, 56 are displaced lower than the respective first and second attachment ends 46, 54, and so that the first and second support ends 48, 56 are angled slightly upward to facilitate in placing the first 38 and second 40 earplugs into the respective auditory canal of the human being.

Referring to FIGS. 1 and 2, the elongated member 32 preferably is resilient so as to allow the front guard portion 22 to flex slightly outward in response to an applied outward pressure while the apparatus 20 is being placed on or removed from the head of the human being. While on the head of the human being, the resilience of elongated member 32 creates an inward pressure respectively at the left and right front guard portion ends 24, 26, and this inward pressure is transmitted along the first and second temples 44, 52 to comfortably secure the first and second earplugs 38, 40 in the respective auditory canal. The elongated member 32 is preferably constructed from a well known resilient material such as, for example, plastic.

First and second temples 44, 52 are resilient, and transmit the inward pressure created by the resilience of elongated member 32 to rear temple portions 88, 124 which, in turn, exert an inwardly-directed force acting through earplugs 38, 40 (i.e., forcing the earplugs 38, 40 toward each other through the wearer's head), with the inwardly-directed force through each earplug being preferably at least about one Newton (about 3.6 ounces Avoirdupois) and with the inwardly-directed force through each earplug preferably being about 6 ounces Avoirdupois (1.67 Newtons) so as to comfortably secure the eyewear onto the wearer's head during physical activity. If earpiece 38, 40 is an aural, semi-aural, or supra-aural earplug, then this force also seals the earplug to the ear canal.

Preferably, the bridge portion 30, the first earplug 38, and the second earplug 40 provide the only means of supporting the front guard portion 22 when the human being is wearing the apparatus 20 to protect the eyesight and hearing of the human being. The eyesight and hearing safety apparatus 20 does not require the temples 44, 52 to include portions to support the apparatus 20 on the top of the ears, nor does the apparatus 20 require a strap to support the apparatus 20 around the back of the head of the human being. If the first and second earplugs 38, 40 are removed and the apparatus 20 is worn by the human being, the first and second support ends 48, 56 will apply an uncomfortable pressure against the ears of the human being, thus, deterring wearing of the apparatus 20 without the first and second earplugs 38, 40. Additionally, without the first and second earplugs 38, 40, the front guard portion 22 will not be firmly secured in place as will be the case when the first and second earplugs 38, 40 are inserted into the respective auditory canals of the human being.

Referring to FIGS. 1, 5, and 6, the first temple 44 preferably includes a first means of attaching the first earplug 38 to the first temple 44. The first means of attaching preferably comprises a first aperture 60 extending through the first temple 44 adjacent the first support end 48. The first aperture 60 preferably has a first slot 62 through which the attachment stem 43 of the first earplug 38 can be forced so that it is secured in the first aperture 60. While secured in the first aperture 60, the first earplug 38 is preferably attached to the first temple 44 at a fixed first predetermined location of attachment along a length of the first temple 44. The first earplug 38 is preferably attached to the first temple 44 to have a position which is substantially non-adjustable along the length of the first temple 44 with respect to the first predetermined location of attachment.

Once the first earplug 38 is secured in the first aperture 60, the first earplug 38 can be removed by forcing the attachment stem 43 of the first earplug 38 through the first slot 62 in the opposite direction. The removed first earplug 38 can then be cleaned or replaced as is necessary. The first means of attaching could comprise other well known means for attaching the first earplug 38 to the first temple 44 such as, for, example, a screw or an end plug extending through the first aperture 60 and into the first earplug 38.

Figure 9A:
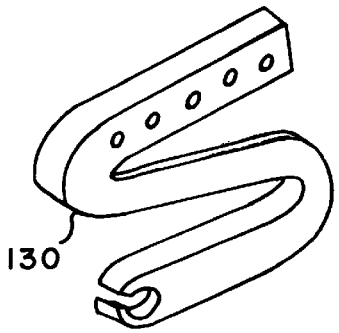
FIG. 9A is a perspective view of the other portion of the second temple shown adjusted to a second vertical position.
Figure 9:
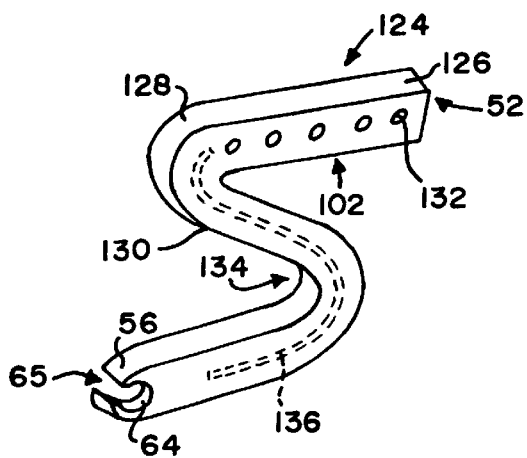
FIG. 9 is a perspective view of another portion of the second temple shown adjusted to a first vertical position.
Figure 17:
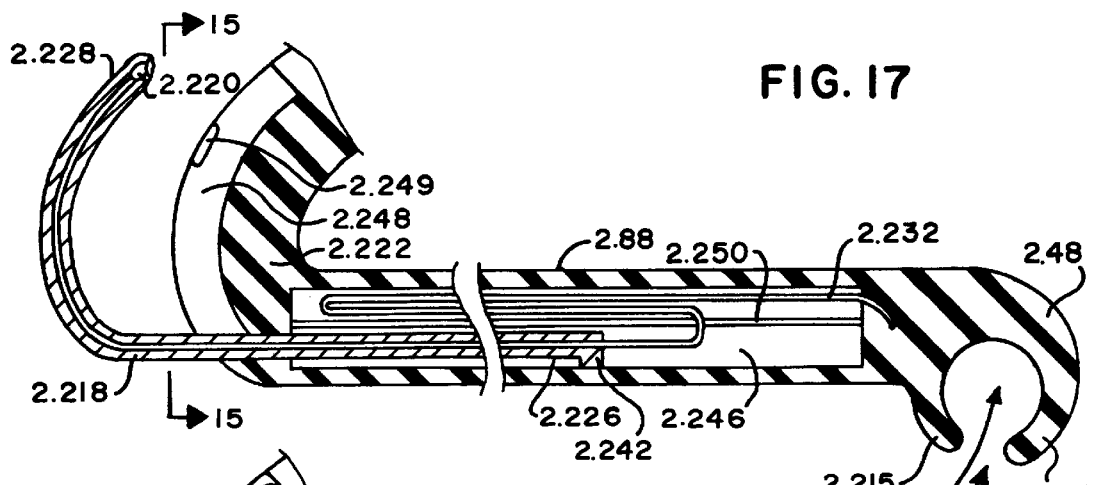
FIG. 17 is a side sectional view of a portion of the temple of the second and third embodiments, showing the microphone boom in a partially-extended position.

Referring to FIGS. 1, 6, and 9, the second temple 52 preferably includes a second means of attaching the second earplug 40 to the second temple 52. The second means of attaching preferably comprises a second aperture 64 extending through the second temple 52 adjacent the second support end 56. The second aperture 64 preferably has a second slot 65 through which the attachment stem 43 of the second earplug 40 can be forced so that it is secured in the second aperture 64. While secured in the second aperture 64, the second earplug 40 is preferably attached to the second temple 52 at a fixed second predetermined location of attachment along a length of the second temple 52. The second earplug 40 is preferably attached to the second temple 52 to have a position which is substantially non-adjustable along the length of the second temple 52 with respect to the second predetermined location of attachment.

Once the second earplug 40 is secured in the second aperture 64, the second earplug 40 can be removed by forcing the attachment stem 43 of the second earplug 40 through the second slot 65 in the opposite direction. The removed second earplug 40 can then be cleaned or replaced as is necessary. The second means of attaching could comprise other well known means for attaching the second earplug 40 to the second temple 52 such as, for, example, a screw or an end plug extending through the second aperture 64 and into the second earplug 40.

Referring to FIGS. 1, 3, and 4, the first temple 44 preferably includes first horizontal adjustment means 66 for horizontally adjusting the first earplug 38 to a selected horizontal position. First horizontal adjustment means 66 preferably includes a first front temple portion 68. The first front temple portion 68 has an end which serves as the first attachment end 46 of the first temple 44. The first front temple portion 68 is preferably constructed in the shape of a sleeve having a rectangular cross section. The first front temple portion 68 has a first receiving end 70 and a first channel 72 extending longitudinally from the first receiving end 70 and into the interior of the first front temple portion 68. Referring to FIG. 4, a first outward side 74 of the first front temple portion 68 has a first hole 76 extending therethrough. First horizontal adjustment means 66 preferably further includes a first resilient member 78 having a first resilient member attachment end 80 and a first resilient member tab end 82. The first resilient member attachment end 80 is attached to the first outward side 74 of the first front temple portion 68, adjacent the first attachment end 46. FIG. 3 shows the first resilient member 78 in its normal in-use position, while FIG. 4 shows the first resilient member 78 in a lifted position. The first resilient member 78 includes a first pin 84 which removably extends through the first hole 76. The first resilient member 78 includes a first tab 86 adjacent the first resilient member tab end 82. The first pin 84 can be retracted from the first hole 76 by lifting the first tab 86 away from the first outward side 74 of the first front temple portion 68 as shown in FIG. 4. The first resilient member 78 is constructed from a well known resilient material, such as a resilient plastic or metal.

Referring to FIG. 5, the first temple 44 preferably includes a first rear temple portion 88 including a first arm 90 having a first arm end 92 being connected to a first deformable shape retaining member 94 at the first arm end 92. The first deformable shape retaining member 94 preferably includes the first support end 48 and is attached to the first earplug 38 (shown in FIG. 1). First horizontal adjustment means 66 preferably includes the first arm 90, and the first arm 90 is sized for receipt into the first channel 72 (shown in FIG. 3). The first arm 90 has a first plurality of apertures 96 for selectively receiving the first pin 84 (shown in FIG. 4) to horizontally position the first earplug 38 (shown in FIG. 1). Referring to FIGS. 1, 3, 4, and 5, the horizontal position of the first earplug 38 can be changed by first lifting the first tab 86 to retract the first pin 84 from the first hole 76 and one of the first plurality of apertures 96. Next, the horizontal position of the first earplug 38 can be changed so that another one of the first plurality of apertures 96 is aligned with the first hole 76. Finally, the first tab 86 is released, the first pin 84 is forced into the selected one of the first plurality of apertures 96 by the first resilient member 78, and the first earplug 38 is secured into the selected horizontal position.

Referring to FIGS. 1, 5, and 5A, the first temple 44 preferably includes first vertical adjustment means 98 for vertically adjusting the first earplug 38 to a selected vertical position. First vertical adjustment means 98 preferably includes the first deformable shape retaining member 94 which is selectively adjustable to vertically position the first earplug 38. The first deformable shape retaining member 94 is preferably constructed by including a first wire 100 inside a flexible material, such as a suitable plastic or rubber material. The first deformable shape retaining member 94 is attached to the first arm end 92. The first arm 90 and the first deformable shape retaining member 94 form the first rear temple portion 88 which preferably has a shape substantially in the form of an S or Z. Notably, the first deformable shape retaining member 94 is preferably constructed laterally inwardly with respect to the first arm 90. The first deformable shape retaining member 94 can be can be vertically adjusted to selectively vertically position the first earplug 38 by applying sufficient force to the first deformable shape retaining member 94 in the desired vertical direction. The first deformable shape retaining member 94 will remain in the vertically adjusted position until sufficient force is applied to position the first deformable shape retaining member 94 to a different vertical position. FIGS. 5 and 5A show the first deformable shape retaining member 94 adjusted to two different vertical positions.

Figure 8:
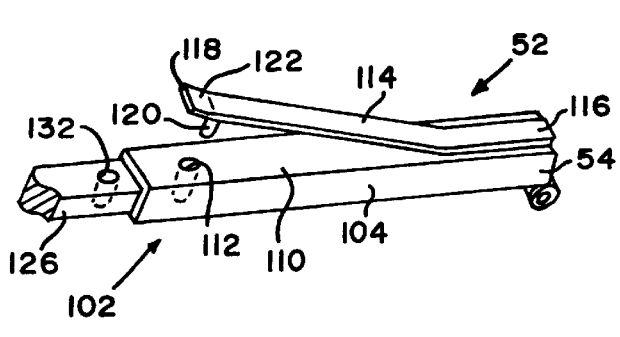
FIG. 8 is a different perspective view of the portion of the second temple shown in FIG. 7.
Figure 7:
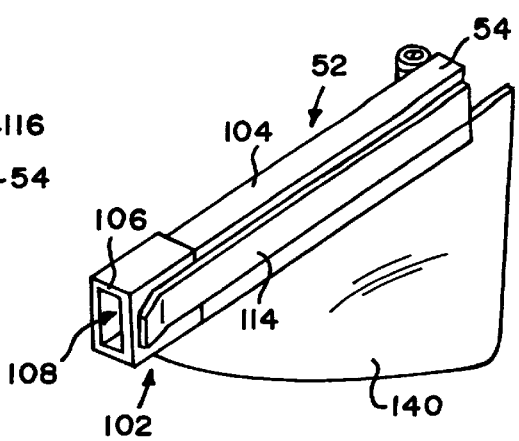
FIG. 7 is a perspective view of a portion of a second temple and of a second side transparent panel.

Referring to FIGS. 1, 7, and 8, the second temple 52 preferably includes second horizontal adjustment means 102 for horizontally adjusting the second earplug 40 to a selected horizontal position. Second horizontal adjustment means 102 preferably includes a second front temple portion 104.

The second front temple portion 104 has an end which serves as the second attachment end 54 of the second temple 52. The second front temple portion 104 is preferably constructed in the shape of a sleeve having a rectangular cross section. The second front temple portion 104 has a second receiving end 106 and a second channel 108 extending longitudinally from the second receiving end 106 and into the interior of the second front temple portion 104. Referring to FIG. 8, a second outward side 110 of the second front temple portion 104 has a second hole 112 extending therethrough. Second horizontal adjustment means 102 preferably further includes a second resilient member 114 having a second resilient member attachment end 116 and a second resilient member tab end 118. The second resilient member attachment end 116 is attached to the second outward side 110 of the second front temple portion 104, adjacent the second attachment end 54. FIG. 7 shows the second resilient member 114 in its normal in-use position, while FIG. 8 shows the second resilient member 114 in a lifted position. The second resilient member 114 includes a second pin 120 which removably extends through the second hole 112. The second resilient member 114 includes a second tab 122 adjacent the second resilient member tab end 118. The second pin 120 can be retracted from the second hole 112 by lifting the second tab 122 away from the second outward side 110 of the second front temple portion 104 as shown in FIG. 8. The second resilient member 114 is constructed from a well known resilient material, such as a resilient plastic or metal.

Referring to FIG. 9, the second temple 52 preferably includes a second rear temple portion 124 including a second arm 126 having a second arm end 128 being connected to a second deformable shape retaining member 130 at the second arm end 128. The second deformable shape retaining member 130 preferably includes the second support end 56 and is attached to the second earplug 40 (shown in FIG. 1). Second horizontal adjustment means 102 preferably includes the second arm 126, and the second arm 126 is sized for receipt into the second channel 108 (shown in FIG. 7). The second arm 126 has a second plurality of apertures 132 for selectively receiving the second pin 120 (shown in FIG. 8) to horizontally position the second earplug 40 (shown in FIG. 1). Referring to FIGS. 1, 7, 8, and 9, the horizontal position of the second earplug 40 can be changed by first lifting the second tab 122 to retract the second pin 120 from the second hole 112 and one of the second plurality of apertures 132. Next, the horizontal position of the second earplug 40 can be changed so that another one of the second plurality of apertures 132 is aligned with the second hole 112. Finally, the second tab 122 is released, the second pin 120 is forced into the selected one of the second plurality of apertures 132 by the second resilient member 114, and the second earplug 40 is secured into the selected horizontal position.

Referring to FIGS. 1, 9, and 9A, the second temple 52 preferably includes second vertical adjustment means 134 for vertically adjusting the second earplug 40 to a selected vertical position. Second vertical adjustment means 134 preferably includes the second deformable shape retaining member 130 which is selectively adjustable to vertically position the second earplug 40. The second deformable shape retaining member 130 is preferably constructed by including a second wire 136 inside a flexible material, such as a suitable plastic or rubber material. The second deformable shape retaining member 130 is attached to the second arm end 128. The second arm 126 and the second deformable shape retaining member 130 form the second rear temple portion 124 which preferably has a shape substantially in the form of an S or Z. Notably, the second deformable shape retaining member 130 is preferably constructed laterally inwardly with respect to the second arm 126. The second deformable shape retaining member 130 can be can be vertically adjusted to selectively position the second earplug 40 by applying sufficient force to the second deformable shape retaining member 130 in the desired vertical direction. The second deformable shape retaining member 130 will remain in the vertically adjusted position until sufficient force is applied to position the second deformable shape retaining member 130 to a different vertical position. FIGS. 9 and 9A show the second deformable shape retaining member 130 adjusted to two different vertical positions.

The first and second temples 44, 52 can be adjusted by using the respective horizontal adjustment means 66, 102 and the respective vertical adjustment means 98, 134. In this manner, the first and second earplugs 38, 40 can be positioned to be secured in the auditory canals of human beings with different sized and shaped heads. The eyesight and hearing safety apparatus 20 will be securely held in place and the human being can be very physically active.

Referring to FIGS. 1 and 3, the eyesight and hearing safety apparatus 20 preferably includes a first side transparent panel 138 being disposed adjacent the first temple 44 and preferably being attached to the first front temple portion 68 by means well known in the art. Referring to FIGS. 1 and 7, the eyesight and hearing safety apparatus 20 preferably includes a second side transparent panel 140 being disposed adjacent the second temple 52 and preferably being attached to the second front temple portion 104 by means well known in the art. The first and second side transparent panels 138, 140 are preferably constructed from a well known clear plastic material suitable for viewing therethrough.

Referring to FIG. 6, each earplug 38, 40 preferably includes a ball 142 being attached at one end to the attachment stem 43 and having an earplug aperture 144 at the other end. The earplug aperture 144 leads to a reception cavity (hidden) constructed inside the ball 142.

Referring to FIGS. 1 and 6, the eyesight and hearing safety apparatus 20 preferably includes suspending means 148 for suspending the apparatus 20 from the neck of a human being. Suspending means 148 preferably comprises an elongated securing tiepiece 150. The elongated securing tiepiece 150 is preferably constructed from rubber, but, may be constructed from woven fibers, leather, plastic, or any other well known suitable material. Suspending means 148 includes detaching means 152 for detaching suspending means 148 from the apparatus 20 in response to an applied force. Detaching means 152 preferably comprises a first retaining element 154 attached to one end of the elongated securing tiepiece 150 and a second retaining element 156 attached to the other end of the elongated securing tiepiece 150. The first and second retaining elements 154, 156 are constructed to be removably received into the earplug aperture 144 and reception cavity of each respective earplug 38, 40. When the first and second retaining elements 154, 156 are received in the respective reception cavities, the eyesight and hearing safety apparatus 20 can be removed from the head of the human being, and the human being can suspend the apparatus 20 from his or her neck. If the apparatus 20 should accidentally become caught in a piece of machinery, one or both of the retaining elements 154, 156 will be removed from the respective reception cavity due to the force of the machinery pulling on the apparatus 20. In this manner, injury that could be caused by the machinery is prevented. The first and second retaining elements 154, 156 can be constructed from well known materials such as rubber or plastic.

Now that the first embodiment of the invention has been explained, the improvements of the second, third, and fourth embodiments can be described.

A second preferred embodiment of the present invention is shown in FIGS. 10 and 12–21A, with identifying reference designators marked similarly to the first embodiment, except with the prefix "2.". Likewise, a third preferred embodiment is shown in FIG. 11, with identifying reference designators marked similarly to the first and second embodiments, except with the prefix "3.". It shall be understood that many aspects of the first, second, and third embodiments are substantially the same, and only the differences will be treated in detail.

Now referring to FIGS. 10–21A, the second and third embodiments 2.20 and 3.20 are seen to have a front portion 2.22 or 3.22, respectively, each including a front transparent panel 2.28 or 3.28, respectively, for protecting the human being's eyesight. As shown in FIG. 10, the front transparent panel 2.28 of the second embodiment may be well-known protective glass or plastic similar to that in well-known "safety glasses", and as described hereinbefore for the first embodiment 20, and this protective panel 2.28 may also be tinted or polarized, in a manner well-known to those skilled in the art, for protection of the wearer's eyes from some undesired portions of the spectrum. It shall be understood that the second embodiment may also, if desired, include the left and right side guard transparent panels of the first embodiment, but not shown in FIG. 10. As shown in FIG. 11, the front transparent panel 3.28 of the third embodiment 3.20 may instead be well-known corrective lenses that also may be tinted or polarized to protect the wearer's eyes while also correcting the wearer's vision.

The front transparent panels 2.28, 3.28 of the second and third embodiments include left front portion ends 2.24, 3.24, respectively, and right front portion ends 2.26, 3.26, respectively, with a left temple, 2.44 or 3.44, respectively, being attached to the respective left front portion end 2.24 or 3.24. It shall be understood that the second and third embodiments each also include a right temple, 2.52 or 3.52, respectively, and, because of similarities between the left and right temples of each embodiment, a description of the left temple alone will suffice for both, it being understood that similar features on the right temple will simply be a mirror image of those same features on the left temple. However, it shall be understood that the optional and retractable microphone boom, hereinafter described, need be included on only one of the temples.

Temples 2.44 and 3.44 include a substantially fixed-length left shape-retaining member 2.94 or 3.94, respectively, and, because of the substantial similarity between the shape-retaining members 2.94 and 3.94, a description of one, hereinafter given, will suffice for both.

Second and third embodiments 2.20 and 3.20 each also include left earpieces 2.38 or 3.38, respectively, and right earpieces 2.40 or 3.40, respectively. It shall be understood that these earpieces can be "mixed and matched" to suit the particular needs of the wearer. A common feature of the improvement of the second and third embodiments of the present invention is that at least one of the left and right earpieces of those embodiments includes earphone means, such as well-known earphone means 2.204, for converting an electrical signal into audible sound. The left and right earpieces are adapted for supporting the front portion of the apparatus from the human being's respective left and right auditory canals when the human being is wearing said apparatus, in a manner hereinafter described, with the second and third embodiments having no means for supporting the apparatus from the human being's ears other than said left and right earpieces. In other words, contrary to known prior art devices, there is no support portion of the respective temples that passes over the wearer's ear to support the apparatus.

As shown in FIGS. 10, 11, and 11A, earpieces 2.38, 2.40, 3.38, 3.40, and 3.40' have many similar features, and the appropriate choice of earpiece may be made by the wearer. Although the earpieces shown in FIGS. 10 and 11 all include earphone means for converting an electrical signal into sound, with the earphone means being in communication through a longitudinal bore (e.g., bore 2.203 or 3.203, respectively) therethrough to the respective left or right auditory canal of the wearer, there are variations in the earpieces. For example, the earpiece 3.40 is similar to the earplug 40 of the first embodiment in that it is pluggingly received into the auditory canal of the wearer for substantially blocking outside noises from transmission into the wearer's ear, thereby protecting the wearer's hearing. However, unlike the earplug 40 of the first embodiment, the earpiece 3.40 includes earphone means within its retaining element 3.156 that is removably received into the earpiece 3.40 in a manner similar to the removable receipt of retaining element 156 into earplug 40. Thus, earpiece 3.40 acts not only as a protective earplug, blocking outside noises from the wearer's ear, but also acts as an earphone, while still allowing the securing tiepiece 3.150 to become detached for safety from the earpiece 3.40 in a manner hereinbefore described. As in the first embodiment, earpiece 3.40 is preferably made of soft, flexible rubber or high-density foam so as to sealingly plug the wearer's auditory canal from outside noises.

Earpieces 2.38, 2.40, and 3.38 are substantially the same, and a description of earpiece 2.38 will suffice for all of them. The common feature of earpieces 2.38, 2.40, and 3.38 is that they do not plug the wearer's ear from outside sounds, but instead allow those sounds to pass by not being sealingly and pluggingly received into the wearer's auditory canal, instead being retained in the wearer's outer ear at the mouth of the auditory canal.

The retention of the earpiece 2.38 within the wearer's ear can be explained by reference to FIGS. 12 and 13. As is well-known in human anatomy, in front of the bowl or concha 2.207 of the ear E and projecting backward over the meatus is a small pointed eminence, the tragus 2.208. Opposite the tragus 2.208, and separated from it by a deep notch, is a small tubercle called the antitragus 2.209. As shown in FIGS. 12 and 13, earpiece 2.38 rests in the bowl or concha 2.207 at the mouth of the auditory canal C of the wearer, and is held in place by opposing cartilage flap protrusions of the tragus 2.208 and anti-tragus 2.209 of the wearer's ear E. The covering of earpiece 2.38 is preferably made of soft, flexible rubber or low-density foam so as to provide extended-wear comfort for the wearer while also allowing outside sounds and noises to be heard.

Referring again to FIGS. 10–11 and FIGS. 14–21A, further details of the improvements of the second and third embodiments can now be described.

Earpiece 2.38 includes an attachment stem 2.43 for attaching earpiece 2.38 to its respective shape-retaining member in fixed relation thereto. Attachment stem 2.43 has a plurality of longitudinally-spaced grip portions, e.g., grip portions 2.210 and 2.212 for longitudinally adjusting the inward to outward position of the earpiece 2.38. Substantially fixed-length deformable shape retaining member 2.94 includes grip means 2.214, similar to the C-shaped grip at support end 48 of the first embodiment, for selectively engaging one of the grip portions 2.210, 2.212, etc., of attachment stem 2.43 as especially shown in FIG. 14.

Grip means 2.214 includes first and second opposed fingers 2.215 and 2.216 that form a transverse aperture 2.60 extending through first temple 2.44 adjacent first support end 2.48 with a first slot 2.62 between opposed fingers 2.215 and 2.216 through which the selected grip portion 2.210, 2.212, etc., of attachment stem 2.43 of earpiece 2.38 can be forced so that it is secured in the first aperture 2.60 at the chosen position. While secured in the aperture 2.60, earpiece 2.38 is thus preferably attached to deformable shape-retaining member 2.94 of first temple 2.44 at a fixed first predetermined location of attachment along a length of the first temple 2.44.

The inward and outward transverse position of earpiece 2.38, however, may be adjusted by moving grip means 2.214 from one grip portion 2.210 to another grip portion 2.212 as shown in FIG. 14. Choosing a different grip portion causes earpiece 2.38 to be moved inwardly and outwardly, as desired, for holding the apparatus in place and for being comfortably received into the ear of the user. When the first earpiece 2.38 is secured within aperture 2.60, earpiece 2.38 can be removed by forcing the attachment stem 2.43 of the first earpiece 2.38 outwardly through the first slot 2.62. The removed earpiece 2.38 can then be engaged by a different grip portion 2.210, 2.212, etc., as is necessary.

It should be further understood that one of the earpieces of the second or third embodiments could lack earphone means, if desired, and simply plug the wearer's ear similar to the earplug function provided by earplugs 38 or 40 of the first embodiment, although such earplugs preferably would still have the longitudinally-spaced grip portions hereinbefore described. See, for example, earplug 3.40' of so-modified third embodiment 3.20' as shown in FIG. 11A as compared with FIG. 11. Likewise, the earplug/earphone 3.40 of FIG. 11 has similar longitudinally-spaced grip portions to those hereinbefore described for earpiece 2.38, so as to allow similar inward and outward adjustment of the position of the earpiece 3.40.

At least one of the temples may include microphone boom means 2.218 for placing a well-known microphone 2.220 in proximity to the human being's mouth while the human being is wearing the apparatus 2.20. Preferably, microphone boom means 2.218 is reciprocatingly received within temple 2.44 as by preferably being received into rear temple portion 2.88 of deformable shape-retaining member 2.94. Microphone boom means 2.218 has a proximal end 2.226 and a curved distal end 2.228, with the remote tip 2.230 of distal end 2.228 including a well-known microphone 2.220 for receiving a person's voice and transforming it into an electrical signal.

The electrical signal from microphone 2.220 travels along microphone wire 2.232 to a junction connector 2.234. Likewise, the electrical signal to earphones 2.38 and 2.40 also travel along earphone wires 2.238 and 2.239 to junction box 2.234. A well-known multiple-contact male electrical plug 2.236 is received into a mating electrical jack 2.237 in junction connector 2.234, and provides electrical connection, through multi-conductor wires 2.235 and second multiple-contact male electrical plug 2.241 to well-known electronic audio means 2.240 (such as, for example, a well-known cellular telephone, radio receiver, tape cassette, compact disc player, or two-way radio, etc.).

Microphone boom means 2.218 is preferably reciprocatingly received within rear portion 2.88 of temple 2.44, and substantially straight proximal end 2.226 slides within a longitudinal bore or cavity 2.246 formed within rear portion 2.88 as shown especially in FIGS. 17–21A. When in the fully retracted position shown in FIG. 18, curved distal end 2.228 is closely received into a recess 2.248 within the knee 2.222 of rear portion 2.88 and held slightly therewithin by a pair of opposing nibs 2.249 that extend from either side of recess 2.248. The proximal end 2.226 of microphone boom means 2.218 is retained within a lower portion of longitudinal bore or cavity 2.246 by a pair of opposing ribs 2.250 that extend from either inner side of bore 2.246, with a gap between ribs 2.250 for allowing wire 2.232 to pass therethrough so that wire 2.232 is allowed to track the reciprocation of microphone boom means 2.218.

Figure 18:
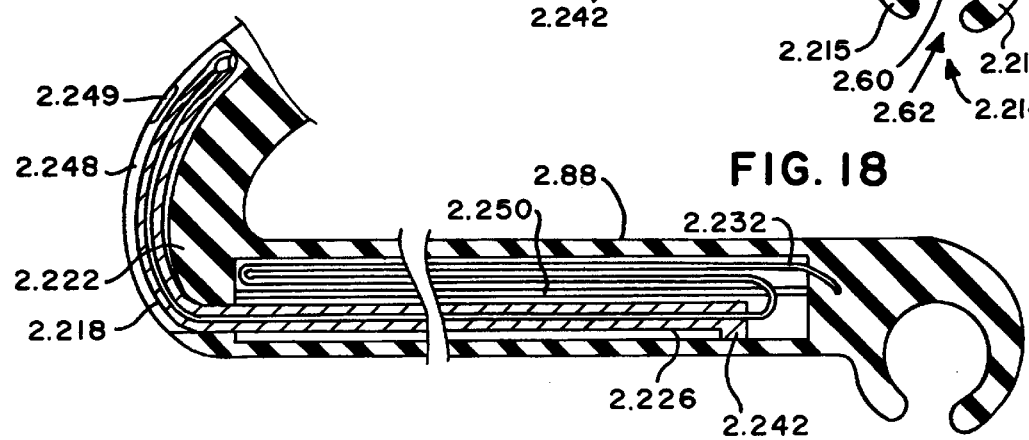
FIG. 18 is a side sectional view of a portion of the temple of the second and third embodiments, similar to FIG. 17, but showing the microphone boom in a fully-retracted position.

When in an extended position as shown in FIG. 10, for example, microphone boom 2.218 is then rotated (compare FIGS. 20 and 21 with the rotated position shown in FIGS. 20A and 21A) so as to place microphone 2.220 in a region proximate the wearer's mouth. As microphone boom 2.218 rotates, a radially-extending cam 2.242 on proximal end 2.226 of boom 2.218 contacts with a sidewall of longitudinal bore 2.246 (see FIG. 21A) so as to retain boom 2.218 locked in the rotated and extended position. To retract the microphone boom, it is first rotated in the opposite direction and then reciprocatingly slid into the temple portion 2.88 as shown in FIG. 18.

Each of temples 2.94 and 2.52 include horizontal adjustment means, 2.66 and 2.102, respectively, that are variants of the first and second horizontal adjustment means 66 and 102, respectively, of the first embodiment. Horizontal adjustment means 2.66 and 2.102 are substantially the same, being mirror images of each other, and a description of adjustment means 2.66 will suffice for both.

Figure 19:
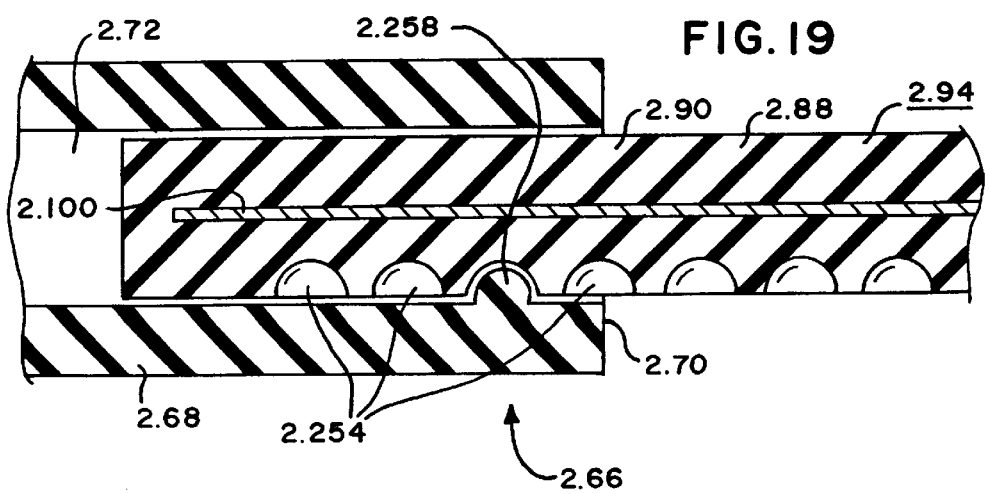
FIG. 19 is a top sectional view of the length adjustment means of the temple of the second and third embodiments.
Figure 23:
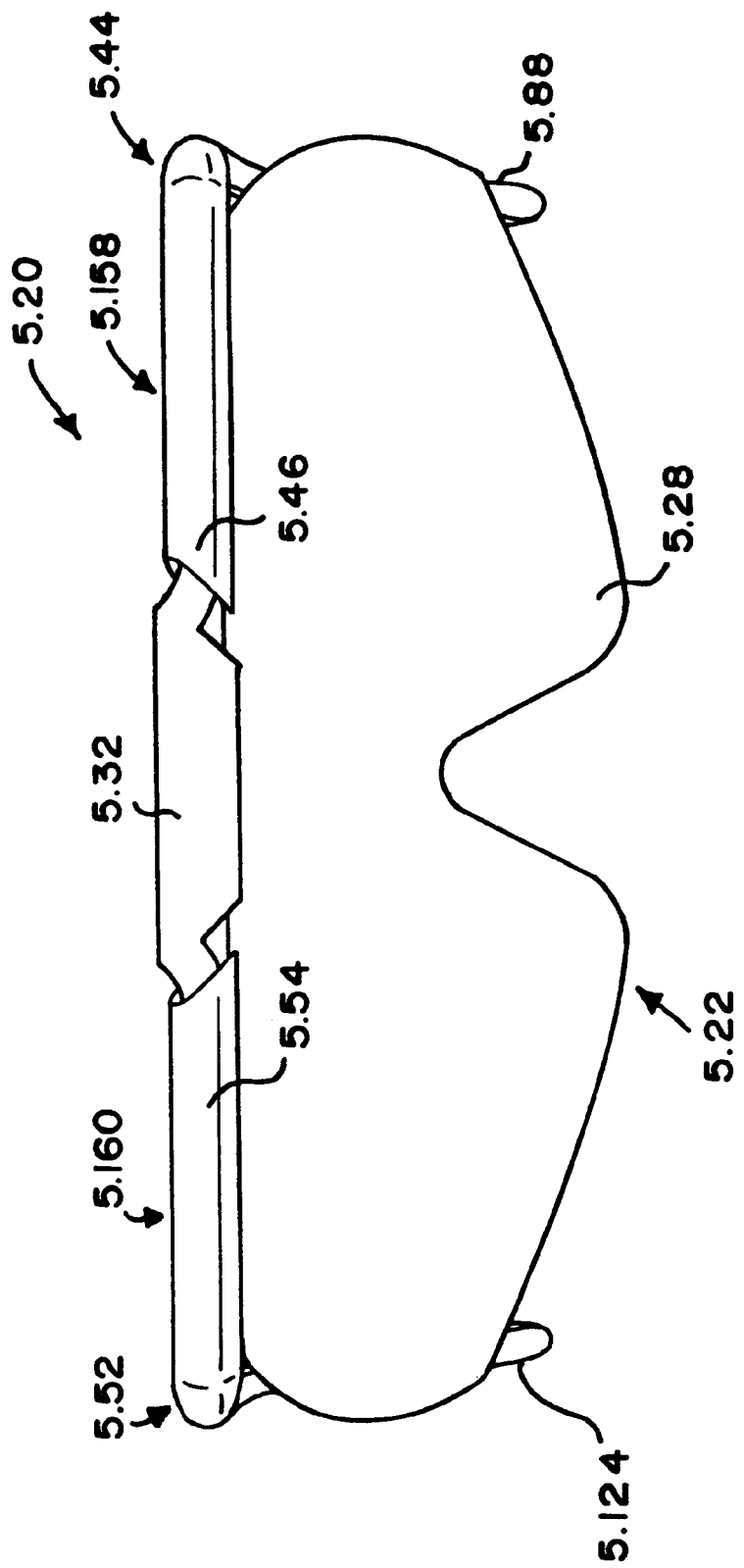
FIG. 23 is a front view of a fifth embodiment of the present invention with the rear earpieces removed.

Referring especially to FIGS. 10, 16, and 19, horizontal adjustment means 2.66 comprises a front temple portion 2.68 and a rear temple portion 2.88. Front temple portion 2.68 is preferably constructed in the shape of a sleeve having a substantially rectangular cross section into which rear temple portion 2.88 is slidably received, and further comprises a first attachment end 2.46, a first receiving end 2.70, and a first channel 2.72 extending longitudinally from the first receiving end 2.70 into the interior of the first front temple portion 2.68. First rear temple portion 2.88 includes first deformable shape retaining member 2.94 having a first arm 2.90 slidably received into the first channel 2.72. In contrast to the first embodiment which showed a plurality of holes on the first arm 90 with a pin removably extending therethrough, the first arm 2.90 of the second embodiment has a plurality of concave dimples 2.254 along one side thereof for receiving the convex protrusion 2.258 located on the interior surface of channel 2.72. When the arm 2.90 is slidingly inserted into the receiving end 2.70 of the front temple portion 2.68, the arm 2.90 extends into the first channel 2.72 and one of the concave dimples 2.254 is then snugly engaged by the convex protrusion 2.258, thereby causing the rear temple portion 2.88 to be held into the selected and desired horizontal position. The horizontal length of the first temple 2.44 and the horizontal position of the first earpiece 2.38 can be changed as desired by pulling or pushing on the first arm 2.90, thereby forcing the convex protrusion 2.258 to deform the wall of temple portion 2.68 and then engage another concave dimple 2.256 at a different selected horizontal position. To provide additional stiffness to arm 2.90 as it slidingly reciprocates within channel 2.72 during adjustment, the internal stiffening wire 2.100 of shape retaining member 2.94 may extend into arm 2.90 as shown in FIG. 19.

A fourth embodiment 4.20 of the improvements of the present invention is shown in FIG. 22, with identifying reference designators marked similarly to the first, second, and third embodiments, except with the prefix "4.". It shall be understood that many aspects of the first, second, third, and fourth embodiments are substantially the same, and only the differences will be treated in detail.

Fourth embodiment 4.20 includes a front transparent panel 4.28 similar to either of front transparent panels 2.28 or 3.28, heretofore described in detail, it being understood that panels 2.28 or 3.28 could interchangeably be used with the fourth embodiment. Fourth embodiment 4.20 includes a first temple, here shown as right temple 4.52, with right temple 4.52 having a well-known earloop means 4.270 for hooking or looping attachment over a first ear (here, the right ear) of the wearer, and right temple 4.52 preferably includes horizontal adjustment means 4.102, substantially similar to horizontal adjustment means 2.102 and 2.66, hereinbefore described, for slidable horizontal adjustment of the temple 4.52. Fourth embodiment 4.20 includes second temple, here shown as left temple 4.44, that is substantially the same as temple 2.44 of the second embodiment and including an earpiece 4.38 with included earphone means. It shall be understood that the earpiece 4.38 may either be similar to earphone earpiece 2.38, hereinbefore described, or to earplug-type earphone earpiece 3.40, hereinbefore described, with similar attachment to temple 4.44. It will be noted that, while temple 4.52 is supported from the wearer's first ear by earloop 4.270, the other temple 4.44 has no means for supporting the fourth embodiment 4.20 from the wearer's second ear other than by earpiece 4.38.

Figure 56:
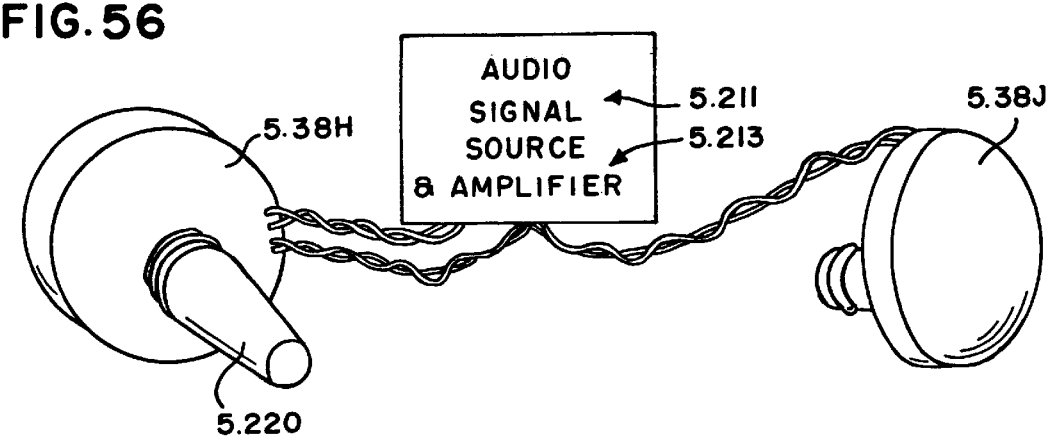
FIG. 56 shows a perspective and schematic view of a first version of audio earpieces with ear microphones for use with the fifth embodiment of the present invention.
Figure 57:
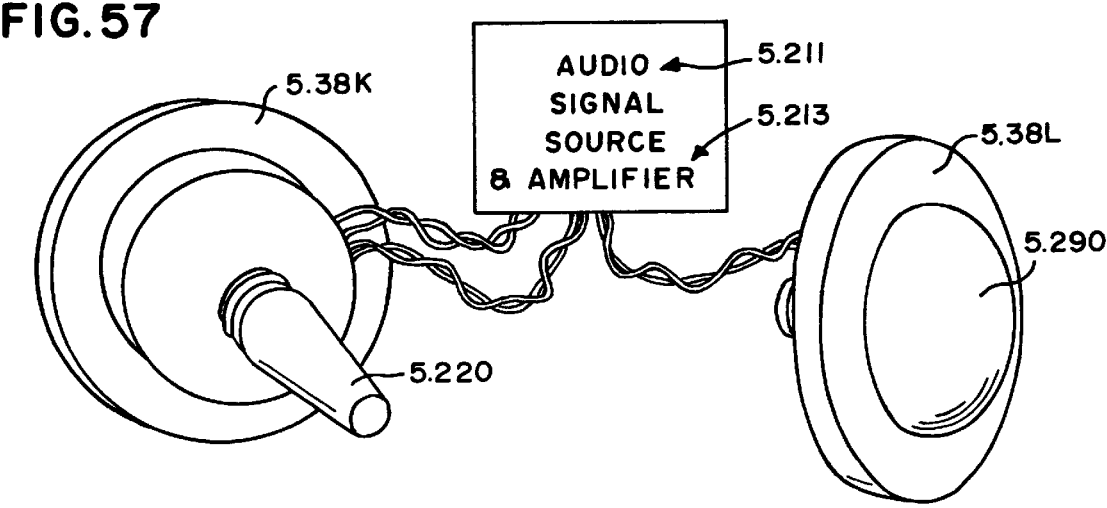
FIG. 57 shows a perspective and schematic view of a second version of audio earpieces with ear microphones for use with the fifth embodiment of the present invention.
Figure 58:
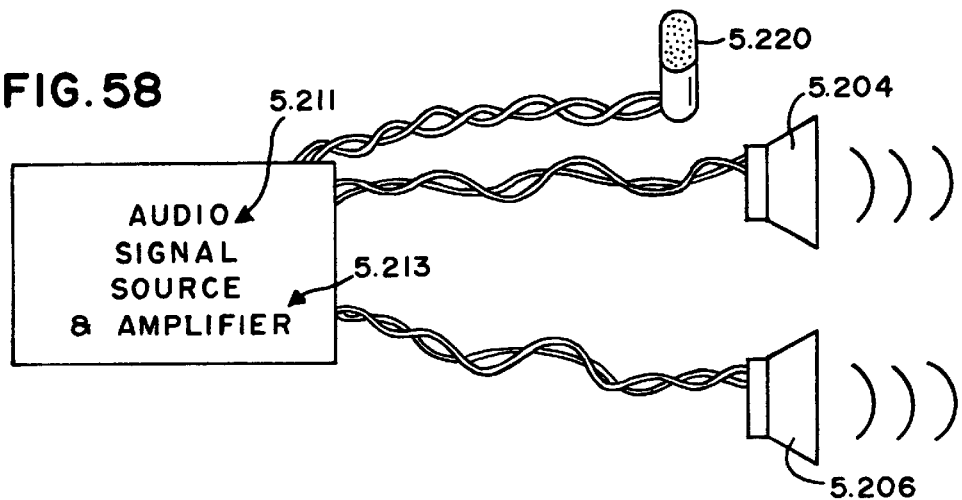
FIG. 58 is a schematic of the audio earpieces with ear microphones shown in FIGS. 56 and 57.

A fifth preferred embodiment 5.20 is shown in FIGS. 23–63 and 67, with identifying reference designators marked similarly to the prior embodiments, except with the prefix "5." It shall be understood that many aspects of all embodiments are substantially the same, and only the differences will be treated in detail. FIGS. 23–32 show the common features of all variations of the fifth embodiment. FIGS. 33–41 show variations of the rear end of the temples of the fifth embodiment. FIGS. 42–55 show variations of earpieces/earplugs and earpiece mounting and adjustment variations, while FIGS. 56–58 show a variation of the fifth embodiment in which audio earpieces and an ear microphone may be used with the fifth embodiment.

The eyewear 5.20 of the fifth embodiment comprises a front guard portion 5.22 including a resilient elongated member or front frame browpiece portion 5.32 and first and second temples 5.44, 5.52 slidably attached to the browpiece portion 5.32. The front end 5.46, 5.54 of the temples 5.44, 5.52 are slidably received onto browpiece portion 5.32 of the frame by first and second temple spread-and-length adjustment means 5.158, 5.160 for adjusting the spread and length of the temples so as to accommodate the differing physical features of different wearers and to provide wearing comfort for the wearers. Temple spread-and-length adjustment means 5.158, 5.160 are for selectively adjusting a spread distance 5.196 between temples 5.44, 5.52 and are for selectively adjusting a length distance 5.198, 5.199 between front transparent panel 5.28 and rear ends 5.48, 5.56 of first and second temples 5.44, 5.52 as the temples are slidably received for selective adjustment onto browpiece 5.32. The rear ends 5.48, 5.56 of the rear temple portions 5.88, 5.124 of the temples 5.44, 5.52 have an earpiece or earplug 5.38, 5.40 attached thereto remote from front guard portion 5.22, in a manner hereinafter described, and the earpiece or earplug 5.38, 5.40 is insertingly received into the ear E of a wearer, as shown, for example in FIG. 67, preferably into the ear canal C or concha 207 of the wearer's ear, thereby supporting the eyewear 5.20 on the wearer's head without having over-the-ear rear portions of the temple, as shown best in FIG. 67. Single or dual lenses (clear or tinted) of front transparent panel 5.28 are mounted to the browpiece portion 5.32 as by preferably being received into a groove or slot 5.260 in the browpiece portion 5.32 as shown especially in FIG. 32.

The lenses of front transparent panel 5.28 and eyewear 5.20 are supported on the wearer's nose by a nosepiece or bridge portion 5.30 attached to the lenses of front transparent panel 5.28. The earpiece or earplug 5.38, 5.40, by its receipt into the wearer's ear, thus supports its temple 5.44, 5.52 upon the wearer's head without having any corresponding temple portion extending over the wearer's ear.

The two temples 5.44, 5.52 are substantially mirror images of each other, and a description of one and its interconnection with browpiece portion 5.32 will suffice for both. Likewise, the structures of the first and second temple spread-and-length adjustment means 5.158, 5.160 are substantially mirror images of each other, and a description of one will suffice for both.

Figure 30:
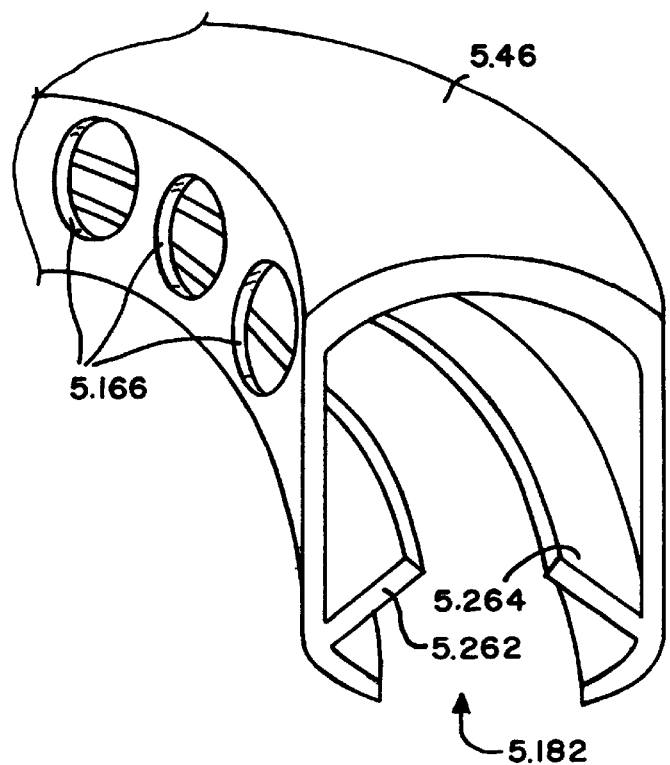
FIG. 30 is a perspective view of a front temple portion of the temples for the fifth embodiment of the present invention.
Figure 31:
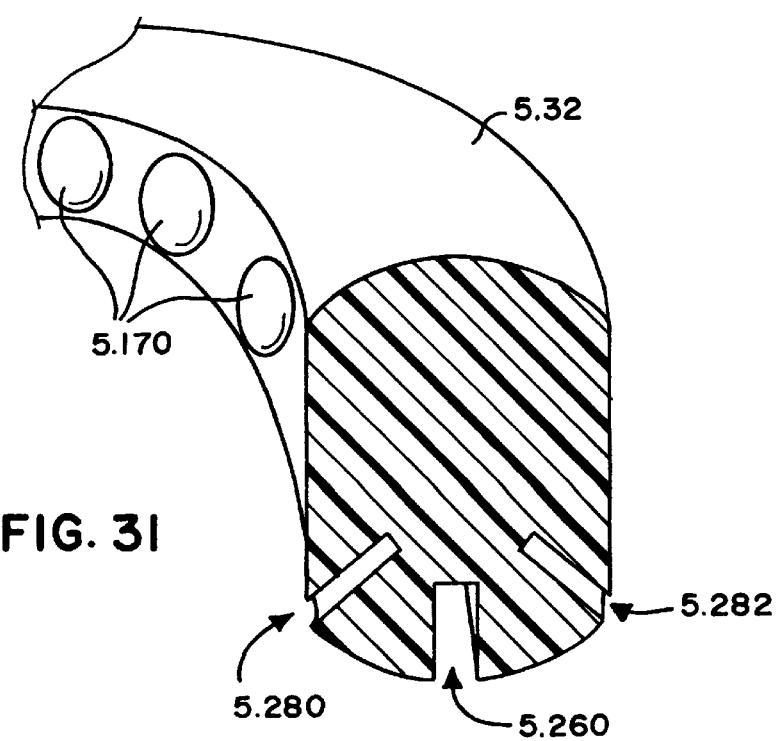
FIG. 31 is a sectional view of the front browpiece of the fifth embodiment of the present invention.

Referring to FIGS. 30–32, first temple spread-and-length adjustment means can now be described. The front end 5.46 of temple 5.44 is constructed as a curled sleeve having a downwardly-opening slot 5.182 for allowing the front transparent panel or lens 5.28 to longitudinally slidingly pass therethrough. A substantially similar slot 7.182 can be seen in FIG. 85, which shows a bottom view of a temple of the seventh embodiment, hereinafter described. The front end 5.46 of temple 5.44 is slidingly received onto browpiece portion 5.32. To minimize torquing or twisting of the temple 5.44, the inside of the front end of temple 5.44 has a pair of ribs 5.262, 5.264 that run longitudinally inside temple 5.44 and extend radially inwardly so as to engage and be closely received into mating longitudinal slots 5.280, 5.282 within browpiece 5.32 as temple 5.44 is slidingly received onto browpiece 5.32.

Browpiece portion 5.32 has dimples 5.170 on its rearward side that selectively engage and extend into the respective forward adjustment apertures 5.166, 5.168 of temples 5.44, 5.52. By longitudinally sliding temples 5.44, 5.52 with respect to browpiece portion 5.32, the dimples 5.170 will selectively engage their respective adjustment apertures, thereby providing selected positions of adjustment.

Adjustment means 5.158, 5.160 for temples 5.44, 5.52 allow adjustment of the spread and horizontal length of the temples 5.44, 5.52 to accommodate the various physical features of the head of the wearer. It shall be understood that the forward ends 5.46, 5.54 of temples 5.44, 5.52 are similarly curved to match with and be slidably received upon browpiece portion 5.32.

Temples 5.44, 5.52 are preferably formed so that the rearward ends 5.46, 5.48 are inwardly displaced towards each other and lower than the browpiece portion 5.32, and are further angled slightly upward to facilitate placement of earpieces 5.38, 5.40 into the wearer's ears. This structural alignment and forming of the concha-supported temples is common to all embodiments of the present invention.

Figure 24:
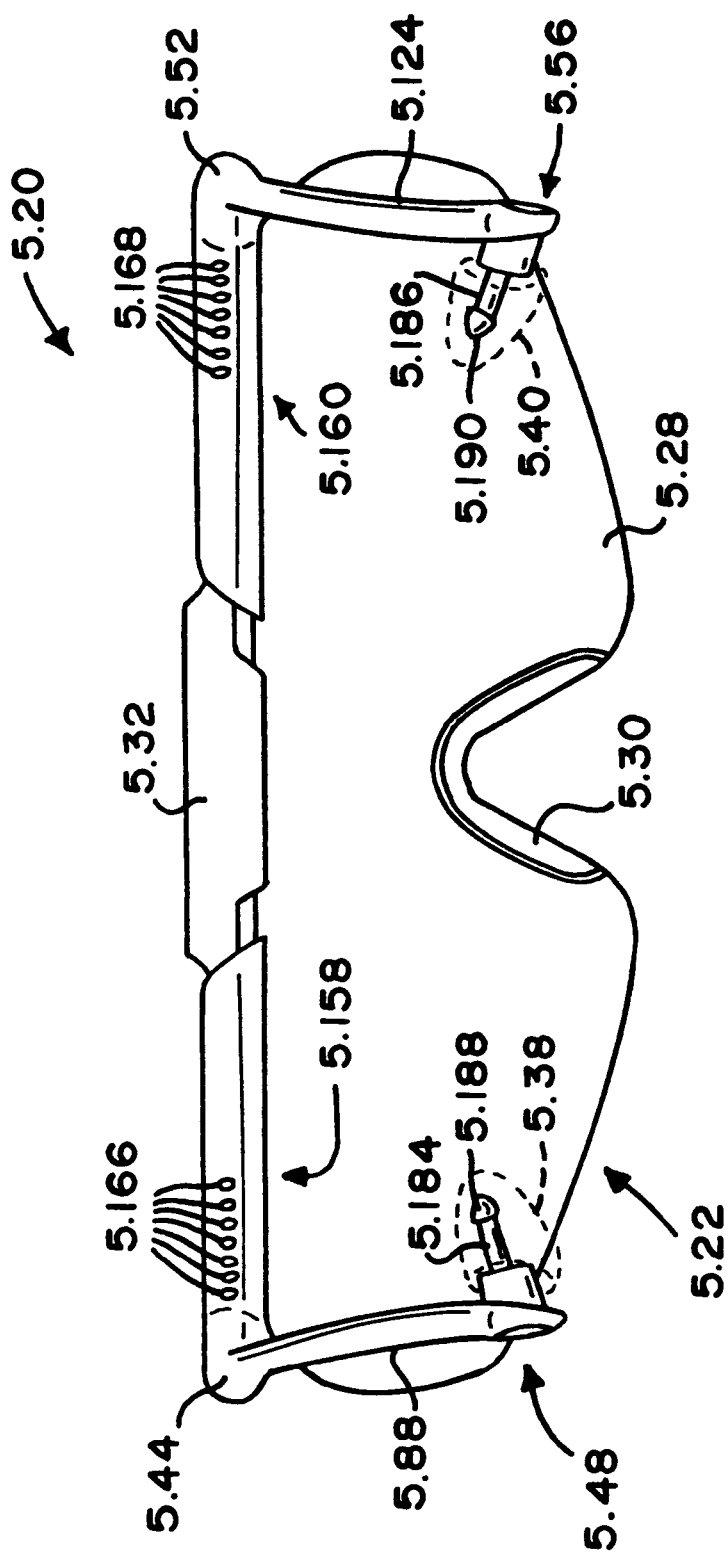
FIG. 24 is a rear view of the fifth embodiment of the present invention with a first version of the earpieces attached and shown in dotted outline.
Figure 25:
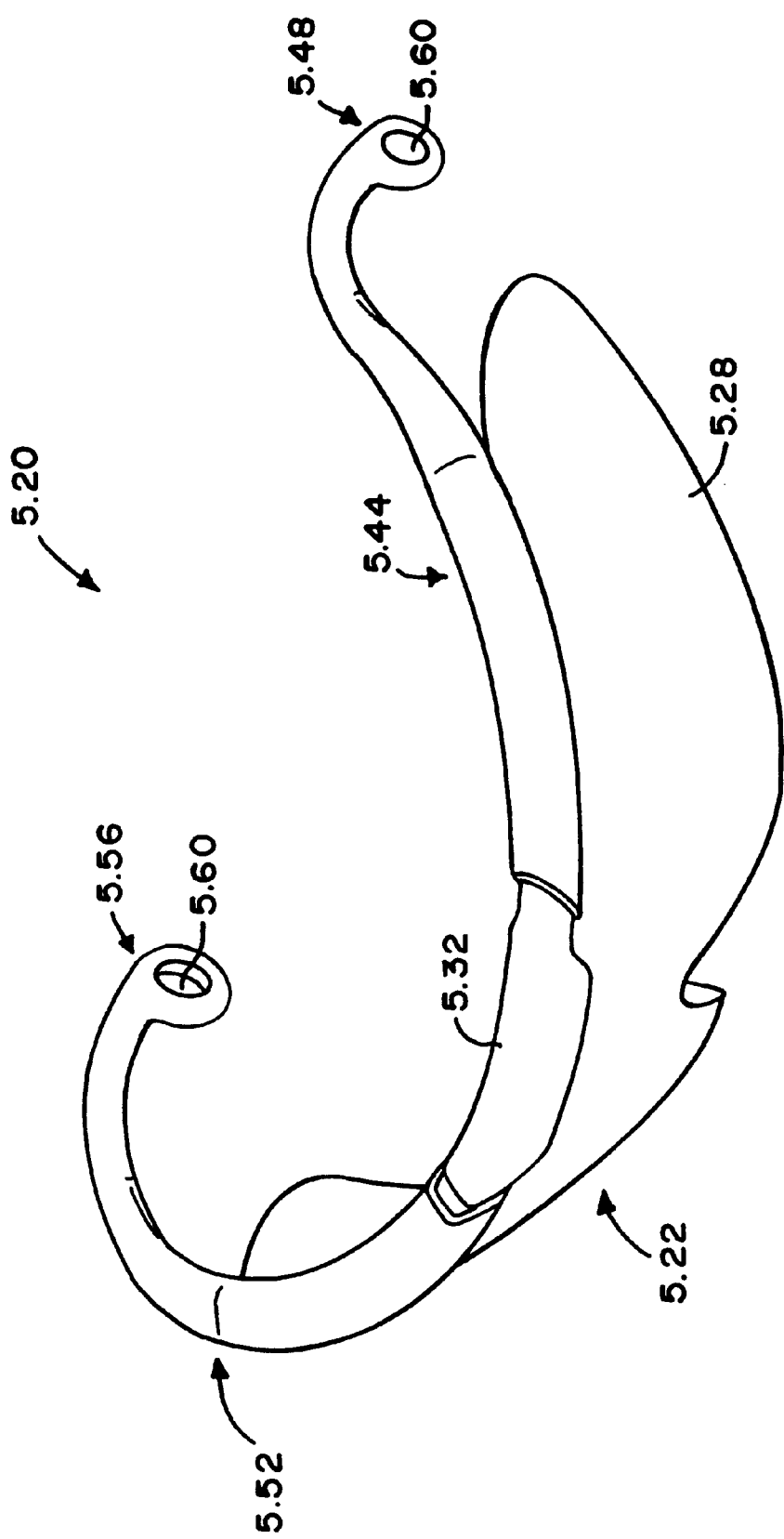
FIG. 25 is a perspective view from one direction of the fifth embodiment of the present invention with the rear earpieces removed.
Figure 26:
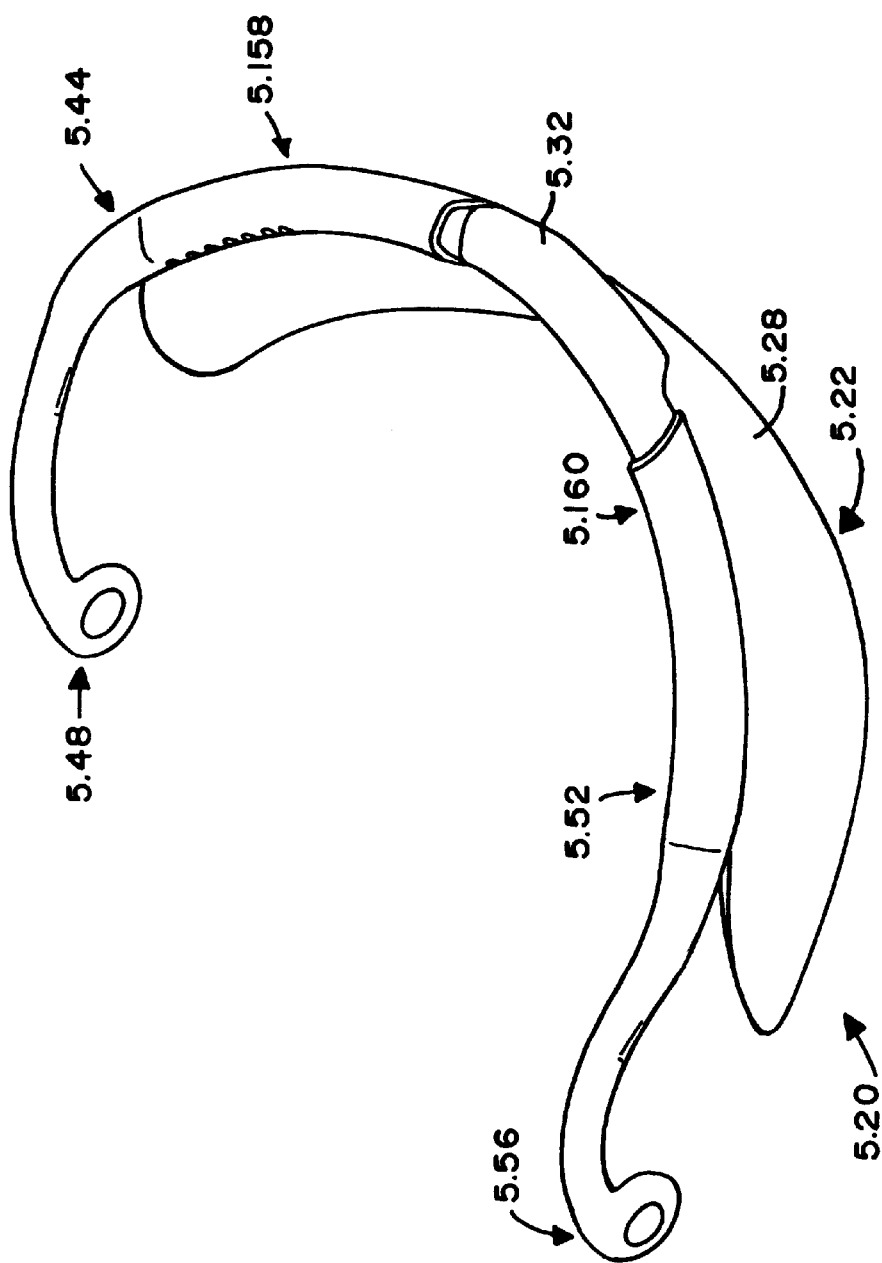
FIG. 26 is another perspective view from another direction of the fifth embodiment of the present invention with the rear earpieces removed.

Earplug or earpiece 5.38, 5.40 is received onto a barb 5.184, 5.186 on respective rearward portions 5.88, 5.124 of temples 5.44, 5.52, with barbs 5.184, 5.186 preferably having enlarged tips 5.188, 5.190 for retaining the respective earplugs or earpieces thereon. It shall also be understood that the earpieces/earplugs 5.38 and 5.40 shown in FIG. 24 are shown in dotted outline so as to reveal the hidden structure of the barb on which the earpieces are received. It shall be further understood that earpieces/earplugs 5.38 and 5.40, as well as barbs 5.184 and 5.186, are but one variant of the barbs and earpieces that may be used with the fifth embodiment, and other variations are described later.

FIGS. 33–41 show variations of the rear end of the temples of the fifth embodiment. It shall be understood that all of these variations are equally applicable to both the left and right temples, with the form of the variation for the right temples being a mirror image of the left temples shown in FIGS. 33–41, and, for this reason, a description of the left temple forms of variations will suffice for the right temple forms of the temple variations. It should be further understood that the front temple ends of all of these variations are identical for mating with browpiece portion 5.32 as heretofore described for temple 5.44.

A first temple variation 5.44A is shown in FIGS. 33–37. The rearward portion 5.88A of temple 5.44A has a fixed, non-adjustable spherical tip 5.188A on barb 5.184A onto which an earpiece 5.38A having a spherical cavity 5.266A is received through a rearward-opening bore 5.268A, thereby allowing earpiece 5.38A to slightly and adjustably "rock" into proper comfort alignment as the eyewear is placed on a wearer's head with the earpiece 5.38A resting in the concha of the wearer's ear.

Figure 38:
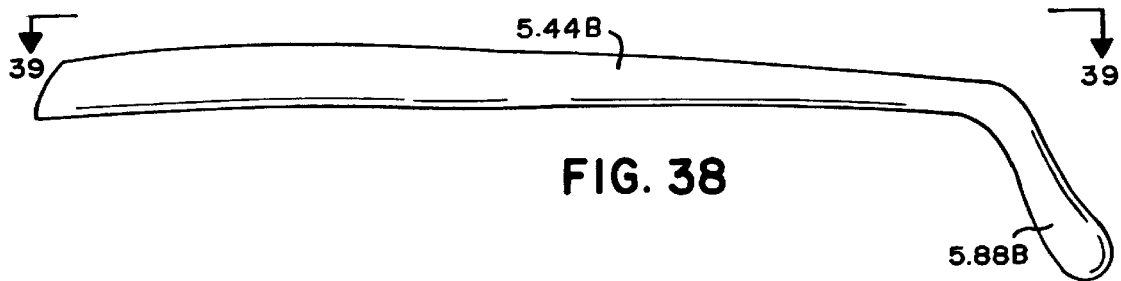
FIG. 38 is a side view of a second alternate temple for the fifth embodiment of the present invention.
Figure 39:
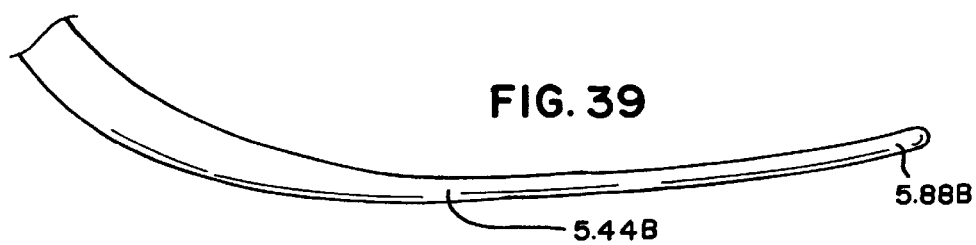
FIG. 39 is a top view of the second alternate temple for the fifth embodiment of the present invention, taken substantially along the line 39—39 shown in FIG. 38.
Figure 40:
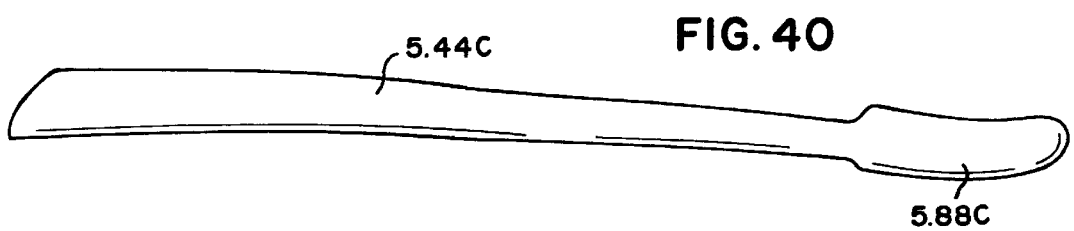
FIG. 40 is a side view of a third alternate temple for the fifth embodiment of the present invention.
Figure 41:
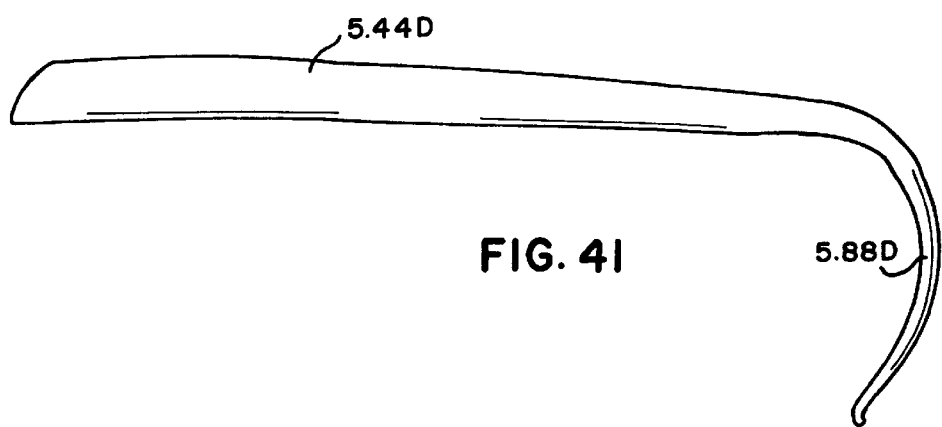
FIG. 41 is a side view of a fourth alternate temple for the fifth embodiment of the present invention.

FIGS. 38–41 show three alternative temples 5.44B, 5.44C, and 5.44D that allow the temple to be supported over the ear in the conventional manner. Such alternative temples may be provided when, for some reason such as to allow use of a telephone concurrent with the present invention, only one temple is desired to rest in, not over, the ear, with the other temple being supported over the top of the ear. FIG. 38 shows a side view and FIG. 39 shows a top view of an alternative temple 5.44B. The rear portion 5.88B of temple 5.44B loops over and downward behind the ear. FIG. 40 shows a side view of an alternative temple 5.44C. The rear portion 5.88C of temple 5.44C rests atop the ear adjacent the scalp. FIG. 40 shows a side view of an alternative temple 5.44D. The rear portion 5.88D of temple 5.44D hooks over and downward behind the ear. The present invention requires that at least one of the temples is not supported over the ear and is instead received into the concha of the respective ear and, with some variations of earplugs or earpieces, into the ear canal.

FIGS. 42–55 show variations of earpieces / earplugs and earpiece mounting and adjustment variations. It shall be understood that all of these variations are equally applicable to both the left and right temples, with the form of the variation for the right temples being a mirror image of the left temple forms shown in FIGS. 42–55, and, for this reason, a description of the left temple forms of variations will suffice for the right temple forms of the variations.

Figure 53:
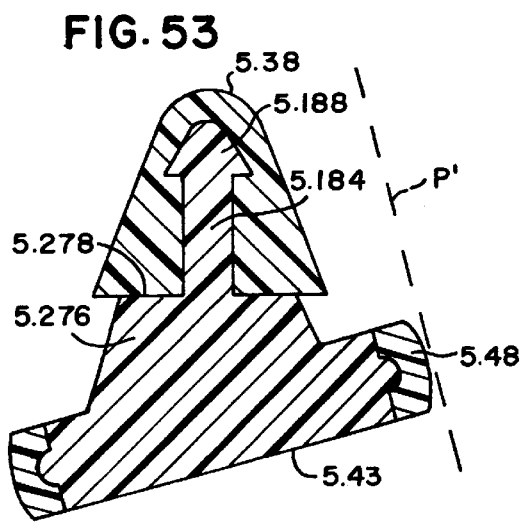
FIG. 53 is a sectional view showing the earplug of FIGS. 49–51 placed onto the earplug barb shown in FIG. 42.

The first preferred earpiece mounting means 5.252 is that shown in FIGS. 23–29, 42–44, 46, and 53. In this first preferred variation, the rear end 5.48 of temple 5.44 has an enlarged bore 5.60 therethrough into which a cylindrical post 5.43 is received, with cylindrical post 5.43 having a circumferential ridge 5.272 therearound that engages an inner circumferential groove 5.274 within bore 5.60. An angled barb 5.184 having a pointed tip 5.188 sits atop a frusto-conical base 5.276, with frusto-conical base 5.276 having a top plane 5.278 that is perpendicular to the axis of barb 5.184 and preferably angled at a non-zero planar angle so that barb 5.184 is not perpendicular to the axis of post 5.43. An earplug or earpiece 5.38 can be received onto barb 5.184 as shown in FIG. 53. It shall be understood that by rotating post 5.43 within bore 5.60 (compare FIG. 42 with FIG. 43), the angle of barb 5.184 can be adjusted for comfort within the wearer's ear.

Figure 42:
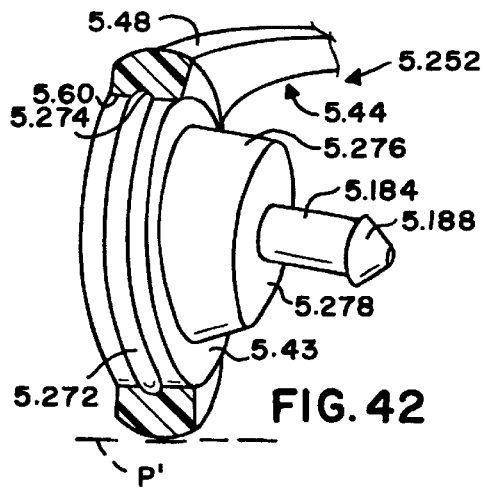
FIGS. 42–48 show various details of the earpiece mounting means of the fifth embodiment.
Figure 43:
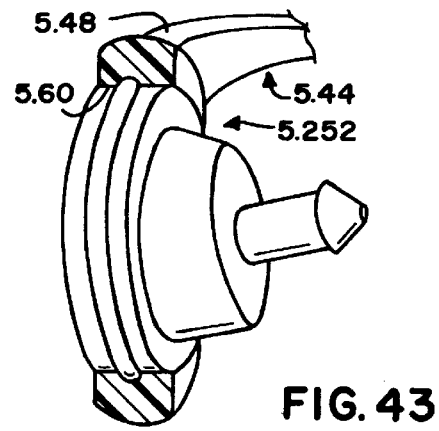
Figure 44:
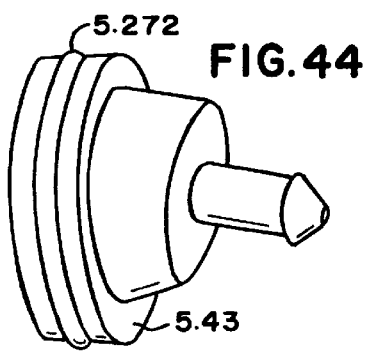
Figure 45:
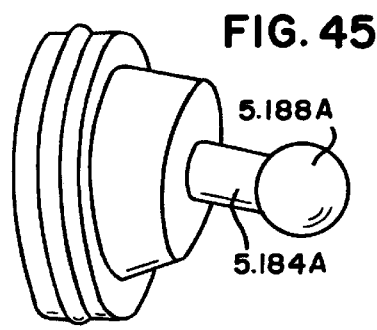
Figure 46:
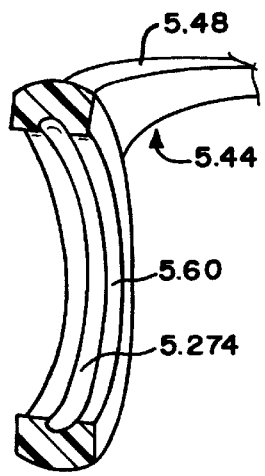
Figure 54:
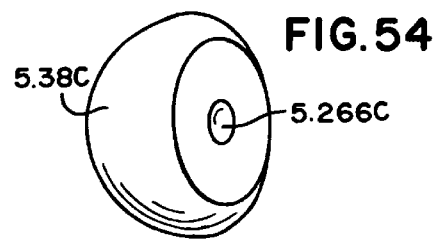
FIG. 54 is a perspective view of a semi-aural earplug of the present invention.
Figure 55:
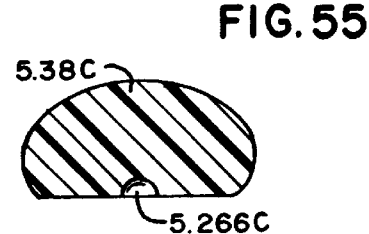
FIG. 55 is a sectional view of the semi-aural earplug shown in FIG. 54 as taken along a diameter, it being understood that the earplug is substantially cylindrically symmetrical.

FIG. 45 shows a variation of the earpiece mounting means in which barb 5.184A has a spherical tip 5.188A for receiving earplugs and earpieces of the type shown in FIGS. 54 and 55. Otherwise, the variation is as shown in FIGS. 42–44.

Figure 47:
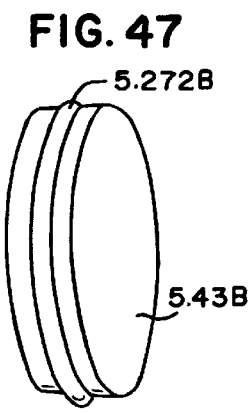
Figure 48:
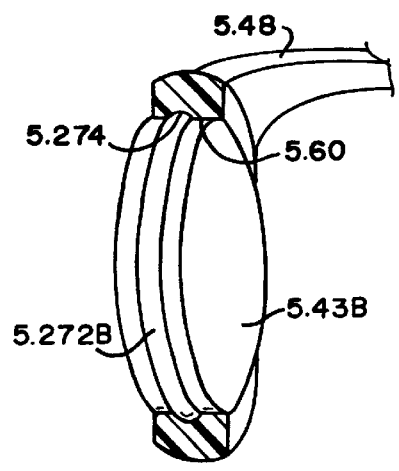

FIGS. 47 and 48 show a variation of the earpiece mounting means in which no plugging or blocking of the ear canal is desired, and a "support-only" comfort pad or disk earpiece 5.43B having only a circumferential ridge 5.272B and no frusto-conical base and no barb is received into bore 5.60 so as to allow the eyewear to be comfortably worn on the head and for the temple to terminate in the concha of the ear without plugging the ear canal.

All of the variations of the earpiece mountings shown in FIGS. 42–48 are preferably constructed of resilient plastic.

FIGS. 49–55 show variations of earpieces and earplugs. It shall be understood that all of these variations are equally applicable for use with both the left and right temples, with the form of the variation for the right temples being a mirror image of the left temple forms shown in FIGS. 49–55, and, for this reason, a description of the left temple forms of variations will suffice for the right temple forms of the variations.

Figure 49:
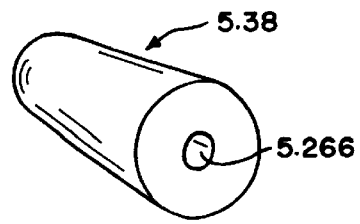
FIG. 49 is a rear perspective view of a first version of an aural earplug for the fifth embodiment of the present invention.
Figure 50:
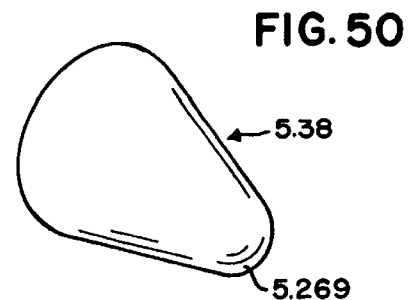
FIG. 50 is a front perspective view of the first version of the aural earplug shown in FIG. 49.
Figure 51:
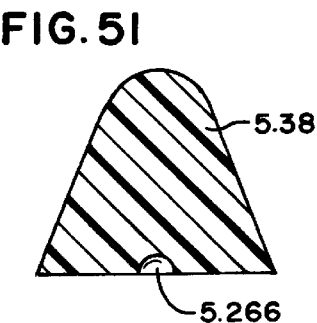
FIG. 51 is a sectional view of the first version of the aural earplug shown in FIGS. 49 and 50, as taken along a diameter, it being understood that the earplug is substantially cylindrically symmetrical.

FIGS. 49–51 show a first version of an aural earplug 5.38 that would be used to enter and sealingly block the ear canal of the wearer. Earplug 5.38 is generally conical and is cylindrically-symmetrical, having a blunt nose 5.269 and a slight cavity 5.266 for mating receipt with tip 5.188 of barb 5.184 as shown in FIG. 53. It shall be understood that, as earplug 5.38 is forcibly urged onto barb 5.184, tip 5.188 displacingly pierces earplug 5.38 until earplug 5.38 is fully received onto barb 5.184 as shown in FIG. 53.

Figure 52:
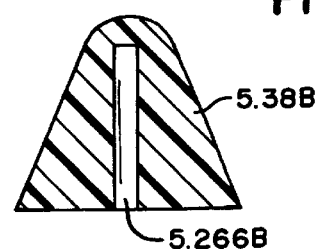
FIG. 52 is a sectional view of a variation of the first version of the aural earplug shown in Pigs. 49 and 50 as taken along a diameter, it being understood that the earplug is substantially cylindrically symmetrical.

FIG. 52 is a cross section of a variant 5.38B of aural earplug 5.38. The only difference between earplug 5.38B and earplug 5.38 is that the cavity 5.266B within earplug 5.38B extends further into the body of earplug 5.38B than does the cavity 5.266 of earplug 5.38. After placement onto barb 5.184, earplug 5.38B has substantially similar structure as shown in FIG. 53 for earplug 5.38, although earplug 5.38B would typically be used on a longer length barb than would earplug 5.38.

FIGS. 54 and 55 show a cylindrically-symmetrical semi-aural earplug 5.38C as would be used to only partially enter the outer ear canal and would sealingly block the entrance to the ear canal at the concha. Earplug 5.38C is seen to have a relatively shallow cavity 5.266C, and thus would be suitable for use with a relatively shorter length barb than would earplug 5.38B.

For all of the earpieces and earplugs shown in FIGS. 34–36 and 49–55, the earplugs/earpieces are readily disposed for sanitary reasons or to allow sharing of eyewear 5.20 among different persons, and only the earplug/earpiece material is discarded.

FIGS. 59–63 show variations of earpieces and earplugs in which the earpiece or earplug is integral with the cylindrical post with circumferential ridge. In all of the variations shown in FIGS. 59–63 it should be noted that the cylindrical post is positioned off-axis of the earpiece/earplug so that rotation of the cylindrical post allows fine adjustment of the positioning of the earpiece/earplug within the wearer's ear because of the orbital movement of the earpiece/earplug about the axis of the cylindrical post as the cylindrical post is axially rotated within bore 5.60. It shall be understood that all of these variations are equally applicable for use with both the left and right temples, with the form of the variation for the right temples being a mirror image of the left temple forms shown in FIGS. 59–63, and, for this reason, a description of the left temple forms of variations will suffice for the right temple forms of the variations.

Figure 59:
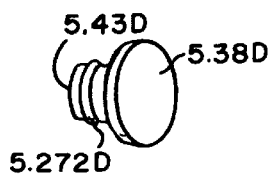
FIG. 59 is a perspective view from one direction of an adjustable comfort disk earpiece for use with the fifth embodiment of the present invention.
Figure 60:
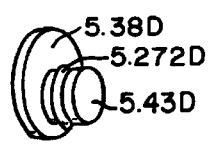
FIG. 60 is another perspective view of the adjustable comfort disk earpiece shown in FIG. 59.

FIGS. 59 and 60 show a variation of the earpiece mounting means in which no plugging or blocking of the ear canal is desired, and an enlarged "support-only" comfort pad or disk earpiece 5.38D having a cylindrical post 5.43D with only a circumferential ridge 5.272D and no frusto-conical base and no barb is received into bore 5.60 so as to allow the eyewear to be comfortably worn on the head and for the temple to terminate in the concha of the ear without plugging the ear canal. Because the disk is off-axis of the post 5.43D, rotation of post 5.43D within bore 5.60 allows the disk to be adjusted for comfort.

Figure 61:
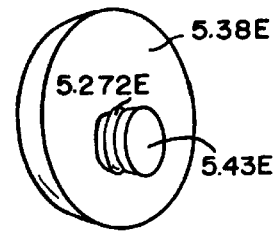
FIG. 61 is a rear perspective view of a semi-aural earplug with integral earpiece mounting means for use with the fifth embodiment of the present invention.

FIG. 61 shows a cylindrically-symmetric semi-aural earplug 5.38E that is molded around cylindrical post 5.43E with a circumferential ridge 5.272E. Because the earplug 5.38 E is off-axis of the post 5.43E, rotation of post 5.43E within bore 5.60 allows the earplug to be adjusted for comfort.

Figure 62:
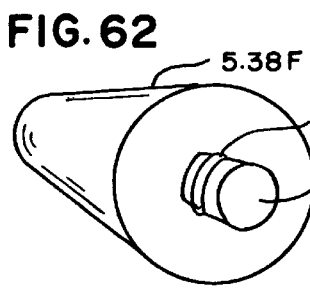
FIG. 62 is a rear perspective view of a first aural earplug with integral earpiece mounting means for use with the fifth embodiment of the present invention.
Figure 63:
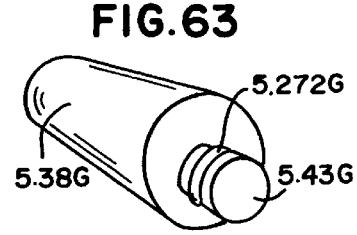
FIG. 63 is a rear perspective view of a second aural earplug with integral earpiece mounting means for use with the fifth embodiment of the present invention.
Figure 64:
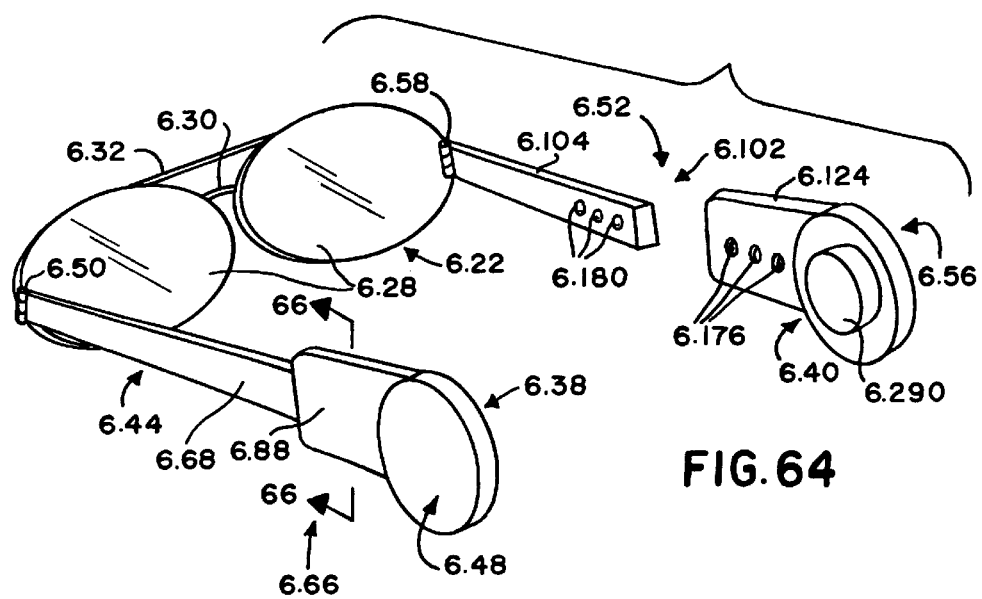
FIG. 64 is a perspective view of a sixth embodiment of the present invention without audio earpieces.
Figure 65:
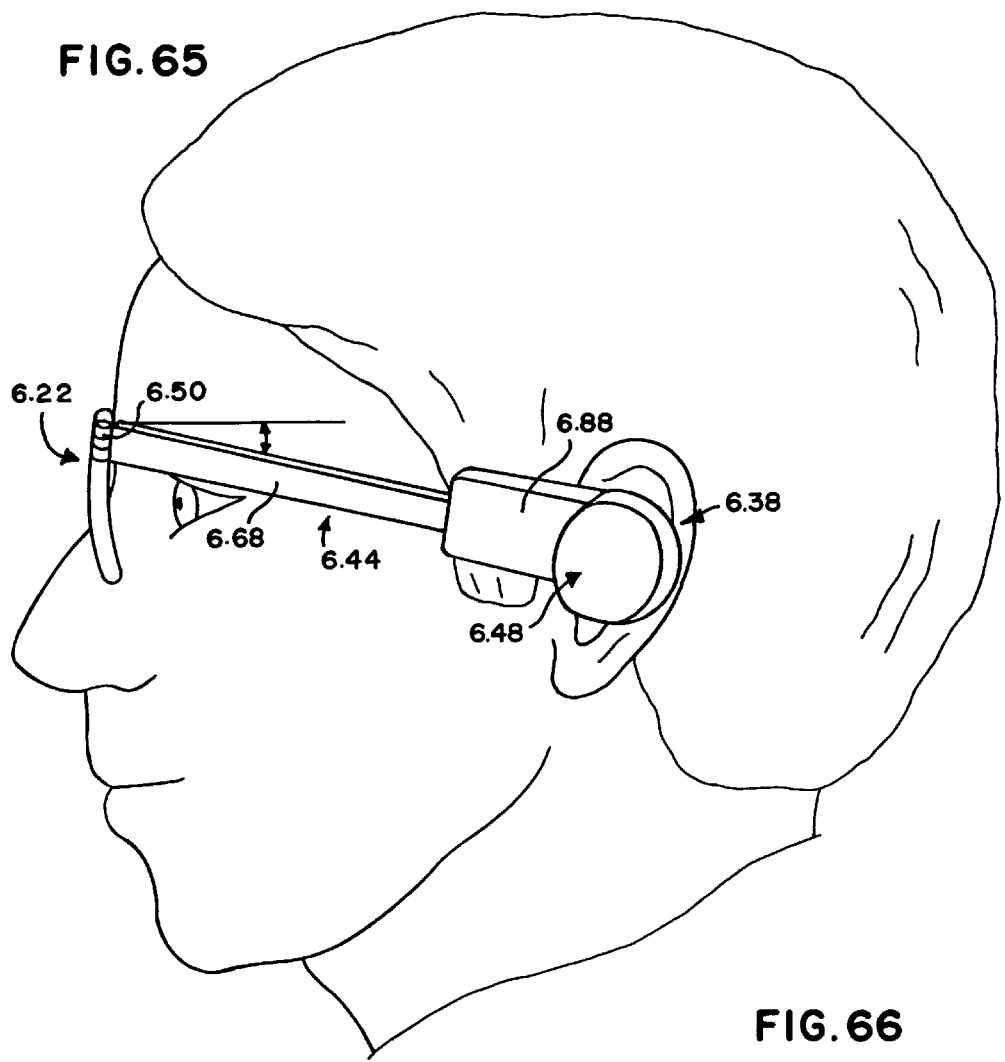
FIG. 65 is a side view showing a wearer wearing the sixth embodiment of the present invention.
Figure 64A:
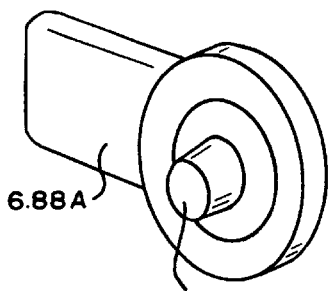
FIG. 64A is a perspective view showing an audio earpiece with ear microphone for the sixth embodiment of the present invention.
Figure 66:
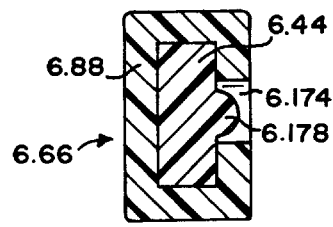
FIG. 66 is a transverse sectional view showing the temple length adjustment means of the sixth embodiment taken substantially along the line 66—66 shown in FIG. 64.
Figure 67:
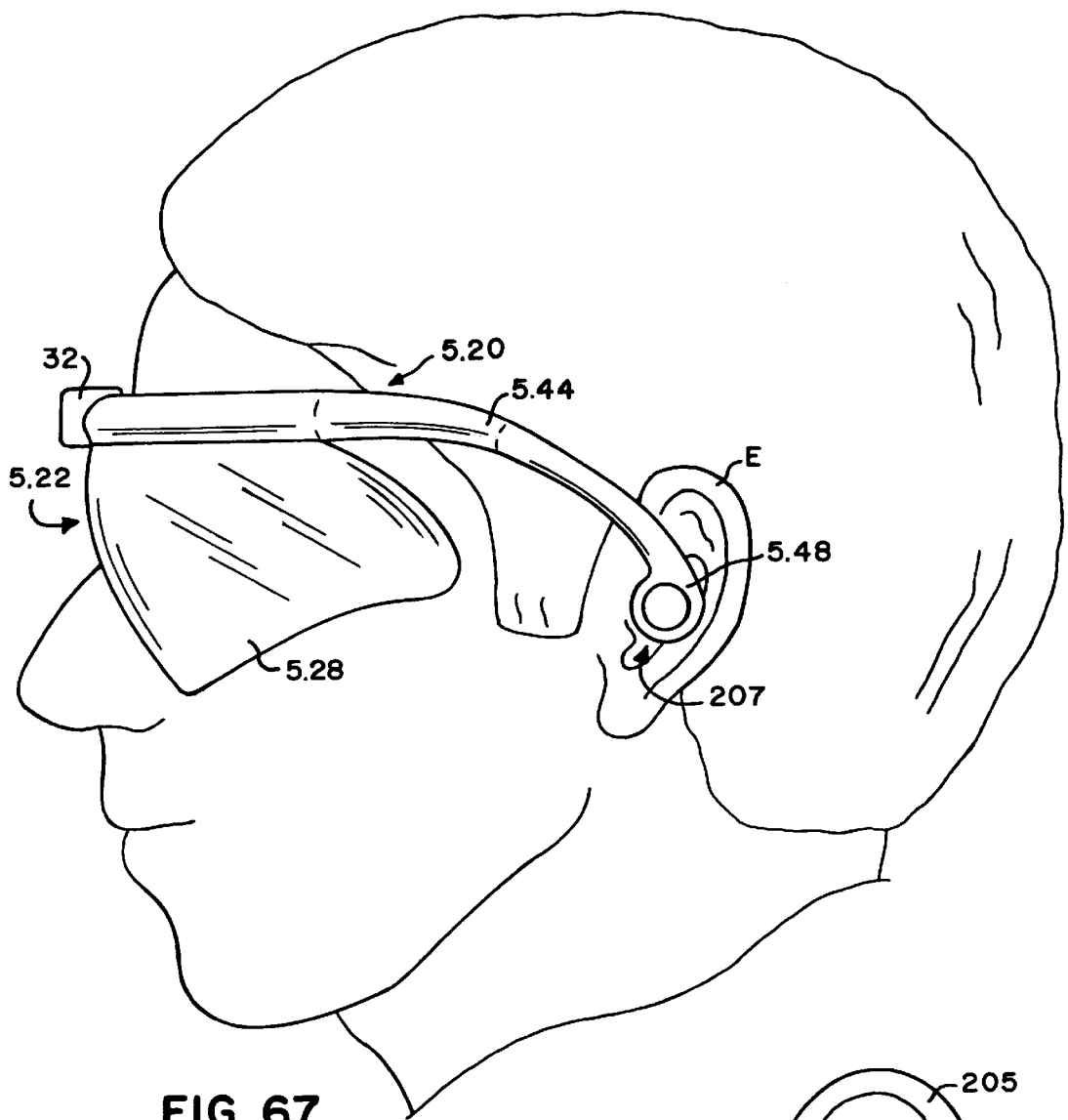
FIG. 67 is a side view showing a wearer wearing the fifth embodiment of the present invention.

FIGS. 62 and 63 show two similar cylindrically-symmetric aural earplugs 5.38F and 5.38G that differ only in the taper and thickness. Because the earplugs 5.38F, 5.38G are off-axis of their respective posts 5.43 F, 5.43G, rotation of posts 5.43F, 5.43G within bore 5.60 allows the earplugs to be adjusted for comfort.

FIGS. 56–58 show a variation of the fifth embodiment in which audio earphone earpieces and an ear microphone may be used with the fifth embodiment. As with the second, third, and fourth embodiments, it shall be understood that the audio earphone earpieces can be mixed and matched with the other variants of earpieces so that none, one or both of the earpieces could have audio earphone earpieces. Likewise, none, one or both of the earpieces could have an ear microphone as hereinafter described, although FIGS. 56–58 show the example situation where both earpieces are audio earphone earpieces and only one of the earpieces has an ear microphone.

FIGS. 56 and 58 show well-known first earphone means 5.204 for converting a first electrical signal from well-known audio source 5.211 to sound within first earpiece 5.38H and also show well-known second earphone means 5.206 for converting a second electrical signal from well-known audio source 5.211 to sound within second earpiece 5.38J. Likewise, first earphone earpiece 5.38K of FIG. 57 has similar well-known first earphone means therewithin for converting a first electrical signal from well-known audio source 5.211 to sound within first earphone earpiece 5.38K and also has a second earphone earpiece 5.38L with similar well-known second earphone means therewithin for converting a second electrical signal from well-known audio source 5.211 to sound within second earphone earpiece 5.38L. It shall be understood that the well-known schematic diagram of FIG. 58 suffices for an understanding of both FIGS. 56 and 58.

All of the earphone earpieces of FIGS. 58 and 58 have similar mounting posts for receipt into, e.g., bore 5.60 as heretofore explained in detail, it being understood as hereinbefore explained that a description of the earpiece mounting for one temple suffices for both. As with the earpieces of FIGS. 59–63, the mounting posts are preferably off-axis of the earphone earpieces 5.38H, 5.38J, 5.38K, and 5.38L so as to allow for comfort adjustment in a manner heretofore described.

One or both of the earphone earpieces may preferably include a well-known ear microphone 5.220 of the type disclosed in Mauney et al., U.S. Pat. No. 5,812,659 (issued Sep. 22, 1998), now fully incorporated herein by reference; Konomi, U.S. Pat. No. 4,588,867 (issued May 13, 1986), now fully incorporated herein by reference; and others. Such a well-known ear microphone is combined with the earphone to form a single unit without requiring a separate boom-mounted microphone.

Such a well-known ear microphone 5.220 also provides an added safety factor over a boom-style microphone. Certain work and recreational environments require communications via telephone, cellular telephone, two-way radio, intercom, or a public address system. Use of an ear microphone in such situations permits hands-free two-way communications while wearing the present invention.

Preferably, ear microphone 5.220 is mounted within a tapered housing as shown outboard of the earphone and on the mounting post of the earpiece as shown so as to pass through bore 5.60 during attachment of the earpiece mounting means therewithin, and the signal from ear microphone 5.220 passes over wires to well-known amplifier 5.213 for amplification thereby in a manner well-known to those skilled in the art. Ear microphone 5.220 acoustically isolates the earphone of the earpiece from the microphone, in a manner well-known to those skilled in the art, so as to avoid feedback.

Earphone earpiece 5.38H is substantially identical to earphone earpiece 5.38J, except that earphone earpiece 5.38J does not have an ear microphone 5.220. Likewise, earphone earpiece 5.38K is substantially identical to earphone earpiece 5.38L, except that earphone earpiece 5.38L does not have an ear microphone 5.220. Earphone earpieces 5.38H and 5.38J can either be of the well-known supra-aural shape that fit into the concha without entering the ear canal or can be of the well-known shape and construction that combine the noise attenuation benefits of an earplug with the introduction of audio into the ear canal of the wearer.

Earphone earpieces 5.38K and 5.38L are similar to earphone earpieces 5.38H and 5.38J except that earphone earpieces 5.38K and 5.38L are full ear speakers that fit over the full ear and have a retainer extension portion 5.290 that is sized for and fits within the wearer's concha. The larger surface area of earphone earpieces 5.38K and 5.38L as compared to 5.38H and 5.38J provides additional comfort for the wearer and permits a larger diaphragm for the ear speaker, thereby producing better audio reproduction quality.

All of the variants of earplugs or earpieces 5.38, 5.40, with the exception of "support-only" comfort pad or disk earpiece 5.43B, are preferably constructed of unfoamed poly-vinyl chloride ("PVC") plastisol, although other materials may be used as well.

Figure 27:
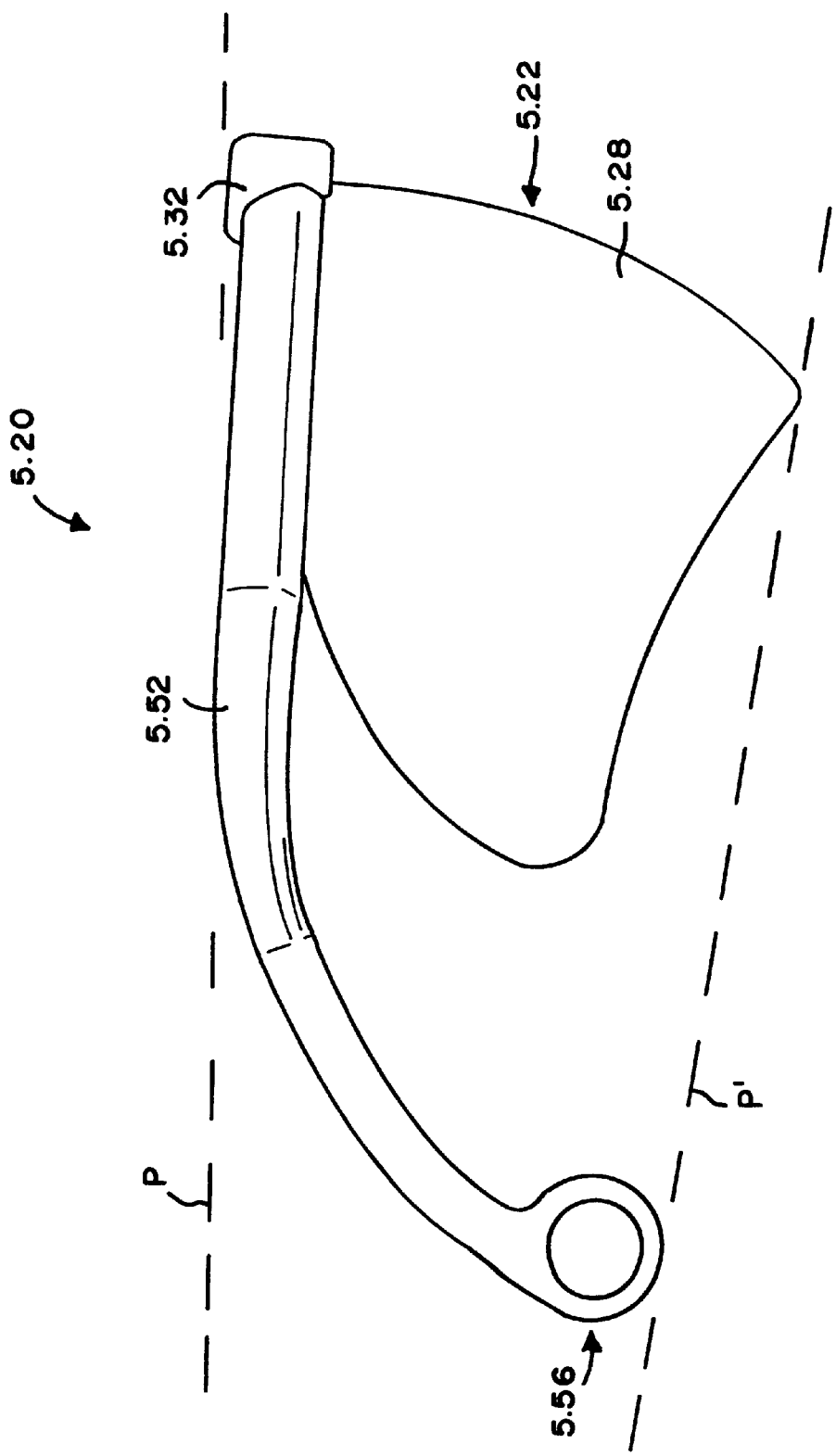
FIG. 27 is a side view of the fifth embodiment of the present invention with the rear earpieces removed. The view from the other side is a mirror image.
Figure 28:
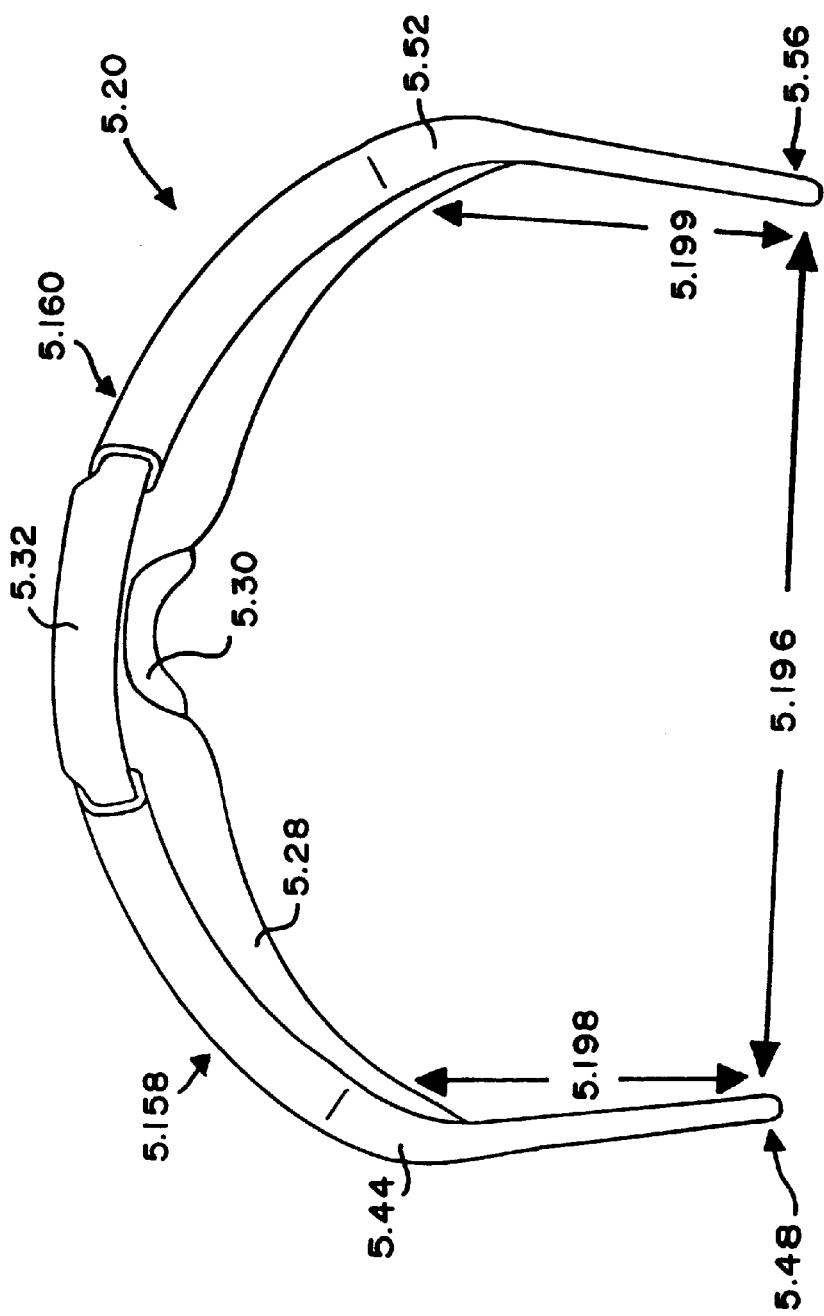
FIG. 28 is a top view of the fifth embodiment of the present invention with the rear earpieces removed.
Figure 29:
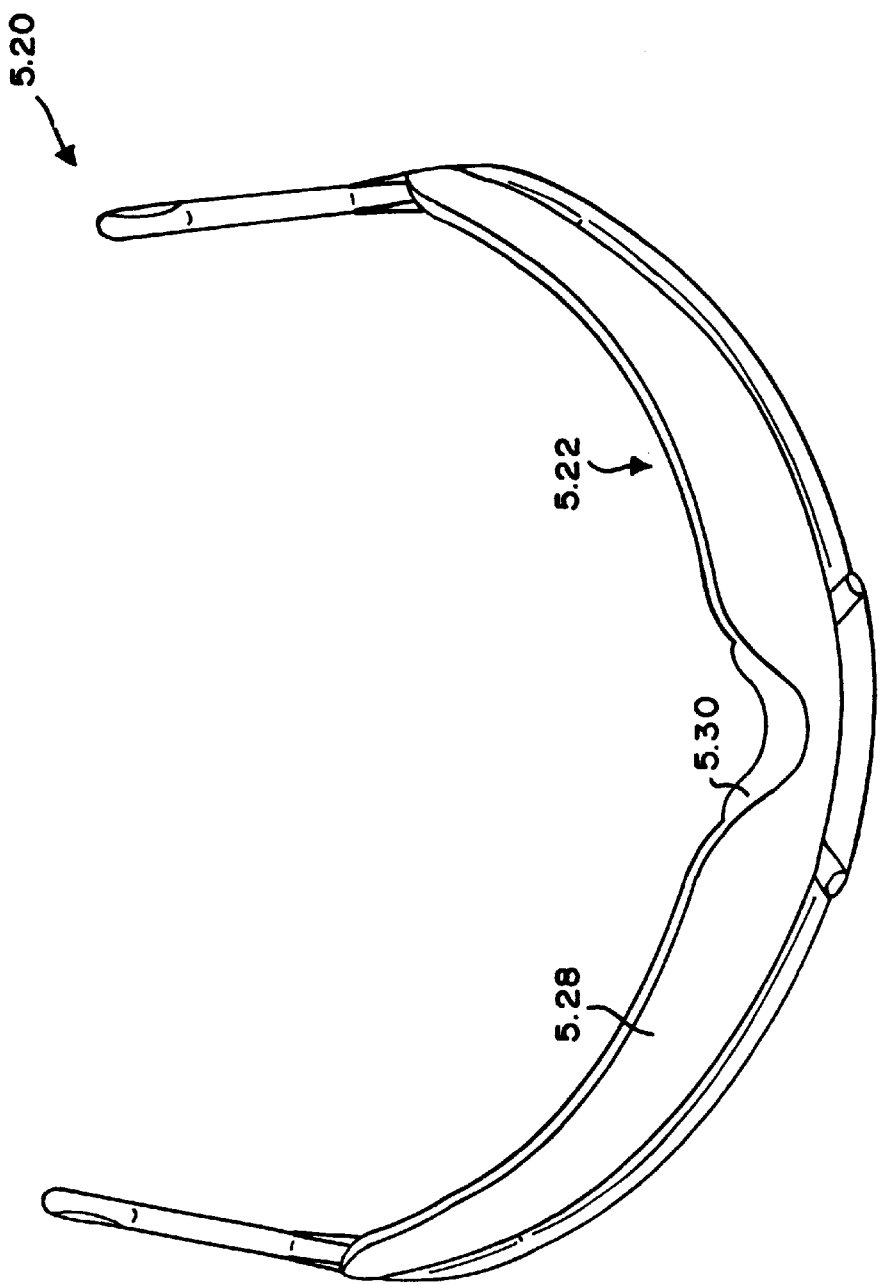
FIG. 29 is a bottom view of the fifth embodiment of the present invention with the rear earpieces removed.

As shown in FIGS. 27 and 53, the fifth embodiment is preferably constructed so that, for sanitary reasons, if the fifth embodiment is removed from the wearer's head and placed upside down on a table or plane P, or upright on a table or plane P', the upward angle of the earplug or earpiece 5.38 is such that the earpiece 5.38 does not contact the surface of the table, thereby preventing dust and debris from collecting on the surface of earpiece 5.38 for future insertion into the wearer's ear when the eyewear is replaced on the wearer's head. The seventh embodiment 7.20, hereinafter described, has this feature as well.

First and second temples 5.44, 5.52 are resilient and substantially shape-retaining, preferably being made of resilient plastic, and transmit the inward pressure created by the resilience of elongated browpiece portion 5.32 to rear temple portions 5.88, 5.124 which, in turn, exert an inwardly-directed force acting through earplugs 5.38, 5.40 (i.e., forcing the earplugs 5.38, 5.40 toward each other through the wearer's head), with the inwardly-directed force through each earplug being preferably at least about one Newton (about 3.6 ounces Avoirdupois) and with the inwardly-directed force through each earplug preferably being about 6 ounces Avoirdupois (1.67 Newtons) so as to comfortably secure the eyewear onto the wearer's head during physical activity. If earpiece 5.38, 5.40 is an aural, semi-aural, or supra-aural earplug, then this force also seals the earplug to the ear canal.

A sixth preferred embodiment 6.20 is shown in FIGS. 64, 64A, and 65–66, with identifying reference designators marked similarly to the prior embodiments, except with the prefix "6."

The sixth preferred embodiment 6.20 uses a well-known eyeglasses frontpiece or front guard portion 6.22 with hinged temple attachments 6.50, 6.58, but the hinges on the temples of the sixth embodiments are constructed so that the temples 6.44, 6.52 are angled substantially downwardly from the horizontal (see FIG. 65), as contrasted with the substantially horizontal temples of well-known eyeglasses, so that the temples can be supported within the ear in the manner of the present invention rather than by being supported over the ear as in prior art eyeglasses.

Like the first through third embodiments, the sixth embodiment 6.20 comprises a front guard portion 6.22 including a resilient elongated member or front frame browpiece portion 6.32 and first and second temples 6.44, 6.52 hingedly attached to the browpiece portion 6.32. The rear ends 6.48, 6.56 of the rear temple portions 6.88, 6.124 of the temples 6.44, 6.52 have an audio earphone earpiece 6.38, 6.40 attached thereto remote from front guard portion 6.22. Each earpiece 6.38, 6.40 preferably has a retainer extension portion 6.290 that is sized for and fits within the wearer's concha, thereby supporting the eyewear 6.20 on the wearer's head without having over-the-ear rear portions of the temple, as shown best in FIG. 65. Audio earpieces 6.38, 6.40 operate in a well-known manner, similar to earpieces 5.38H and 5.38J, heretofore described, to provide audio sounds for the wearer. If desired, an alternate rear temple portion 6.88A (see FIG. 64A) may be substituted for rear temple portion 6.88, and rear temple portion 6.88A is substantially similar to rear temple portion 6.88 except that rear temple portion 6.88A is provided with a well-known ear microphone 6.220 similar to ear microphone 5.220 heretofore described. Single or dual lenses 6.28 (clear or tinted) comprise a front transparent panel and are mounted to the browpiece portion 6.32 in a manner well-known to those skilled in the art, as by being secured within the front frame of the eyewear, and the lenses 6.28 and eyewear 6.20 are supported on the wearer's nose by a nosepiece or bridge portion 6.30 attached to the lenses 6.28.

The two temples 6.44, 6.52 are substantially mirror images of each other, and a description of one will suffice for both.

Temples 6.44, 6.52 respectively have rearward portions 6.88, 6.124 that are respectively slidably received over and onto the front portions 6.68, 6.104 of respective temples 6.44, 6.52, and dimples (e.g., dimples 6.180 for temple 6.52 and 6.178 for temple 6.44) on the inside side of front temple portions 6.68, 6.104 selectively engage and extend into the rearward adjustment apertures 6.174, 6.176 on the inside side of respective temple rearward portions 6.88, 6.124. These first and second temple length adjustment means 6.66, 6.102 (best seen in FIGS. 64 and 66), for respective temples 6.44, 6.52, allow adjustment of the length of temples 6.44, 6.52 so as to permit the earpiece 6.38, 6.40 to align with the wearer's ear canal or concha, both vertically and horizontally, by adjusting the length distance between front lenses 6.28 and rear ends 6.48, 6.56.

Earpieces 6.38, 6.40 are preferably constructed of unfoamed poly-vinyl chloride ("PVC") plastisol on their inner surface for contacting the wearer's ear, although other materials may be used as well.

The hinges 6.50, 6.58 of temples 6.44, 6.52 of the sixth embodiment are constructed so as to force the temples slightly inward toward the wearer's head and thereby exert inward pressure to retain the earpieces 6.38, 6.40 within the wearer's ear. First and second temples 6.44, 6.52 are resilient and substantially shape-retaining, preferably being made of resilient plastic, and transmit the inward pressure created by the hinges and by the resilience of elongated browpiece portion 6.32 to rear temple portions 6.88, 6.124 which, in turn, exert an inwardly-directed force acting through earpieces 6.38, 6.40 (i.e., forcing the earpieces 6.38, 6.40 toward each other through the wearer's head), with the inwardly-directed force through each earpiece being preferably at least about one Newton (about 3.6 ounces Avoirdupois) and with the inwardly-directed force through each earpiece preferably being about 6 ounces Avoirdupois (1.67 Newtons) so as to comfortably secure the eyewear onto the wearer's head during physical activity. If earpiece 6.38, 6.40 is an aural, semi-aural, or supra-aural earpiece, then this force also seals the earpiece to the ear canal.

A seventh preferred embodiment 7.20 is shown in FIGS. 69–75 and 83–85, with identifying reference designators marked similarly to the prior embodiments, except with the prefix "7.". An eighth preferred embodiment is shown in FIGS. 76–82 and 86–88, with identifying reference designators marked similarly to the prior embodiments, except with the prefix "8." It shall be understood that many aspects of all embodiments are substantially the same, and only the differences will be treated in detail. It shall also be understood that the earpieces/earplugs 7.38, 7.40, 8.38, and 8.40 shown in FIGS. 69–88 are shown in dotted outline so as to reveal the hidden structure of the barb on which the earpieces are received.

Seventh embodiment 7.20 is similar to the fifth embodiment heretofore described except that the seventh embodiment 7.20 adds rearward first and second temple length adjustment means 7.66, 7.102, as hereinafter described. Seventh embodiment 7.20 also shows that the barbs, on which the earplugs/earpieces are attached, may be at a fixed angle rather than at adjustable angles as in the fifth embodiment, but it should be understood that the barbs on the fifth, seventh, and eighth embodiments may be either fixed or adjustable, using the rear temple portions described herein or their equivalents.

The eyewear 7.20 of the seventh embodiment comprises a front guard portion 7.22 including a resilient elongated member or front frame browpiece portion 7.32 and first and second temples 7.44, 7.52 slidably attached to the browpiece portion 7.32. The front end 7.46, 7.54 of the temples 7.44, 7.52 are slidably received onto browpiece portion 7.32 of the frame by first and second temple spread-and-length adjustment means 7.158, 7.160 for adjusting the spread and length of the temples so as to accommodate the differing physical features of different wearers and to provide wearing comfort for the wearers. Temple spread-and-length adjustment means 7.158, 7.160 are for selectively adjusting a spread distance 7.196 between temples 7.44, 7.52 and are for selectively adjusting a length distance 7.198, 7.199 between front transparent panel 7.28 and rear ends 7.48, 7.56 of first and second temples 7.44, 7.52 as the temples are slidably received for selective adjustment onto browpiece 7.32. The temples of seventh embodiment 7.20 may have a plurality of ornamental raised ridges 7.162, 7.164 thereupon. The rear ends 7.48, 7.56 of the rear temple portions 7.88, 7.124 of the temples 7.44, 7.52 have an earpiece or earplug 7.38, 7.40 attached thereto remote from front guard portion 7.22, and the earpiece or earplug 7.38, 7.40 is insertingly received into the ear E of a wearer, preferably into the ear canal C or concha 207 of the wearer's ear, thereby supporting the eyewear 7.20 on the wearer's head without having over-the-ear rear portions of the temple, as shown best in FIG. 73. It shall be understood that the mounting of the seventh embodiment 7.20 on the wearer's head is substantially similar and has a similar appearance to the mounting and wearing of the fifth embodiment 5.20 shown in FIG. 67. Single or dual lenses (clear or tinted) of front transparent panel 7.28 are mounted to the browpiece portion 7.32 as by preferably being received into a groove or slot in the browpiece portion 7.32 in a manner substantially as shown in FIG. 32 for the fifth embodiment 5.20, it being understood that FIGS. 30–32 and the accompanying disclosure of the fifth embodiment 5.20 apply equally well to this seventh embodiment 7.20, and the lenses of front transparent panel 7.28 and eyewear 7.20 are supported on the wearer's nose by a nosepiece or bridge portion 7.30 attached to the lenses of front transparent panel 7.28. The earpiece or earplug 7.38, 7.40, by its receipt into the wearer's ear, thus supports its temple 7.44, 7.52 upon the wearer's head without having any corresponding temple portion extending over the wearer's ear.

The two temples 7.44, 7.52 are substantially mirror images of each other, and a description of one and its interconnection with browpiece portion 7.32 will suffice for both.

Browpiece portion 7.32 has dimples (not shown, but see related Pigs. 30–32 of the fifth embodiment) on its rearward side that selectively engage and extend into the forward adjustment apertures 7.166, 7.168 on temples 7.44, 7.52, with temple spread-and-length adjustment means 7.158, 7.160 being substantially structurally similar to the temple spread-and-length adjustment means of the fifth embodiment shown in FIGS. 30–32. Adjustment means 7.158, 7.160 for temples 7.44, 7.52 allow adjustment of the spread and horizontal length of the temples 7.44, 7.52 to accommodate the various physical features of the head of the wearer. It shall be understood that the forward ends 7.46, 7.54 of temples 7.44, 7.52 are similarly curved to match with and be slidably received upon browpiece portion 7.32, and each temple is provided with a slot 7.182 (as shown in FIG. 85 for temple 7.44) for allowing the temple to slide past the front transparent panel or lens 7.28 as the spread of the temples is adjusted.

Temples 7.44, 7.52 respectively have rearward portions 7.88, 7.124 that are respectively slidably received into the front portions 7.68, 7.104 of respective temples 7.44, 7.52, and dimples (e.g., dimples 7.178 for temple 7.44) on the inside side of temple rearward portions 7.88, 7.124 selectively engage and extend into the rearward adjustment apertures 7.174, 7.176 on the inside side of respective temple front portions 7.68, 7.104. These first and second temple length adjustment means 7.66, 7.102 (best seen in detail in FIGS. 83–84 for length adjustment means 7.66), for respective temples 7.44, 7.52, allow adjustment of the length of temples 7.44, 7.52 so as to permit the earplug or earpiece 7.38, 7.40 to align with the wearer's ear canal or concha, both vertically and horizontally, by also adjusting the length distance 7.198, 7.199 between front transparent panel 7.28 and rear ends 7.48, 7.56. A nib 7.192 on each rearward temple portion (e.g., rearward temple portion 7.88 shown in FIGS. 83–84) engages a lip 7.194 at the rearward-opening mouth of the corresponding front temple portion so as to retain rearward temple portion 7.88 within the front temple portion as the temple length adjustment means is extended to its limit.

Testing of human subjects has revealed that, as the head gets larger, the vertical distance from the center of the ear canal to the wearer's brow increases as does the horizontal distance from the wearer's brow to the center of the ear canal. The provision of both first and second adjustment means (i.e., first and second temple spread-and-length adjustment means 7.158, 7.160 and first and second temple length adjustment means 7.66, 7.102) for each temple allows the respective earplug or earpiece 7.38, 7.40 to be correctly aligned with the wearer's ear canal for differently sized wearers.

Earplug or earpiece 7.38, 7.40 is received onto a barb 7.184, 7.186 on respective rearward portions 7.88, 7.124 of temples 7.44, 7.52, with barbs 7.184, 7.186 preferably having enlarged tips 7.188, 7.190 for retaining the respective earplugs or earpieces thereon. The barbs 7.184, 7.186 may be angled slightly to mate with the ear canal of the wearer, and various rearward portions 7.88, 7.124 may be provided having different angles for barbs 7.184, 7.186 so as to accommodate differing human anatomies, whether by providing various rearward portions having different fixed angles for barb 7.184, 7.186 or whether by providing a rearward portion similar to that shown in FIGS. 42–46 and FIG. 53 for the fifth embodiment of the present invention, it being further understood that the ear microphone and audio earpieces heretofore described for the fifth embodiment are equally applicable for use with the seventh embodiment. Earplug or earpieces 7.38, 7.40 are preferably constructed of unfoamed poly-vinyl chloride ("PVC") plastisol, although other materials may be used as well.

First and second temples 7.44, 7.52 are resilient and substantially shape-retaining, preferably being made of resilient plastic, and transmit the inward pressure created by the resilience of elongated browpiece portion 7.32 to rear temple portions 7.88, 7.124 which, in turn, exert an inwardly-directed force acting through earplugs 7.38, 7.40 (i.e., forcing the earplugs 7.38, 7.40 toward each other through the wearer's head), with the inwardly-directed force through each earplug being preferably at least about one Newton (about 3.6 ounces Avoirdupois) and with the inwardly-directed force through each earplug preferably being about 6 ounces Avoirdupois (1.67 Newtons) so as to comfortably secure the eyewear onto the wearer's head during physical activity. If earpiece 7.38, 7.40 is an aural, semi-aural, or supra-aural earplug, then this force also seals the earplug to the ear canal.

FIGS. 76–82 and 86–87 show the eighth embodiment 8.20, which is similar to the seventh embodiment heretofore described except that the eighth embodiment 8.20 omits the forward first and second temple spread-and-length adjustment means of the seventh embodiment, and only has rearward first and second temple length adjustment means 8.66, 8.102.

Like the seventh embodiment, the eighth embodiment 8.20 comprises a front guard portion 8.22 including a resilient elongated member or front frame browpiece portion 8.32 and first and second temples 8.44, 8.52 fixedly attached to the browpiece portion 8.32. Temples 8.44, 8.52 are fixedly attached to browpiece portion 8.32, preferably as a rearwardly-curving extension thereof. The rear ends 8.48, 8.56 of the rear temple portions 8.88, 8.124 of the temples 8.44, 8.52 have an earpiece or earplug 8.38, 8.40 attached thereto remote from front guard portion 8.22, and the earpiece or earplug 8.38, 8.40 is insertingly received into the ear E of a wearer, preferably into the ear canal C or concha 207 of the wearer's ear, thereby supporting the eyewear 8.20 on the wearer's head without having over-the-ear rear portions of the temple, as shown best in FIG. 82. Single or dual lenses (clear or tinted) of front transparent panel 8.28 are mounted to the browpiece portion 8.32 as by being received into a downwardly-facing groove or slot (not shown) in the browpiece portion 8.32 or preferably by being integrally molded with browpiece portion 8.32, and the lenses of front transparent panel 8.28 and eyewear 8.20 are supported on the wearer's nose by a nosepiece or bridge portion 8.30 attached to the lenses of front transparent panel 8.28. The earpiece or earplug 8.38, 8.40, by its receipt into the wearer's ear, thus supports its temple 8.44, 8.52 upon the wearer's head without having any corresponding temple portion extending over the wearer's ear.

The two temples 8.44, 8.52 are substantially mirror images of each other, and a description of one will suffice for both.

Temples 8.44, 8.52 respectively have rearward portions 8.88, 8.124 that are respectively slidably received over and onto the front portions 8.68, 8.104 of respective temples 8.44, 8.52, and dimples (e.g., dimples 8.180 for temple 8.52) on the outside side of front temple portions 8.68, 8.104 selectively engage and extend into the rearward adjustment apertures 8.174, 8.176 on the outside side of respective temple rearward portions 8.88, 8.124. These first and second temple length adjustment means 8.66, 8.102 (best seen in detail in FIGS. 86–88 for length adjustment means 8.102), for respective temples 8.44, 8.52, allow adjustment of the length of temples 8.44, 8.52 so as to permit the earplug or earpiece 8.38, 8.40 to align with the wearer's ear canal or concha, both vertically and horizontally, by adjusting the length distance 8.198, 8.199 between front transparent panel 8.28 and rear ends 8.48, 8.56. A nib 8.192 on each front temple portion (e.g., front temple portion 8.104 shown in FIGS. 87–88) engages a lip 8.194 at the forward-opening mouth of the corresponding rear temple portion so as to retain front temple portion 8.104 within the rear temple portion as the temple length adjustment means is extended to its limit.

Earplug or earpiece 8.38, 8.40 is received onto a barb 8.184, 8.186 on respective rearward portions 8.88, 8.124 of temples 8.44, 8.52, with barbs 8.184, 8.186 preferably having enlarged tips 8.188, 8.190 for retaining the respective earplugs or earpieces thereon. The barbs 8.184, 8.186 may be angled slightly to mate with the ear canal of the wearer, and various rearward portions 8.88, 8.124 may be provided having different angles for barbs 8.184, 8.186 so as to accommodate differing human anatomies, whether by providing various rearward portions having different fixed angles for barb 8.184, 8.186 or whether by providing a rearward portion similar to that shown in FIGS. 42–46 and FIG. 53 for the fifth embodiment of the present invention, it being further understood that the ear microphone and audio earpieces heretofore described for the fifth embodiment are equally applicable for use with the eighth embodiment. Earplug or earpieces 8.38, 8.40 are preferably constructed of unfoamed polyvinyl chloride ("PVC") plastisol, although other materials may be used as well.

Temples 8.44, 8.52 of the eighth embodiment are constructed so as to curvingly bend slightly inward toward the wearer's head and thereby exert inward pressure to retain the earplugs 8.38, 8.40 within the wearer's ear. First and second temples 8.44, 8.52 are resilient and substantially shape-retaining, preferably being made of resilient plastic, and transmit the inward pressure created by the resilience of elongated browpiece portion 8.32 to rear temple portions 8.88, 8.124 which, in turn, exert an inwardly-directed force acting through earplugs 8.38, 8.40 (i.e., forcing the earplugs 8.38, 8.40 toward each other through the wearer's head), with the inwardly-directed force through each earplug being preferably at least about one Newton (about 3.6 ounces Avoirdupois) and with the inwardly-directed force through each earplug preferably being about 6 ounces Avoirdupois (1.67 Newtons) so as to comfortably secure the eyewear onto the wearer's head during physical activity. If earpiece 8.38, 8.40 is an aural, semi-aural, or supra-aural earplug, then this force also seals the earplug to the ear canal.

As with the previous embodiments, to use the fifth, sixth, seventh and eighth embodiments, a wearer adjusts the adjustment means of the eyewear so that the earplug or earpiece is comfortably aligned with the wearer's ear canal when the eyewear is placed upon the wearer's head. The nosepiece is rested upon the wearer's nose, and the eyewear is retained on the wearer's head by the earplug or earpiece inserted into the wearer's ear(s). It is thus not possible to comfortably wear the eyewear without having ear protection as well because, if the earpieces are not placed within the wearer's ear, they will annoyingly project into the side of the wearer's face.

An "overglasses" ninth preferred embodiment is shown in FIGS. 89–91, with identifying reference designators marked similarly to the prior embodiments, except with the prefix "9." It shall be understood that many aspects of all embodiments are substantially the same, and only the differences will be treated in detail. It shall also be understood that the earpieces/earplugs 9.38, 9.40 shown in FIGS. 89–90 are shown in dotted outline so as to reveal the hidden structure of the barb on which the earpieces are received, and the wearer's standard glasses are shown in dotted outline beneath the overglasses ninth embodiment.

Overglasses ninth embodiment 9.20 provides the advantages and benefits of the present invention for those who also wear standard glasses. The frontpiece guard portion 9.22 of ninth embodiment 9.20 is substantially similar to the frontpiece of well-known overglasses safety goggles, having a front transparent panel 9.28 and with frontpiece guard portion 9.22 being sized for wearing over standard eyeglasses as shown in FIG. 89.

Front guard portion 9.22 of ninth embodiment 9.20 includes a resilient elongated member or front frame browpiece portion 9.32 and first and second temples 9.44, 9.52 hingedly attached to the browpiece portion 9.32 as by hinges 9.50, 9.58. The rear ends 9.48, 9.56 of the rear temple portions 9.88, 9.124 of the temples 9.44, 9.52 have an earpiece or earplug 9.38, 9.40 attached thereto remote from front guard portion 9.22, and the earpiece or earplug 9.38, 9.40 is insertingly received into the ear E of a wearer, preferably into the concha 207 or ear canal of the wearer's ear, thereby supporting the eyewear 9.20 on the wearer's head without having over-the-ear rear portions of the temple, as shown best in FIG. 89. Front transparent panel 9.28 is supported on the wearer's nose by a nosepiece or bridge portion 9.30 attached to front transparent panel 9.28. The earpiece or earplug 9.38, 9.40, by its receipt into the wearer's ear, thus supports its temple 9.44, 9.52 upon the wearer's head without having any corresponding temple portion extending over the wearer's ear.

The two temples 9.44, 9.52 are substantially mirror images of each other, and a description of one will suffice for both.

Temples 9.44, 9.52 respectively have rearward portions 9.88, 9.124 that are preferably substantially similar to rearward portions 7.88, 7.124 heretofore described. Because of this great similarity with rearward portions 7.88, 7.124, the structural features of first and second temple length adjustment means 9.66, 9.102 will not be repeated because they are substantially the same as heretofore described in detail.

Earplug or earpiece 9.38, 9.40 is received onto a barb 9.184, 9.186 on respective rearward portions 9.88, 9.124 of temples 9.44, 9.52, with barbs 9.184, 9.186 preferably having enlarged tips 9.188, 9.190 for retaining the respective earplugs or earpieces thereon. The barbs 9.184, 9.186 may be angled slightly to mate with the ear canal of the wearer, and various rearward portions 9.88, 9.124 may be provided having different angles for barbs 9.184, 9.186 so as to accommodate differing human anatomies, whether by providing various rearward portions having different fixed angles for barb 9.184, 9.186 or whether by providing a rearward portion similar to that shown in FIGS. 42–46 and FIG. 53 for the fifth embodiment of the present invention, it being further understood that the ear microphone and audio earpieces heretofore described for the fifth embodiment are equally applicable for use with the ninth embodiment. Earplug or earpieces 9.38, 9.40 are preferably constructed of unfoamed polyvinyl chloride ("PVC") plastisol, although other materials may be used as well.

The hinges 9.50, 9.58 of temples 9.44, 9.52 of the ninth embodiment are constructed so as to force the temples slightly inward toward the wearer's head and thereby exert inward pressure to retain the earpieces 9.38, 9.40 within the wearer's ear. First and second temples 9.44, 9.52 are resilient and substantially shape-retaining, preferably being made of resilient plastic, and transmit the inward pressure created by the hinges and by the resilience of elongated browpiece portion 9.32 to rear temple portions 9.88, 9.124 which, in turn, exert an inwardly-directed force acting through earpieces 9.38, 9.40 (i.e., forcing the earpieces 9.38, 9.40 toward each other through the wearer's head), with the inwardly-directed force through each earpiece being preferably at least about one Newton (about 3.6 ounces Avoirdupois) and with the inwardly-directed force through each earpiece preferably being about 6 ounces Avoirdupois (1.67 Newtons) so as to comfortably secure the eyewear onto the wearer's head during physical activity. If earpiece 9.38, 9.40 is an aural, semi-aural, or supra-aural earpiece, then this force also seals the earpiece to the ear canal.

To use the overglasses ninth embodiment, a wearer first places his or her standard eyeglasses on his or her head in the usual manner with the temples of the standard eyeglasses supportingly extending and looping over the wearer's ears as shown in FIG. 89, then the wearer adjusts the temple length adjustment means of the ninth embodiment of the eyewear so that the earplug or earpiece is comfortably aligned with the wearer's ear canal when the eyewear is placed upon the wearer's head. The frontpiece guard portion of the overglasses ninth embodiment is placed over the wearer's glasses with the nosepiece of the ninth embodiment resting upon the wearer's nose, and the ninth embodiment of the eyewear is retained on the wearer's head by the earplug or earpiece inserted into the wearer's ear(s). It is thus not possible to comfortably wear the eyewear without having ear protection as well because, if the earpieces are not placed within the wearer's ear, they will annoyingly project into the side of the wearer's face.

Although the present invention has been described and illustrated with respect to a preferred embodiment and a preferred use therefor, it is not to be so limited since modifications and changes can be made therein which are within the full intended scope of the invention.

We claim:

1. Eyewear for support by the ears of a human being, said eyewear comprising:
   (a) a front guard portion including a front transparent panel;
   (b) a first temple attached to said front guard portion, said first temple being substantially shape-retaining and length-inelastic and having a rear temple portion remote from said front guard portion;
   (c) a first earpiece attached to said rear temple portion of said first temple and adapted for supporting said first temple from a concha of a first ear of the human being by receipt of said first earpiece into the concha of the first ear, said first temple having no means of support extending over the top of the human being's first ear; and
   (d) a second temple attached to said front guard portion and extending rearwardly therefrom.

2. The eyewear as recited in claim 1, in which said eyewear further comprises first earphone means for converting an electrical signal to sound within said first earpiece.

3. The eyewear as recited in claim 2, in which said eyewear further comprises a microphone.

4. The eyewear as recited in claim 1, in which said first temple further includes first temple length adjustment means for selectively adjusting said first temple's length.

5. The eyewear as recited in claim 1, in which said second temple is substantially shape-retaining and length-inelastic and has a rear temple portion remote from said front guard portion; and said eyewear further comprises:
   a second earpiece attached to said rear temple portion of said second temple and adapted for supporting said second temple from a concha of a second ear of the human being by receipt of said second earpiece into the concha of the second ear, said second temple having no means of support extending over the top of the human being's second ear.

6. The eyewear as recited in claim 5, in which said eyewear further comprises first earphone means for converting an electrical signal to sound within said first earpiece and second earphone means for converting an electrical signal to sound within said second earpiece.

7. The eyewear as recited in claim 6, in which said eyewear further comprises a microphone.

8. The eyewear as recited in claim 5, in which said first temple further includes first temple length adjustment means for selectively adjusting said first temple's length and said second temple further includes second temple length adjustment means for selectively adjusting said second temple's length.

9. Eyewear for support by the ears of a human being, said eyewear comprising:
   (a) a front guard portion including a front transparent panel;

(b) a first temple attached to said front guard portion and extending rearwardly therefrom, said first temple having a rear temple portion remote from said front guard portion;

(c) a first earpiece attached to said rear temple portion of said first temple and adapted for supporting said first temple from a concha of a first ear of the human being by receipt of said first earpiece into the concha of the first ear, said first temple having no means of support extending over the top of the human being's first ear; and (d) a second temple attached to said front guard portion and extending rearwardly therefrom;

said first temple being resilient and said rear temple portion of said first temple exerting an inwardly-directed force acting through said first earpiece and toward said second temple.

10. The eyewear as recited in claim 9, in which said eyewear further comprises first earphone means for converting an electrical signal to sound within said first earpiece.

11. The eyewear as recited in claim 10, in which said eyewear further comprises a microphone.

12. The eyewear as recited in claim 9, in which said first temple further includes first temple length adjustment means for selectively adjusting said first temple's length.

13. The eyewear as recited in claim 9, in which said second temple has a rear temple portion remote from said front guard portion; and said eyewear further comprises:

a second earpiece attached to said rear temple portion of said second temple and adapted for supporting said second temple from a concha of a second ear of the human being by receipt of said second earpiece into the concha of the second ear, said second temple having no means of support extending over the top of the human being's second ear;

said second temple being resilient and said rear temple portion of said second temple exerting an inwardly-directed force acting through said second earpiece and toward said first temple.

14. The eyewear as recited in claim 13, in which said eyewear further comprises first earphone means for converting an electrical signal to sound within said first earpiece and second earphone means for converting an electrical signal to sound within said second earpiece.

15. The eyewear as recited in claim 14, in which said eyewear further comprises a microphone.

16. The eyewear as recited in claim 13, in which said first temple further includes first temple length adjustment means for selectively adjusting said first temple's length and said second temple further includes second temple length adjustment means for selectively adjusting said second temple's length.

17. Eyewear for support by the ears of a human being, said eyewear comprising:

(a) a front guard portion including a front transparent panel;

(b) a first temple attached to said front guard portion, said first temple being substantially shape-retaining and length-inelastic and having a rear temple portion remote from said front guard portion; said first temple including first temple length adjustment means for selectively adjusting said first temple's length;

(c) a first earpiece angled slightly upward and attached to said rear temple portion of said first temple and adapted for supporting said first temple from a concha of a first ear of the human being by receipt of said first earpiece into the concha of the first ear, said first temple having no means of support extending over the top of the human being's first ear;

(d) a second temple attached to said front guard portion, said second temple being substantially shape-retaining and length-inelastic and having a rear temple portion remote from said front guard portion; said second temple including second temple length adjustment means for selectively adjusting said second temple's length; and (e) a second earpiece angled slightly upward and attached to said rear temple portion of said second temple and adapted for supporting said second temple from a concha of a second ear of the human being by receipt of said second earpiece into the concha of the second ear, said second temple having no means of support extending over the top of the human being's second ear.

18. The eyewear as recited in claim 17, in which said eyewear further comprises first and second temple spread-and-length adjustment means for selectively adjusting a spread distance between said first and second temples and for selectively adjusting a length distance between said front transparent panel and said rear ends of said first and second temples.

19. The eyewear as recited in claim 17, in which said eyewear further comprises first earphone means for converting an electrical signal to sound within said first earpiece.

20. The eyewear as recited in claim 19, in which said eyewear further comprises an ear microphone within said first earpiece.

21. The eyewear as recited in claim 19, in which said eyewear further comprises second earphone means for converting an electrical signal to sound within said second earpiece.

22. The eyewear as recited in claim 21, in which said eyewear further comprises an ear microphone within said first earpiece.

* * * * *